(12) United States Patent
Lipovsek et al.

(10) Patent No.: US 7,115,396 B2
(45) Date of Patent: *Oct. 3, 2006

(54) PROTEIN SCAFFOLDS FOR ANTIBODY MIMICS AND OTHER BINDING PROTEINS

(75) Inventors: Dasa Lipovsek, Cambridge, MA (US); Richard W. Wagner, Concord, MA (US); Robert G. Kuimelis, Brighton, MA (US)

(73) Assignee: Compound Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/728,078

(22) Filed: Dec. 3, 2003

(65) Prior Publication Data

US 2005/0038229 A1 Feb. 17, 2005

Related U.S. Application Data

(63) Continuation of application No. 09/688,566, filed on Oct. 16, 2000, now abandoned, which is a continuation-in-part of application No. 09/515,260, filed on Feb. 29, 2000, now Pat. No. 6,818,418, which is a continuation-in-part of application No. 09/456,693, filed on Dec. 9, 1999, now abandoned.

(60) Provisional application No. 60/111,737, filed on Dec. 10, 1998.

(51) Int. Cl.
*A61K 38/00* (2006.01)

(52) U.S. Cl. .................................................. 435/69.1
(58) Field of Classification Search ................ 435/69.1
See application file for complete search history.

(56) References Cited

U.S. PATENT DOCUMENTS

| | | | |
|---|---|---|---|
| 5,235,041 | A | 8/1993 | Cappello et al. |
| 5,514,581 | A | 5/1996 | Ferrari et al. |
| 5,545,620 | A | 8/1996 | Wahl et al. |
| 5,641,648 | A | 6/1997 | Ferrari et al. |
| 5,770,697 | A | 6/1998 | Ferrari et al. |
| 5,792,742 | A | 8/1998 | Gold et al. |
| 6,018,030 | A | 1/2000 | Ferrari et al. |
| 6,383,775 | B1 | 5/2002 | Duff et al. |
| 6,462,189 | B1 | 10/2002 | Koide |
| 6,660,492 | B1 | 12/2003 | Bode et al. |
| 6,818,418 | B1 | 11/2004 | Lipovsek |
| 2002/0019517 | A1 | 2/2002 | Koide |
| 2003/0104520 | A1 | 6/2003 | Ellington et al. |
| 2003/0170753 | A1 | 9/2003 | Koide |
| 2005/0255548 | A1 | 11/2005 | Lipovsek |

FOREIGN PATENT DOCUMENTS

| WO | WO 98/31700 | 7/1998 |
|---|---|---|
| WO | WO 98/56915 | 12/1998 |
| WO | WO-99/51773 | 10/1999 |
| WO | WO 00/34784 | 6/2000 |
| WO | WO 01/64942 | 9/2001 |
| WO | WO 01/64942 A | 9/2001 |
| WO | WO 02/04523 A2 | 1/2002 |
| WO | WO 02/32925 | 4/2002 |
| WO | WO-02/32925 | 4/2002 |
| WO | WO 03/022858 A2 | 3/2003 |

OTHER PUBLICATIONS

Baron et al. H NMR Assignment and Secondary Structure of the Cell Adhesion Type III Module of Fibronectin. Biochemistry 31, 2068-2073 (1992).
Bianchi et al. High Level Expression and Rational Mutagenesis of a Designed Protein, the Minibody. J. Mol. Biol. 236, 649-659 (1994).
Boder et al. Yeast Surface Display for Screening Combinatorial Polypeptide Libraries. Nat. Biotech. 15, 553-557 (1997).
Bork and Doolittle. Proposed Acquisition of an Animal Protein Domain by Bacteria. PNAS 89, 8990-94 (1992).
Campbell et al. Building Proteins with Fibronectin Type III Modules. Structure 2, 333-337 (1994).
Clackson et al. Making Antibody Fragments Using Phage Display Libraries. Nature 352, 624-628 (1991).
Clackson and Wells. In Vitro Selection from Protein and Peptide Libraries. TIB TECH 12, 173-184 (1994).
Clarke et al. Folding and Stability of a Fibronectin Type III Domain of Human Tenascin. J. Mol. Biol. 270, 771-778 (1997).
Copie et al. Solution Structure and Dynamics of Linked Cell Attachment Modules of Mouse Fibronectin Containing the RGD and Synergy Regions: Comparison with the Human Fibronectin Crystal Structure. J. Mol. Biol. 277, 663-682 (1998).
Cota et al. Two Proteins with the Same Structure Respond Very Differently to Mutation: The Role of Plasticity in Protein Stability. J. Mol. Biol. 302, 713-725 (2000).
Dickinson et al. Crystal Structure of the Tenth Type III Cell Adhesion Module of Human Fibronectin. J. Mol. Biol. 236, 1079-1092 (1994).
Dickinson et al. Crystals of the Cell-Binding Module of Fibronectin Obtained from a Series of Recombinant Fragments Differing in Length. J. Mol. Biol. 238, 123-127 (1994).
Ely et al. Common Molecular Scaffold for two Unrelated RGD Molecules. Prot. Eng. 8, 823-827 (1995).
Ghosh et al. Structure of NF-KB p50 Homodimer Bound to a kB Site. Nature 373, 303-310 (1995).
Grant et al. Structural Requirements for Biological Activity of the Ninth and Tenth FIII Domains of Human Fibronectin. J. Biol. Chem. 272, 6159-6166 (1997).
Hamers-Casterman et al. Naturally Occuring Antibodies Devoid of Light Chains. Nature 363, 446-448 (1993).
Hocking et al. A Novel Role for the Integrin-Binding III-10 Module in Fibronectin Matrix Assembly. J. Cell Biol. 133, 431-444 (1996).

(Continued)

*Primary Examiner*—Bruce R. Campell
*Assistant Examiner*—Maury Audet
(74) *Attorney, Agent, or Firm*—Fish & Neave IP Group Ropes & Gray LLP

(57) ABSTRACT

Disclosed herein are proteins that include an immunoglobulin fold and that can be used as scaffolds. Also disclosed herein are nucleic acids encoding such proteins and the use of such proteins in diagnostic methods and in methods for evolving novel compound-binding species and their ligands.

33 Claims, 25 Drawing Sheets

OTHER PUBLICATIONS

Hocking et al. Activation of Distinct Alpha5Beta1-Mediated Signalling Pathways by Fibronectin's Cell Adhesion and Matrix Assembly Domains. J. Cell. Biol. 141, 241-253 (1998).

Hynes. Integrins: Versatility, Modulation, and Signaling in Cell Adhesion. Cell 69, 11-25 (1992).

Kohler and Milstein. Continuous Cultures of Fused Cells Secreting Antibody of Predefined Specificity. Nature 256, 495-497 (1975).

Koide et al. Directed Evolution of Fibronectin Type III Domain to Novel Ligand Binding Proteins. FASEB J. 11(9), Supp., Abstract M40.

Koide et al. The Fibronectin Type III Domain as a Scaffold for Novel Binding Proteins. J. Mol. Biol. 284, 1141-1151 (1998).

Koide et al. Directed Evolution of Fibronectin Type III Domain to Novel Ligand Binding Proteins. Designing Small and Large Molecules I, Abstract 1739.

Ku and Schultz. Alternate Protein Frameworks for Molecular Recognition. PNAS 92, 6552-6556 (1995).

Leahy et al. Structure of a Fibronectin Type III Domain from Tenascin Phased by MAD Analysis of the Selenomethionyl Protein. Science 258, 987-991 (1992).

Lee et al. Strong Inhibition of Fibrogen Binding to Platelet Receptor Alpha2b beta 3 by RGD Sequences Installed into a Presentation Scaffold. Prot. Eng. 6, 745-754 (1993).

Litvinovich and Ingham. Interactions Between Type III Domains in the 110 kDa Cell-Binding Fragment of Fibronectin. J. Mol. Biol. 248, 611-626 (1995).

Lombardo et al. Conformational Flexibility and Crystallization of Tandemly Linked Type III Modules of Human Fibronectin. Prot. Sci. 5, 1934-1938 (1996).

Main et al. The Three-Dimensional Structure of the Tenth Type III Module of Fibronectin: An Insight into RGD-Mediated Interactions. Cell 71, 671-678 (1992).

Markland et al. Iterative Optimization of High-Affinity Protease Inhibitors Using Phage Display. 1. Plasmin. Biochemistry 35, 8045-8057 (1996).

Markland et al. Iterative Optimization of High-Affinity Protease Inhibitors Using Phage Display. 2. Plasma Kallikrein and Thrombin. Biochemistry 35, 8058-8067 (1996).

McConnell and Hoess. Tendamistat as a Scaffold for Conformationally Constrained Phage Peptide Libraries. J. Mol. Biol. 250, 460-470 (1995).

Meinke et al. Cellulose-Binding Polypeptides from *Cellulomonas fimi*: Endoglucanase D (CenD), a Family A Beta-1, 4-Glucanase. J. Bacteriol. 175, 1910-1918 (1993).

Muller et al. Structure of the NF-kB p50 Homodimer Bound to DNA. Nature 373, 311-317 (1995).

Ngo et al. "Computational Complexity, Protein Structure Prediction, and the Levinthal Paradox" in the Protein Folding Problem and Tertiary Structure Prediction, Merz & Le Grand, ed. Birkhauser, Boston, p. 491-495 (1994).

Nord et al. Binding Proteins Selected from Combinatorial Libraries of an Alpha-Helical Bacterial Receptor Domain. Nat. Biotech. 15, 772-777 (1997).

Nord et al. A Combinatorial Library of an Alpha-Helical Bacterial Receptor Domain. Prot. Eng. 8, 601-608 (1995).

Nygren and Uhlen. Scaffolds for Engineering Novel Binding Sites in Proteins. Curr. Op. Struc. Biol. 7, 463-469 (1997).

Plaxco et al. Rapid Refolding of a Proline-Rich All-Beta-Sheet Fibronectin Type III Module. PNAS 93, 10703-10706 (1996).

Plaxco et al. A Comparison of the Folding Kinetics and Thermodynamics of Two Homologous Fibronectin Type III Modules. J. Mol. Biol. 270, 763-770 (1997).

Potts and Campbell. Fibronectin Structure and Assembly. Curr. Opin. Cell Biol. 6, 648-655 (1994).

Potts and Campbell. Structure and Function of Fibronectin Modules. Matrix Biol. 15, 313-320 (1996).

Roberts and Szostak. RNA-Peptide Fusions for the In Vitro Selection of Peptides and Proteins. PNAS 94, 12297-12302 (1997).

Rottgen and Collins. A Human Pancreatic Secretory Trypsin Inhibitor Presenting a Hypervariable Highly Constrained Epitope Via Monovalent Phagemid Display. Gene 164, 243-250 (1995).

Shibata et al. An Attempt to Substitute the Cell Binding Domain of Human Fibronectin in Lambda Phage J Protein: Computer Design and Expression. Biochimie. 75, 459-465 (1993).

Smith and Petrenko. Phage Display. Chem. Rev. 97, 391-410 (1997).

Tramontano et al. The Making of the Minibody: An Engineered Beta-Protein for the Display of Conformationally Constrained Peptides. J. Mol. Recog. 7, 9-24 (1994).

Wang et al. Isolation of a High Affinity Inhibitor of Urokinase-Type Plasminogen Activator by Phage Display of Ecotin. J. Biol. Chem. 270, 12250-12256 (1995).

Watanabe et al. Gene Cloning of Chitinase A1 From Bacillus Circulans WL-12 Revealed its Evolutionary Relationship to Serratia Chintinaseand to the Type III Homology Units of Fibronectin. J. Biol. Chem. 265, 15659-15665 (1990).

Wells, J.A. Additivity of Mutational Effects in Proteins. Biochem. 29, 509-517 (1990).

Williams et al. The Immunoglobulin Superfamily—Domains for Cell Surface Recognition. Ann. Rev. Immunol. 6, 381-405 (1988).

Williams et al. Solution Structures of Modular Proteins by Nuclear Magnetic Resonance. Methods Enzymol. 245, 451-469 (1994).

Bruzik, J. et al., "Spliced leader RNAs from lower eukaryotes are trans-spliced in mammalian cells," *Nature* 360, 692-695 (1992).

Apte, et al., "Anchor-Ligated cDNA Libraries: A Technique for Generating a cDNA Library for the Immediate Cloning of the 5' Ends of mRNAs," *Biotechniques* 15, 890-893 (1993).

Maruyama, K. et al., "Oligo-capping: a single method to replace the cap structure of eukaryotic mRNAs with oligoribonucleotides," *Gene* 138, 171-174 (1994).

Brock, K. et al., "Nucleotide sequencing of 5' and 3' termini of bovine viral diarrhea virus by RNA ligation and PCR," *J. Virol. Methods* 38, 39-46 (1992).

Ferguson, K. et al., "The SL 1 trans-spliced leader RNA performs an essential embryonic function in *Caenorhabditis elegans* that can also be supplied by SL2 RNA," *Genes* Dev. 10, 1543-1556 (1996).

Nilsen, T., "Trans-Splicing in Protozoa and Helminths,"*Infect Agents Dis.* 1, 212-218 (1992).

Roberts, R.W. Totally in vitro protein selection using mRNA-protein fusions and ribosome display. Current Opinion in Chemical Biology, Current Biology Ltd, London, GB, 3, 268-273 (1999), XP002180767 ISSN: 1367-5931.

U.S. Appl. No. 09/456,693, unpublished, abandoned, Lipovsek.

U.S. Appl. No. 09/688,566, unpublished, abandoned, Lipovsek.

DGENE Search Results (pp. 1-33).

```
              1          9 10         19 20         29 30         37 38         47 48         57 58         67 68         77 78         87 88
Hs FND        VSDVPRD-LE VVAATPTSLL ISWDAPAVTV RYYRITYG--- ETGGNSPVQE FTVPGSKSTA TISGLKPGVD YTITVYAVTG RGDSPASSKP ISINYRT     94
Bt FN         VSDVPRD-LE VIAATPTSLL ISWDAPAVTV RYYRITYG--- ETGGSSPVQE FTVPGSKSTA TISGLKPGVD YTITVYAVTG RGDSPASSKP VSINYRT     94
Rn FN         VSDVPRD-LE VIASTPTSLL ISWEpPAVSV RYYRITYG--- ETGGNSPVQE FTVPGSKSTA TINnIKPGAD YTITLYAVTG RGDSPASSKP VSINYQT     1510
Mm FN         VSDIPRD-LE VIASTPTSLL ISWEpPAVSV RYYRITYG--- ETGGNSPVQE FTVPGSKSTA TINnIKPGAD YTITLYAVTG RGDSPASSKP VSINYKT     1611
Oc FN         VSDVPRD-LE VIASTPTSLL ISWEXPAVTV RYYRITYG--- ETppN----- ---------- ---------- ---------- ---------- -------     712
Gg FN         VSDVPRD-LE VNpTSPTSLE ISWDAPAVTV RYYRITYG--- ETGGSSPVQE FTVPGTMSrA TITGLKPGVD YTITVYAVTG RGDSPASSKP VTVTYKT     64
Xl FN         VSDVPTD-LE VTSSSPNTLT ISWEAPAVSV RYYRITYS--- ETGGhGPEKE FTVPGISNTA TIRGLNPGVS YTITVYAVTG RGDSPASSKP LTIIHKT     443
Cf FN         AiDAPSn-Lr FLATTPnSLL VSWQpPrArI TGYIIKYe--- kpGSpprEVV prprPGVTeA TITGLePGTE YTIQVIALKn NQKSepLIGr kKTdEL-     1611
Ec FN         AiDAPSn-Lh FLATTPnSLL ISWQpPrArI TGYIIKYe--- kpGSpprEVV prphPGVTeA TITGLePGTE YTIQVIALKn NQKSepLIGr rKTdEp-     197
Hs TC         VS-PPKD-Lv VTeVTeeTVN LAWDn-eMrV -THEGGIEMQ FrVPGDQTST IIQeLePGVE YFIRVFAIle NKKSipVSAr V------     197
Ss TP         VS-PPKD-Li VTeVTeeTVN TeVLVVYTP- -THEdGIEMQ FrVPGDQTST TIReLePGVE YFIRVFAIle NKKSipVSAr V------     686
Mm TX         MiDGPQD-Lr VVAVTPTTLD LSWlrPQAeV DrFVVSYV-- --SAGNqRVi LeVPPEADrT QLIdLMPGVE YVVVTAERG HAVSypPASIr ANTG---     686
Hs CAP        TlpVPvvSLn IYdVGPTTMH VQWQp-VGGA TGYIlsSYkPV kDTEpTrpKE kDTEpTrpKp QdVkLRdVTH ---------- ---------- -------     889
Oc C12        TlpVPvvSLN IYdVGPTTMH VQWQp-VGGA TGYIlsSYkPV kDTEpTrpKp ---------- ---------- ELDGLLPNTE YTVTVYAMF- e------     1551
Gg C14        LaIpmaSDLk LYdVShSSMR AKWnG-VAGA TGMILYAPL TEGLAAdEKE ---------- ---------- ELSGLLPNTE YTVTVYAMFG eeASDpVTGq e------     322
Hs U1         LaIpmaSDLl LYdVTenSMR VKWDA-VpGA SGYILIYAPL TEGLAGdEKE MkIGETHTdI ---------- ---------- ---------- -------     508 var.          -   -   -  -    -      -   -      -   -     -     -       -           -           -          -          -    321 cons.         P   L   V  SL     W      V  V  Y I Y   I  L PGVD Y ITV  A    G            S    P
              M   I      TV                A  F V        L  I  NTE  VQL                N    R
              L         M                  I    L           AS   R                      E
                F
```

Fig. 4

BOLD           identical to Hs FND lower case     non-conservative substitution
               (charge reversal, change between hydrophobic
               and charged, addition or removal of P)
               position of non-conservative substitutions CAP    Collagen alpha precursor
C12    Collagen type 12
FND    Fibronectin type III domain
FN     Fibronectin
TP     Tenascin precursor
TC     Tenascin-C
U1     Undulin 1

Bt     Bovis taurus              cow
Cf     Canis familiaris          dog
Ec     Equus caballis            horse
Ss     Sus scrofa                pig
Hs     Homo sapiens              human
Oc     Oryctolagus cuniculus     rabbit
Xl     Xenupus laevis            African clawed frog

```
            1             15 16        CDR-H1          45 46     CDR-H2
Llama V_H   DVQLQESGGGLVQAG GSLRLSCAASGRTGS TYDMGWFRQAPGKER -ES-VAAINWDSARTYY
Human 10Fn3 VSDVPRDLEVVAATP TSLLFSWDAPAVTVR YYRITYGETGGNSLV QEFTVPGSKS------
            1             15    ↓      BC  31           45 46    DE
                                R
                                Q 61         75 76         90 91   CDR-H3 106      117
Llama V_H   ASSVRGRFTISRDNA KKTVYLQMNSLKPED TAVYTCGAGEGGTWD SWGQGTQVTVSS
Human 10Fn3 ------TATISGL-- KPGVDY--------- TITGYAVTGRGDSPA SSKPISINYRT-
            56 ↓        63               69       FG   84         94
               I
```

FIG. 25A

ROUND 9 (32)

| | 1 | 15 16 | BC DAPAVTV3031 | 45 46 | DE GSKS | 60 61 | 74 75 | FG | 90 | SEQ.ID.NO. |
|---|---|---|---|---|---|---|---|---|---|---|
| WT | VSDVPRDLEVVAATP | TSLLISWDAPAVTVR | YRRITYGETGGNSPV | QEFTVPGSKSTATIS | GLKPGVDY-TITVYA | VGRGDSPASSKPIS | INYRT | | | 33 |
| T09.08 | VSEIPRDLEVVAATP | TSLLPSWDAPAVTVR | YRRITYGETGGNSLV | QEFTVPGSKSTATIS | GLKPGVDYNTIGYA | VTTYRTRIDKQPIS | INYRT | | | 34 |
| T09.26 | VSDVPRDLEVVAATP | TSLLISWDAPAVTVR | YRRITYGETGGNSPV | QEFTVPELNPTATIS | RLKPGVDY-TITVYA | VTQNGTPRRHLRPNF | H | | | 35 |
| T09.20 | VSDVPRDLEVVAATP | TGLLISWEKSRMTTR | YRRITYGETGGNSPV | QEFTVPDVNTIIVHA | GLKPGVDY-TITVYA | VLLNQNSDHTYPIS | INYRT | | | 36 |
| T09.25 | VSDVPRDLDVVAATP | TSLLISWDS---BHR | YRSANGETGGNSPV | QVFTVPQRRQTATIS | GLKPGVDY-TITVYA | VTPDGSRHMLTKPIS | INYRT | | | 37 |
| T09.30 | VSDVPRDLEVVAATP | TSLLISWHANHIDMR | YRSANGETGGNSPV | QVFTVPQRRQTATIS | GLKPGVDY-TITVYA | VTPKNQGRRRQ---G | INYRT | | | 38 |
| T09.02 | VSDVPRDLEVVAATS | TSLLISWRTPASPHG | YRRITYGETGGNSPV | EEFTVPLLMFTATIS | GLKPGVDY-TITVYA | VTPTHMLKPQSMPIS | INYRT | | | 39 |
| T09.34 | VSDVPRDLEVVAATP | TSLLISWRTPASPHG | YRRITYGETGGNSPV | EEFTVPLLMPTATIS | GLKPGVDY-TITVYA | VTPTHMLKPQSMPIS | INYRT | | | 40 |
| T09.03* | VSDVPRDLEVVAAAS | TCLLISWRPNPRLSR | YRRITYGETGGNSPV | QEFTVPGLFSTATIS | GLNPGVDY-TITVYA | VTPKETSNIFLAPIS | INYRT | | | 41 |
| T09.13 | VSDVPRDLEVVAATS | TSLLISWRPNFRLSR | YRRITYGETGGNSPV | QEFTVPGLFSTATIS | GLKPGVDY-TITVYA | VTPKETSNIFLAPIS | INYRT | | | 42 |
| T09.29 | VSDVPRDPEVVAATP | TSLLISWFRSLQRDR | YRRITYGETGGNSPV | QEFTVPGFFSTATIS | GLKPGVDY-TITVYA | VTASRNEDTRPGPIS | INYRT | | | 43 |
| T09.01 | VSDVPRDLEVVAATP | TSLLISWFRSLQRDR | DYRLITYGETGGNSPV | QEFTVPFRMKTATIS | GLKPGVDY-TITVYA | ITPPDRMEPPKGPIS | INYRT | | | 44 |
| T09.14 | VSDVPRDLEVVAATP | TSLLISWYRHTYRDR | YRRITYGETGGNSPV | QEFTVPPWATTATIS | GLKPGVDY-TIAVYA | VTDNGYDVHTKRPIS | INYRT | | | 45 |
| T09.24 | VSDVPRDLEVVAAP | TSLLISWYRHTYRDR | YRRITYGETGGNSPV | QEFTVPPWATTATIS | GLKPGVDY-ALAVYA | VTDNGYDVHTKRPIS | INYRT | | | 46 |
| T09.19 | VSDVPRDLEVVAATP | TSQLISWPGWYPSR | YRRITYGETGGNSPV | QEFTVPPWARTATIS | GLKPGVDY-TITVYA | VTDYSDPSQVHTENS | INYRT | | | 47 |
| T09.31 | VSDVPRDLEVVAATP | TSRLISWRPGRTYSR | -YRLITYGETGGNSPV | QEFTVPWANTATIS | GLKPGVDY-TITVYA | VTPLPITLVHGPIS | INYRT | | | 48 |
| T09.07 | VSDVPRDLEVVAATP | TSRLISWASPFMWCR | YYRITYGETGGNGPV | QEFTVPPWATTATIS | GLKPGVDY-TITVYA | VTEYLPEWNMTQPIS | INYRT | | | 49 |
| T09.36 | VSDVPRDLEVVAATP | TSRLISWASPPMMCR | YYRITYGETGGNSPV | QEFTVPPWMATTATIS | GLKPGVDY-TITVYA | VTEYLPEWNMTQPIS | INYRT | | | 50 |
| T09.16 | -NTTHYRKNNYYATP | TSRLISWNRSGLQSR | YRRITYGETGGNSPV | QEFTVPPWASIATIS | GLKPGVDY-TITVYA | VTDKSDTKYDDPIS | INYRT | | | 51 |
| T09.23 | VSDAPRDLEVVAATP | TSRLISWNRSGLQSR | YRRITYGETGGNSPV | QEFTVPPWHASIATIS | GLKPGVDY-TITMYA | VTSATRTVKRD-PIS | INYRT | | | 52 |
| T09.21 | VSDVPRDLDVVAATP | TSRLISWNRSGLQSR | YRRITYGETGGNSPV | QEFTAPPWASIATIG | GLKPGVDY-TITVYA | VTSNVGRLDTRYPIS | INYRT | | | 53 |
| T09.33* | VSDVPRDLDVVAATP | TSRLISWNRSGLQSR | YRRITYGETGGNSPV | QEFTRPPWASIATIG | GLKPGVDY-TITVYA | VTSNVGRLDTRYPIS | INYRT | | | 54 |
| T09.10 | VSDVPRDLEVVAATP | TSRLISWNRSGLQSR | YRRITYGETGGNSPV | QEFTVPPWASIATIS | GLKPGVDY-TITVYA | VTKRPQRHALVTPIS | INYRT | | | 55 |
| T09.28 | VSDVPRDLEVVAATP | TSRLISWNHPGPFSR | YRRITYGETGGNSPV | QEFTVPPWASIATIS | GLKPGVDY-TITVYA | VTETPSTKPNVPIS | INYRT | | | 56 |
| T09.15 | VSDVPRDLEVVAAT- | TSLLISWDYARTGDR | YRRITYGETGGNSPV | QEFTVPPWASIATIG | GLKPGVDY-TITVYA | | | | | 57 |
| T09.09 | VSDVPRDLEVVAATS | TBLLISMYLARQPR | YRRITYGETGGNSPV | QEFTAPPWASIATIG | GLKPGVDY-TITVYA | VTAQTGHHLHDKPIS | INYRS | | | 58 |
| T09.35 | VSDVPRDLEVVAATP | TSLLISMDISRYKER | YRRITYGETGGNSPV | QEFTVPWASIT-IG | GLKPGVDY-TITVYA | VTAQTGHHLHDEPIS | INYRT | | | 59 |
| T09.06 | VSDVPRDLQIVAATP | TSRLISRPTENPPR | YRRITYGETGGNSPV | QEFTVPPWASIT-IG | GLKPGVDY-TITVYA | VTAQTGHHLHDKPIS | INYRT | | | 60 |
| T09.11 | VSDVPRDLEVVAATP | TSRLICWRPTSPPR | YRRITYGETGGNSPV | QEFTVPPWASIATIS | GLRPGVDY-TITVYA | VTAQTGHHLHDKPIS | INYRT | | | 61 |
| T09.12* | VSDVPRDLEVVAATP | TSRLISWRPTSNPFR | YRRITYGETGGNSPV | QEFTVPPWASIATIS | GLKPGVDY-TITVYA | VTAQTGHHLHDKPIS | INYRT | | | 62 |
| T09.17 | VSDVPRDLEVVAATP | TBQLISMTNPTAR | YRLSYGETGGNBPV | QEFTVPPWATTATIS | GLKPGVDY-TITVYA | VTSLITRRHRAPIS | INYRT | | | 63 |
| T09.04 | VSDVPRDLEVVAATP | TSLLISWTRHBFVR | YRRITYGETGGNSPV | QEFIVPPWATTATIS | GLKPGVDY-TITVYA | VTELITRRHRAPIS | INYRT | | | 64 |
| T09.05 | VSDVPRDLEVVAATP | TSRLISWTRHBFVR | YRRITYGETGGNSPV | QEFIVPPWATTATIS | GLKPGVDY-TITVYA | VTMPTNWRFPHRPIS | IDYRT | | | 65 |

FIG. 25B
ROUND 10 (29)

| | 1 | 15 16 | BC DAPAVFV3031 | YRLITYGETGGNSPV | 45 46 | DE GSKS | 60 61 | 74 75 | FG | 90 | SEQ.ID.NO. |
|---|---|---|---|---|---|---|---|---|---|---|---|
| WT | VSDVPRDLEVVAATP | TSLLISWDAPAVTVR | DAPAVFV3031 | YRLITYGETGGNSPV | QEFTVPGSKSTATIS | GLKPGVDY-TITVYA | VTGRGDSPASSKPIS | INYRT | 33 |
| T10.37 | VSDVPRDLEVVAATP | TSLLIRERE----RR | | YRLITYGETGGNSPV | QEFTVPGSKSTATIS | GLSPGVDY-TITVYA | VTPHRGHFDLELPIS | INYRT | 66 |
| T10.12 | VSDVPRDLEGVAATP | TSLLIERKDRVBSRR | | YRLITYGETGGNSPV | QEFTVPGSKSTAIIS | GLKPGVDY-TITAYV | VTPHHGHFDLELPIS | INYRT | 67 |
| T10.21 | VSDVPRDLEVVAATP | TSLLISWHRATPNTR | | YRLITYGETGGNSPV | QEFTVPGSKSTATIS | GLKPGVDYNTNTVYA | VTSVNAPPYBGMPIS | INYRT | 68 |
| T10.40 | VSDVPRDLEVVAATA | TSLLBSWYLCTGNNR | | DRKITYGETGGNNR | QAFTVPGSKSTATIS | GLKPGVDY-IPSRCM | LSLASLMSTRNKPIS | INYRT | 69 |
| T10.31a | VSDVPRDMEVVAATP | TSLLISWRTPASFHG | | YRLITYGETGGNSFV | EEFTVPLLMPTATIS | GLKPGVDY-AITVYA | VTPTHMLKPLSMPIS | INYRT | 70 |
| T10.41 | ISDVPRDMEVVAATP | TSLLISWNMAHPHDR | | NYRITYGETGGNSPV | QBSTVFRYLSDTATIS | GPKR-VDY-TITVYA | VNQPTVBAHNHAPIS | INYRT | 71 |
| T10.13 | VSDVPRDLKVVAATP | TSLLISWPPDNATPR | | YYRLITYGETGGNSPV | QEFTVP-LPTTATIS | GLKPGVDYNTITVYA | VTSHRDYHSTGRPIS | INYRT | 72 |
| T10.03 | VSDVPRDLEVVAATP | TSLLISWMLLRDDRR | | YRLITYGETGGNSPV | QEFTVPIFHPTATIS | GRKPGVDYNTITVYA | VTQSTNGNRNDPPIS | INYRT | 73 |
| T10.33 | VSDVPRDLEVVAATP | TSLLISWBPPNDAHR | | YRLITYGETGGNSPV | QEFTVPGSKSTATIS | GLKPGVDY-TNTVYA | VTDQQSYTYYSNPIS | DYRT | 74 |
| T10.27 | VSDVPRDLEVVAATP | TSLLISWSPPNDAHR | | YRLITYGETGGNSPV | QEFTVPGSKSTATIS | GLKPGVDY-TNTVYA | VTDQQSYTYYSNPIS | INYRT | 75 |
| T10.05 | VSDVPRDLEVVAATP | TSLLISWSPPNDAHR | | YRLITYGETGGNSPV | QEFTVPWATTATIS | GLKPGVDY-TITVY- | --TMPTNWRPPHRPIS | INYRT | 76 |
| T10.01 | VSDVPRDLEVVAATP | TSQLISWTTRHSPVR | | YRLITYGETGETGEN | QEFTVPWATTATIS | GLKPGVDY-TITVYA | VTMPTNWRPPHRPIS | INYRT | 77 |
| T10.34 | VSDVPRDLEVVAATP | TSRLISWNRSGLQSG | | YRLITYGETGGNSPV | QEFTVPWASIATTS | GLKPGVDY-TITVYA | VTSNVGRLDTRYPIS | TNYRT | 78 |
| T10.36 | VSDVPRDLEVVAATP | TSRLISWNRSGLQSK | | YRRITYGETGGNSPV | QEFTVPWASIA-IS | GLKPGVDY-TITVYA | VTSNVGRLDTRYPIF | INYRT | 79 |
| T10.30 | VSDVPRDLEVVAATP | TSRLISWNRSGLQSR | | YRRITYGETGGNSPV | QEFTVPWASIATIS | GLKPGVDY-TITVYA | VT | | 80 |
| T10.06 | VSDVPRDLEVVAATP | TSRLISWNRSGLQSR | | YRLITYGETGGNSPV | QEFTVPWASIATIS | GLKPGVDY-TITVYA | VTDKSDTYKYDDPIS | INYRT | 81 |
| T10.17 | VSDVPRDLEVVAATP | TSRLISCNRSGLQSR | | YRLITYGETGGNSPV | QEFTVPWASIATIS | GLKPGVDY-TITVYA | VTDKSDTYKYDDPIS | INYRT | 82 |
| T10.18 | VSDVPRDLEVVAATP | TSRLISWNRSGLQSR | | YRLITYGETGGSSPV | QEFTVPWASIATIS | GLKPGVDY-TITVYA | VTPTHNWNDQTRSIS | INYRT | 83 |
| T10.39 | VSDVPRDLEVVAATP | TSRLISWRPTSNFPR | | YRLITYGETGGNSPV | QEFTVPWGSIATIS | GLKPGVDY-TITVYA | VTAQTGYHLHDKPIS | INYRT | 84 |
| T10.02 | VSDVPRDLEVVAA-P | TSRLISWRPGRTYIR | | YRLITYGETGGNSPV | QEFTVPKWANTATIS | GLKPGVDY-TITVYA | VFPPGYPXTEMPIS | INYRT | 85 |
| T10.08 | ISDVPRDLEVVAATP | TSLLISWRRWPHFDR | | YRLITYGETGGNSPV | QEFTVPWG/IATIN | GLKPGVDY-TITVYA | VTNFLSFYTLHPPI- | -NYRT | 86 |
| T10.20 | VSDVPRDLEVVAATP | TSRLISWKIPRRTMTR | | YRLITYGETGETGSPV | QEFTVPWARTATIS | GLKPGVDY-TITVYA | VTLGTGVYTRAQPIS | INYRT | 87 |
| T10.29 | VSDVPRDLEVVAATP | TSQLISWPPGWYPSR | | YRLITYGETGETGSPV | QEFTVPWASIATIS | GLKPGVDY-TITVYA | VTHFFESRRPAKPMS | INYRT | 88 |
| T10.15 | VSDVPRDLEVVAATP | TSLLISWETERSFPR | | YRLITYGETGETGSPV | QEFTVPWGSIATIS | GLKPGVDY-TITVYA | VTEHYRDNGVGHPIP | INYRT | 89 |
| T10.35 | VSDVPRDLEVVAATP | TSLLISWKRSBTFHFR | | YRLITYGETGGNSPV | QEFTVPWASIATIS | GLKPGVDY-TITVYA | VTEHYRDNGVGHPIP | INYRT | 90 |
| T10.26 | VSDVPRDLEVVAATP | TSQLISWRRQVVBTR | | YRLITYGETGGNSPV | QEFTVPWASTAALS | GLKPGADY-TITVYA | VTLNRSPNSARPIS | INYRT | 91 |
| T10.14 | VSDVPRDLEVVAATP | TSRLISWRPTSNHPR | | YRLITYGETGGNSPV | QEFTVPWASIATIS | GLKPGVDY-TITVYA | VTNHKANHHDAEPIS | INYRT | 92 |
| | | | | | | | | VTTNRDHVALPIS | INYRI | 93 |
| S08.02 | VSDVPRDLEVVAATP | TSRLISWNRSGLQSR | | YRLISMGETGGNSPV | QELIVPWASIATIS | GLKPGVDY-TITVYA | VTDKSDTYKYDDPIS | INYRT | 94 |
| S08.03 | VSDVPRDLEVVAATP | TSRLISWNRSGLQSR | | YYRLISMGETGGRGPV | QEFTVPWASIATIS | GLKPGVDY-TITVYA | VTDMSDTYKYDDPIS | INYRT | 95 |

FIG. 25C

Round 14 (22)

| | 1 | 15 16 | BC | | 45 46 | DE | 60 61 | | 75 76 | FG | 90 | SEQ. ID. NO. |
|---|---|---|---|---|---|---|---|---|---|---|---|---|
| WT | VSDVPRDLEVVAATP | TSLLISWDAPAVTVR | DAPAVTV3031 | YYRITYGETGGNSPV | QKFTVFGSKSTATIS | GSKS | GLKPGVDY-TITVYA | | VTGRGDSPASSKPIS | GRGDSPASSK | | 33 |
| T14.25 | VSDVPRDLEVVAATP | TSLLISMDTHNAYNG | | YYRITYGETGGNSPV | RKFTVPHPEVTATIS | | GLKPGVDD-TITVYA | | VTNHMPLRIPGPIS | | | 96 |
| T14.03 | VSDVPRDLEVVAATP | TBLLIXWTRTNANTR | | YYRITYGETGGNSPV | QKFTABANPPTATIG | | GLKPGVDX-TITVYA | | VTPDGSRHMLTKPIS | | | 97 |
| T14.06 | VSDVPRDLEVVAATP | TSRLISWARSGLQSR | | YYRITYGETGGNSPV | QKFTVPFMASIATIS | | GLKPGVDY-TITVYA | | VTDKSDTYKYDDPIS | | | 81 |
| T14.12 | LSDVPRDLEVVAATP | TSRLISWARSGLQSR | | YYRITYGETGGNSPV | QKFTVPFMASIAAIS | | GLKPGVDY-TITVYA | | VTDKSDTYKYDDPIS | | | 98 |
| T14.13 | VSDVPRDLEVVAATP | TSRLISWARSGLQSR | | YYRITYGETGGNSPV | QELTVPPMASIATIS | | GLKPGVDY-TITVYA | | VTDKSDTYKYDDPIS | | | 99 |
| T14.17 | VSDVPRDLEVVAATP | TSRLISWERSGLQSR | | YYRITYGETGGNSPV | QKFTVPPWASIATIS | | GLKHGVDY-TITVYA | | VTDKSDTYKYDDPIS | | | 100 |
| T14.05 | VSDVPRGLEVVAATP | TSRLISWBRSGLQSR | | YYRITYGETBGNSPV | QKFTVPWASMATIS | | GLKPGVDY-TITVYA | | VTDKSDTYKYDDPIS | | | 101 |
| T14.14 | VSDVPRDLEVVAATP | TSRLISWDRSGLQSR | | YYRITYGETGGNSPV | QKFTVPPWASIATIS | | GLKPGVDY-TITVYA | | VTDKSDTYKYDDPTS | | | 102 |
| T14.23 | VSDVPRDLEVVAATP | TSRLISWNRSGLQSR | | YYRITYGETGGNSPV | QKFTVPPWASIATIS | | GLKPGVDY-TITVYA | | VADKSDTYKYDDPIS | | | 103 |
| T14.26 | VSDVPRDLEVVAATP | TSRLISWNRSGLQSR | | YYRITYGETGGNSPV | QKFTVPPWASIATIS | | GLKPGVDY-TITVYA | | VTDKSDTYKYDDPIS | | | 104 |
| T14.24 | VSDVPRDLEVVAATP | TSRLISMNRSGLQCR | | YYRITYGETGGNBPV | QKFTVPPWASIATIS | | GLKPGVDY-TITVYA | | VTDQRDTYRYDDPIS | | | 105 |
| T14.20 | VSDVPRDLEVVAATP | TSRLISWNYPIAR | | YYRITYGETGGNSPV | QKFTVPPWASIATIS | | GLKPGADY-TITVYA | | VTDKDTYKYDDPIS | | | 106 |
| T14.19 | VSDVPRDLEVVAATA | TEQLISMWFBXPTR | | YYRITYGETBONSPV | QKFTVPPWASPATIS | | GIKPGVDY-TLAVYA | | VTMPB--RKYDKPIS | | | 107 |
| T14.11 | VBDVBRDLEAVAATP | TSLLISWNNFAR5PAR | | YYRITYGETGGNSPV | QKFTVPPWASIATIO | | GLKPRVDY-TITVYA | | VTAQTGHHLHDKSIP | | | 108 |
| T14.10 | VSDVPRDLEVVAATP | TSRLISWRPGRTYSR | | YYRITYGETGGNSPV | QKFTVPPWANTATIS | | GLKPGVDY-TITVYA | | VTFPPGYPLTEMPIS | | | 109 |
| T14.22 | VSDVPRDLEVVAATP | SSRLISWRPGRTYSR | | YYRITYGETGGNBPV | QKFTVPPWANTATIS | | GLKPGVDY-TLAVYA | | VTFPYGYPLTEMPIS | | | 110 |
| T14.21 | VSDVPRDLEVVAATP | TSRLISWRPGRTYBR | | YYRITYGETGGNSPV | QKFTVPPWGSIATIS | | GLKPGVKY-TITVYA | | VTYTHSTPMQDEPIS | | | 111 |
| T14.01 | VSDVPRDLEVVAATP | TSRLISNDBSRPNTR | | YYRITYGETGGNSPV | QKFTVPRFWWI--S | | GLKPGVRY-TITVYA | | VTSECHKLSSTSIS | | | 112 |
| T14.06 | VSDVPRDLEVVAATP | TSLLISWTNASTR | | YYRITYGETGGNSPV | QKFTVPRFWWI--S | | GLKPGVGY-TVTVYA | | VASPDSTSAYSEPIS | | | 113 |
| T14.08 | VSXVPRDLEVVAATP | TSKLISWXPAREHDR | | YYRITYGETGGNSPV | QBFTVPPMYGTIATID | | GLKPGVGY-TVTVYA | | VTDNFNSAKAQHP-- | | | 114 |
| T14.02 | VSDVPRDLEVVATP | TSQLISMTPENEVR | | YYRITYGETGGNSPV | QESTVPTGMATATIS | | GLKPGVDY-TITVYA | | VTPHEGHFDLRPPIS | | | 115 |
| T14.15 | VSDVPRDLEVVAATS | TGLLISWCTPASFHG | | YYRITYGETGGNSPV | EKFTVPLLNWPTATIS | | GLKPGVDY-TITVYA | | VTPTBMLKPQSMPIS | | | 116 |

FIG. 25D

Round M12 (24)

| | 1 | 15 | 16 BC DAPAVTV3031 | 45 | 46 DE GSKB | 60 | 61 | 75 | 76 FG GRGDSPASSK | 90 | | SEQ.ID.NO. |
|---|---|---|---|---|---|---|---|---|---|---|---|---|
| WT | VSDVPRDLEVVAATP | TSLLISWDAPAVTVR | YRRITYGETGGNBPV | QEFTVPGSKSTATIS | GLKPGVDY-TITVYA | VTGRGDSPASSKPIS | INYRT | 33 |
| M12.05 | VSDVPRDLEVVAATP | TSLLISWSPNDAHR | YRRITYGKTGDSPV | QEFTVPGSKSTATIS | GLKPGVDY-TSVVYA | VTDQQSYTYYSNPIS | INYRT | 117 |
| M12.17 | VSDVPSDLEVVAATP | TSLLISWEQSPTKGR | YRRITYGETGGNBPV | QEFTVPGSKSTATIS | GRKPGADY-TITVYA | VTIEKDRIPLFGPIS | ISYRT | 118 |
| M12.12 | VSDVPSDLEVVAATP | TSLLISWEQSPTYGR | YRRITYGETGGNBPV | QEFTVPGSKSTATIS | GRKPGADY-TITVYA | VTIEKDRIPLFGPIS | ISYRT | 119 |
| M12.17 | VSDVPSDLEVVAATP | TSLLISWEQSPTKGR | YRRITYGETGGNBPV | QEFTVPGSKSTATIS | GRKPGADY-TITVYA | VTIEKDRIPLFGPIS | ISYRT | 120 |
| M12.06 | VPDVPRDLEVVAATP | TSLLISWDTENAYNG | YRRITYGETGGSBPA | QEFTVPHPEVTATIS | GLKPGVDD-TITVYA | VTIHHMPLRIFGPIS | ISYRT | 121 |
| M12.01 | VSDVPRDLEVVAATP | TSRLISWNNRSGLQSR | YRRITYGETGGNBPV | QEFTVPPMASIATIS | GLKPGVDY-TITVYA | VTDESDTYKYDDPVS | INYRT | 122 |
| M12.01 | VSDVPRDLEVVAATP | TSRLISWNNRSGLQSR | YRRITYGETGGNBPV | QEFTVPPMASIATIS | GLKPGVDY-TITVYA | VTDESDTYKYDDPVS | TNYRT | 123 |
| M12.24 | VBDVPRDLEVVAATP | TSRLISWNRSGLQSG | YRRITYGETGGNSPV | QEFTVPPMASIATIS | GLKPGVDY-TITVYA | VTPNVGRLDTRYPIS | IDCRT | 124 |
| M12.25 | VBDVPRDLEVVAATP | TSRLISWNRSGLQSR | YRRITYGETGGNBPV | QEFTVPPMASIATIS | GLKPGVDY-TITVYA | VTSNVGRLDTRYPIS | INYRT | 125 |
| M12.23 | VSDVPRDLEVVAATP | TSRLISWRTMFVTAR | YRRITYGETGGDSPV | QEFTVPPMASIAAIS | GLKPGADY-TITVYA | XTSATPSRPMVHPIS | INLTT | 126 |
| M12.04 | VSDVPGDLEVVAATP | TSLLIGWSMTPNWPR | YRLAYGETGGDSPV | QEFTVPPMASIAIIG | GLKPGVDY-TITVYA | VTHRDT-----PIS | INYRT | 127 |
| M12.03 | VSDVPRDLEVVAATP | ISQLTSWQPQPNGSR | YRLAYGETGGNBPV | REFTVPAREQTAT-S | GLKPGVDX-ALTVYA | ATHGKPPHIHFT--- | INYRT | 128 |
| M12.07 | VXDVPRDLKVVXATP | TSLLISXRBGKRTTR | YRRITYGDTGGNBPV | QEFTMPPAATVAAIS | GLKPGVDY-TITVYA | VTVHNSTAQPEYPIP | FNRRT | 129 |
| M12.13 | VSDVPRDLEVVAATP | TBRLISWRPGRTYBR | YRRITYGETGGNSPV | QEFTVPPWANTATIS | CLKPGVDY-TITVYA | VAPPGYPLTEMPIS | INYRT | 130 |
| M12.09 | VSDVPRDLEVVAATP | TSRLISWRPGRAYBR | YFRITYGETGGNBPV | QEFTVPPMASIATIS | GLKPGVDY-TIAVYA | VTFPPRYPLTEMPIS | INYRA | 131 |
| M12.16 | VSDVPRDLRVVAATP | TSRLISWRPGRTYSR | YRRITYGBAGGNSPV | QEFTVPPWASIATIG | GLKPGVDY-TVTVYA | VTDKSGTYRYDDPIS | INYRT | 132 |
| M12.22 | VSDVPRDLEVVAATP | TSRLISWRPASSNPAR | YRRITYGETGGNSPV | QEFTVPPWASVATIG | GLKPGVDY-TVTVYA | VTACTGHRLHDKPIS | INYRT | 133 |
| M12.26 | VSDVPRDLEVVAATP | -SLLISWRNAKDPGR | YRRITYGETGGNBPV | QEFTVPWGTVAFVN | GLKPGVGY-TITVYA | VTHRDT-----PIS | INYRA | 134 |
| M12.15 | VSDVPRDLGLKIVAATP | -SLLISWRNAKDPGR | YRRITYGETGGSBPV | QEFTVPWGTIAAIN | GLKPGVDY-TITVYA | VTATNPGPTQHRPIP | INYRT | 135 |
| M12.18 | VSDVPRDLEVVAADP | HQPLICSASPFMACR | YRRITYGSSGGNSPV | QEFTVPWRATAAAIS | GLKPGVDY-TITVHA | VTDESWSDRSMDPIS | INYRT | 136 |
| M12.14 | VSDVPRDLKVVAATP | TBRLISWTHDNVPAR | YRRITYGETGGNSPV | QELTVPPMATIATIS | GLKPGVDY-TITVYA | VTLYTGNHRPEHPIS | INCRT | 137 |
| M12.21 | VSDVPRDPVVVAATP | TSLLISWYRHTYRDR | YRRVTYGETRGNBPI | REFTVPPMATATIS | GLKPGVDY-TIAVYA | VTDAGYDVHTKRPIS | IN-RT | 138 |
| M12.19 | TGLLISWRNHQYTPR | HYGITYGETGGKSFV | QEFTVPELNPTATIS | RLKPGVDY-TITVYA | VQNGTPRVIYGPIS | INYRT | 139 |
| M12.08 | VSDVPRDLEVVAATP | TSLLNVP-----LIR | YYRITYGETGGNBPV | QEFTVPAPFALATTS | GLKPGVDY-TITVYG | VTSHRNHFHVETPIS | INYQA | 140 |

US 7,115,396 B2

PROTEIN SCAFFOLDS FOR ANTIBODY MIMICS AND OTHER BINDING PROTEINS

CROSS REFERENCE TO RELATED APPLICATIONS

This application is a continuation application of U.S. Ser. No. 09/688,566, filed Oct. 16, 2000, now abandoned which is a continuation-in-part application of U.S. Ser. No. 09/515,260, filed Feb. 29, 2000, now U.S. Pat No. 6,818,418 which is a continuation-in-part application of U.S. Ser. No. 09/456,693, filed Dec. 9, 1999, now abandoned which claim benefit of provisional application U.S. Ser. No. 60/111,737, filed Dec. 10, 1998.

BACKGROUND OF THE INVENTION

This invention relates to protein scaffolds useful, for example, for the generation of products having novel binding characteristics.

Proteins having relatively defined three-dimensional structures, commonly referred to as protein scaffolds, may be used as reagents for the design of engineered products. These scaffolds typically contain one or more regions which are amenable to specific or random sequence variation, and such sequence randomization is often carried out to produce libraries of proteins from which desired products may be selected. One particular area in which such scaffolds are useful is the field of antibody design.

A number of previous approaches to the manipulation of the mammalian immune system to obtain reagents or drugs have been attempted. These have included injecting animals with antigens of interest to obtain mixtures of polyclonal antibodies reactive against specific antigens, production of monoclonal antibodies in hybridoma cell culture (Koehler and Milstein, Nature 256:495, 1975), modification of existing monoclonal antibodies to obtain new or optimized recognition properties, creation of novel antibody fragments with desirable binding characteristics, and randomization of single chain antibodies (created by connecting the variable regions of the heavy and light chains of antibody molecules with a flexible peptide linker) followed by selection for antigen binding by phage display (Clackson et al., Nature 352:624, 1991).

In addition, several non-immunoglobulin protein scaffolds have been proposed for obtaining proteins with novel binding properties. For example, a "minibody" scaffold, which is related to the immunoglobulin fold, has been designed by deleting three beta strands from a heavy chain variable domain of a monoclonal antibody (Tramontano et al., J. Mol. Recognit. 7:9, 1994). This protein includes 61 residues and can be used to present two hypervariable loops. These two loops have been randomized and products selected for antigen binding, but thus far the framework appears to have somewhat limited utility due to solubility problems. Another framework used to display loops has been tendamistat, a 74 residue, six-strand beta sheet sandwich held together by two disulfide bonds (McConnell and Hoess, J. Mol. Biol. 250:460, 1995). This scaffold includes three loops, but, to date, only two of these loops have been examined for randomization potential.

Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164:243, 1995; Wang et al., J. Biol. Chem. 270:12250, 1995).

SUMMARY OF THE INVENTION

The present invention provides a new family of proteins capable of evolving to bind any compound of interest. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies.

These antibody mimics may be utilized for the purpose of designing proteins which are capable of binding to virtually any compound (for example, any protein) of interest. For example, the $^{10}$Fn3-based molecules described herein may be used as scaffolds which are subjected to directed evolution to form a population with one or more randomized Fn3 loops that are analogous by position and structure to the complementarity-determining regions (CDRs) of an antibody variable region, and/or to randomize Fn3's other three solvent exposed loops. Such a directed evolution approach results in the production of antibody-like molecules with high affinities for antigens of interest. In addition, the scaffolds described herein may be used to display defined exposed loops (for example, loops previously randomized and selected on the basis of antigen binding) in order to direct the evolution of molecules that bind to such introduced loops. A selection of this type may be carried out to identify recognition molecules for any individual CDR-like loop or, alternatively, for the recognition of two or all three CDR-like loops combined into a non-linear epitope.

Accordingly, in a first aspect, the present invention features randomized or mutated scaffold proteins. In particular, the invention features a non-antibody protein including a domain having an immunoglobulin-like fold, the non-antibody protein deriving from a reference protein by having a mutated amino acid sequence, wherein the non-antibody protein binds with a Kd at least as tight as 1 μM to a compound that is not bound as tightly by the reference protein.

In addition, the invention features a non-antibody protein deriving from a scaffold protein including a domain having an immunoglobulin-like fold, wherein the amino acid sequence of the domain in the derived protein is more than 50% identical to the amino acid sequence of the domain in the scaffold protein.

In yet another embodiment, the invention features a protein that includes a fibronectin type III domain having at least one randomized loop, the protein being characterized by the ability of the Fn3 domain to bind to a compound that is not bound by the corresponding naturally-occurring Fn3 domain.

In various preferred embodiments, any of these proteins of the invention bind to their target compounds with a Kd at least as tight as 500 nM, preferably, with a Kd at least as tight as 100 nM or 10 nM, and, more preferably, with a Kd at least as tight as 1 nM, 500 pM, 100 pM, or even 20 pM. The protein preferably contains one, two, or three mutated loops and at least one of the loops, and preferably two or all three of the loops, contributes to the binding of the protein to the compound. Additionally, the reference protein preferably lacks disulfide bonds, and the derivative protein may have at least one disulfide bond.

With respect to certain embodiments, the domain having an immunoglobulin-like fold preferably has a molecular mass less than 10 kD or greater than 7.5 kD, and, more preferably, has a molecular mass between 7.5–10 kD. The proteins of the invention may be monomers under physiological conditions or may be multimers, for example, dimers. In other preferred embodiments, the reference protein used to derive a mutated protein of the invention is a naturally-occurring mammalian protein (for example, a human protein); and the domain having an immunoglobulin-like fold is mutated and includes up to 50%, and preferably up to 34%, mutated amino acids as compared to the immunoglobulin-like fold of the reference protein. In addition, the domain having the immunoglobulin-like fold preferably consists of approximately 50–150 amino acids, and more preferably consists of approximately 50 amino acids.

Derivative proteins of the invention may be derived from any appropriate reference protein including, but not limited to, the preferred proteins, fibronectin or a fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

In further preferred embodiments of Fn3 domain-containing proteins, the fibronectin type III domain is a mammalian (for example, a human) fibronectin type III domain; and the protein includes the tenth module of the fibronectin type III ($^{10}$Fn3) domain. In such proteins, compound binding is preferably mediated by either one, two, or three $^{10}$Fn3 loops. In other preferred embodiments, the second (DE) loop of $^{10}$Fn3 may be extended in length relative to the naturally-occurring module, or the $^{10}$Fn3 may lack an integrin-binding motif. In these molecules, the integrin-binding motif may be replaced by an amino acid sequence in which a polar amino acid-neutral amino acid-acidic amino acid sequence (in the N-terminal to C-terminal direction) replaces the integrin-binding motif; alternatively, one preferred sequence is serine-glycine-glutamate. In another preferred embodiment, the fibronectin type III domain-containing proteins of the invention lack disulfide bonds.

Any of the proteins of the invention (for example, the fibronectin type III domain-containing proteins) may be formulated as part of a fusion protein. If the fusion protein is to be used for compound binding or compound binding selections, the fusion protein includes a heterologous protein that does not itself bind to the compound of interest. The heterologous protein may, for example, be an antibody or antibody domain (such as an immunoglobulin $F_c$ domain), a complement protein, a toxin protein, or an albumin protein. In addition, any of the proteins of the invention (for example, the fibronectin type III domain proteins) may be covalently bound to a nucleic acid (for example, an RNA), and the nucleic acid may encode the protein. Moreover, the protein may be a multimer, or, particularly if it lacks an integrin-binding motif, it may be formulated in a physiologically-acceptable carrier.

The present invention also features proteins that include a fibronectin type III domain having at least one mutation in a β-sheet sequence. Again, these proteins are characterized by their ability to bind to compounds that are not bound or are not bound as tightly by the corresponding naturally-occurring fibronectin domain.

Any of the proteins of the invention may be immobilized on a solid support (for example, a bead or chip), and these proteins may be arranged in any configuration on the solid support, including an array.

In a related aspect, the invention further features nucleic acids encoding any of the proteins of the invention. In preferred embodiments, the nucleic acid is DNA or RNA.

In another related aspect, the invention also features a method for generating a protein which includes a fibronectin type III domain and which is pharmaceutically acceptable to a mammal, involving removing the integrin-binding domain of said fibronectin type III domain. This method may be applied to any of the fibronectin type III domain-containing proteins described above and is particularly useful for generating proteins for human therapeutic applications. The invention also features such fibronectin type III domain-containing proteins which lack integrin-binding domains.

In yet another related aspect, the invention features methods of obtaining derivative non-antibody proteins which bind to compounds of interest. One such method involves: (a) providing a non-antibody scaffold protein including an immunoglobulin-like fold, wherein the scaffold protein does not bind to the compound with a Kd as tight as 1 µM; (b) generating mutated derivatives of the non-antibody scaffold protein, thereby producing a library of mutated proteins; (c) contacting the library with the compound; (d) selecting from the library at least one derivative protein which binds to the compound with a Kd at least as tight as 1 µM; and (e) optionally repeating steps (b)–(d) substituting for the non-antibody scaffold protein in repeated step (b) the product from the previous step (d). This technique may also be carried out with any of the proteins of the invention (for example, any of the fibronectin type III domain-containing proteins).

In yet other related aspects, the invention features screening methods which may be used to obtain or evolve randomized or mutated proteins of the invention capable of binding to compounds of interest, or to obtain or evolve compounds (for example, proteins) capable of binding to a particular protein containing a randomized or mutated motif. In addition, the invention features screening procedures which combine these two methods, in any order, to obtain either compounds or proteins of interest.

In particular, a first screening method, useful for the isolation or identification of randomized or mutated proteins of interest, involves: (a) contacting a compound of interest with a candidate protein, the candidate protein being a derivative non-antibody protein including a domain having an immunoglobulin-like fold, the non-antibody protein deriving from a reference protein by having a mutated amino acid sequence wherein the non-antibody protein binds with a Kd at least as tight as 1 µM to a compound that is not bound as tightly by the reference protein, wherein the contacting is carried out under conditions that allow compound-protein complex formation; and (b) obtaining, from the complex, the derivative protein that binds to the compound. This general technique may also be carried out with a fibronectin type III domain protein having at least one randomized or mutated loop.

The second screening method is for isolating or identifying a compound which binds to a protein of the invention. This method begins with a non-antibody protein including a domain having an immunoglobulin-like fold and deriving from a reference protein by having a mutated amino acid sequence, wherein the non-antibody protein binds with a Kd at least as tight as 1 µM to a compound that is not bound as tightly by the reference protein. This derivative protein is then contacted with a candidate compound, wherein the contacting is carried out under conditions that allow compound-protein complex formation, and the compound which binds to the derivative protein is obtained from the complex. Again, this general technique may be carried out with any protein of the invention, for example, a protein with a mutated fibronectin type III domain.

In addition, the invention features diagnostic methods which employ the proteins of the invention (for example, fibronectin type III scaffold proteins and their derivatives). Such diagnostic methods may be carried out on a sample (for example, a biological sample) to detect one analyte or to simultaneously detect many different analytes in the sample. The method may employ any of the scaffold molecules described herein. Preferably, the method involves (a) contacting the sample with a protein of the invention that binds to the compound analyte, the contacting being carried out under conditions that allow compound-protein complex formation; and (b) detecting the complex, and therefore the compound in the sample. In addition, this method may be used to quantitate, as well as detect, compound levels in a sample.

In preferred embodiments of any of the selection or diagnostic methods described herein, the protein of the invention binds to its target compound with a Kd at least as tight as 1 µM or 500 nM, preferably, with a Kd at least as tight as 100 nM or 10 nM, and, more preferably, with a Kd at least as tight as 1 nM, 500 pM, 100 pM, or even 20 pM. The protein preferably contains one, two, or three mutated loops and at least one of the loops, and preferably two or all three of the loops contributes to the binding of the protein to the compound. Additionally, the reference protein preferably lacks disulfide bonds, and the derivative protein may have at least one disulfide bond.

With respect to certain embodiments of the methods, the domain having an immunoglobulin-like fold preferably has a molecular mass less than 10 kD or greater than 7.5 kD, and, more preferably, has a molecular mass between 7.5–10 kD. The proteins of the invention may be monomers under physiological conditions or may be multimers, for example, dimers. In other preferred embodiments, the reference protein used to derive a mutated protein of the invention is a naturally-occurring mammalian protein (for example, a human protein); and the domain having an immunoglobulin-like fold is mutated and includes up to 50%, and preferably up to 34%, mutated amino acids as compared to the immunoglobulin-like fold of the reference protein. In addition, the domain having an immunoglobulin-like fold preferably consists of approximately 50–150 amino acids, and more preferably consists of approximately 50 amino acids.

Derivative proteins used in the methods of the invention may be derived from any appropriate reference protein including, but not limited to, the preferred proteins, fibronectin or a fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

In addition, the steps of the selection methods described herein may be repeated with further mutation or randomization being carried out between cycles. For example, for the methods involving a protein having a mutated or randomized fibronectin type III domain, at least one loop of the fibronectin type III domain of the protein obtained in step (b) may be mutated and steps (a) and (b) repeated using the further randomized protein, or the compound obtained in step (b) may be modified and steps (a) and (b) repeated using the further modified compound. In these methods, the compound is preferably a protein, and the fibronectin type III domain is preferably a mammalian (for example, a human) fibronectin type III domain. In other preferred embodiments, the protein includes the tenth module of the fibronectin type III domain ($^{10}$Fn3), and binding is mediated by one, two, or three $^{10}$Fn3 loops. In addition, the second (DE) loop of $^{10}$Fn3 may be extended in length relative to the naturally-occurring module, or $^{10}$Fn3 may lack an integrin-binding motif. Again, as described above, the integrin-binding motif may be replaced by an amino acid sequence in which a basic amino acid-neutral amino acid-acidic amino acid sequence (in the N-terminal to C-terminal direction) replaces the integrin-binding motif; alternatively, one preferred replacement sequence is serine-glycine-glutamate.

The selection and diagnostic methods described herein may be carried out using any of the proteins of the invention (for example, a fibronectin type III domain-containing protein). In addition, any of these proteins may be formulated as part of a fusion protein with a heterologous protein (for example, an antibody or antibody domain (including an immunoglobulin $F_c$ domain) that does not itself bind the compound of interest, or a complement protein, toxin protein, or albumin protein). In addition, selections and diagnostic methods may be carried out using the proteins of the invention (for example, the fibronectin type III domain proteins) covalently bound to nucleic acids (for example, RNAs or any nucleic acid which encodes the protein). Moreover, the selections and diagnostic methods may be carried out using these proteins (for example, the fibronectin domain-containing proteins) as monomers or as multimers, such as dimers.

Preferably, the selections and diagnostic methods involve the immobilization of the binding target on a solid support. Preferred solid supports include columns (for example, affinity columns, such as agarose-based affinity columns), microchips, or beads. Alternatively, the proteins (for example, the Fn3 domain-containing proteins) may be immobilized and contacted with one or more potential binding targets.

For the diagnostic methods, the compound is often a protein, but may also be any other analyte in a sample. Detection may be accomplished by any standard technique including, without limitation, radiography, fluorescence detection, mass spectroscopy, or surface plasmon resonance.

In a final aspect, the invention features a non-antibody protein that binds tumor necrosis factor-α (TNF-α) with a Kd at least as tight as 1 μM, the protein having a sequence that is less than 20% identical to TNF-α receptor (for example, a naturally-occurring TNF-α receptor, such as a mammalian or human TNF-α receptor).

In preferred embodiments, this protein includes a mutated fibronectin type III domain and the protein is mutated in the DE, BC, and FG loops. Preferably, the mutated FG loop is the same length as the wild-type FG loop. In other preferred embodiments, the protein includes an immunoglobulin-like fold (preferably, having a molecular mass less than 10 kD, greater than 7.5 kD, or between 7.5–10 kD) that consists of approximately 50–150 amino acids, and preferably, approximately 50 amino acids.

The TNF-α binders according to the invention bind TNF-α with a Kd at least as tight as 1 μM, preferably, at least as tight as 500 nM, 100 nM, or 10 nM, more preferably, at least as tight as 1 nM or 500 pM, and, most preferably, at least as tight as 100 pM or even 20 pM. Preferably, these proteins contain one, two, or three mutated loops, and at least one, and preferably two or all three of the loops, contribute to the binding of the non-antibody protein to TNF-α. In other preferred embodiments, the non-antibody protein has at least one disulfide bond, and the non-antibody protein is a monomer or dimer under physiological conditions.

The TNF-α binders may be immobilized on a solid support (for example, a chip or bead), and may be part of an array. In addition, any of the TNF-α binders may be joined to a heterologous protein (for example, a heterologous protein that is an antibody or an antibody domain that does not bind TNF-α, an immunoglobulin $F_c$ domain, a complement protein, or an albumin protein).

If desired, the protein may include a mutated fibronectin type III domain (for example, one derived from a human fibronectin type III domain, such as a mutated tenth module of the fibronectin type III domain ($^{10}$Fn3)). In addition, the protein may lack an $^{10}$Fn3 integrin-binding motif. TNF-α binders preferably include a non-naturally occurring sequence in a loop of $^{10}$Fn3 (for example, the loop sequence PW(A/G), and may include a non-naturally occurring sequence in a α-sheet of $^{10}$Fn3. Particularly preferred TNF-α binders of the invention are shown in FIG. 25 (SEQ ID NOS: 34–140).

In addition, in related aspects, the invention features nucleic acids encoding any of the TNF-α binding proteins of the invention, as well as a loop structure on any protein that includes any one of the amino acid sequences of FIG. 25 (SEQ ID NOS: 34–140).

As used herein, by "non-antibody protein" is meant a protein that is not produced by the B cells of a mammal either naturally or following immunization of a mammal. This term also excludes antibody fragments of more than 100 amino acids, preferably, more than 80 amino acids, and, most preferably, more than 50 amino acids in length.

By "immunoglobulin-like fold" is meant a protein domain of between about 80–150 amino acid residues that includes two layers of antiparallel beta-sheets, and in which the flat, hydrophobic faces of the two beta-sheets are packed against each other. Proteins according to the invention may include several immunoglobulin-like folds covalently bound or associated non-covalently into larger structures.

By "scaffold" is meant a protein used to select or design a protein framework with specific and favorable properties, such as binding. When designing proteins from the scaffold, amino acid residues that are important for the framework's favorable properties are retained, while others residues may be varied. Such a scaffold has less than 50% of the amino acid residues that vary between protein derivatives having different properties and greater than or equal to 50% of the residues that are constant between such derivatives. Most commonly, these constant residues confer the same overall three-dimensional fold to all the variant domains, regardless of their properties.

By "fibronectin type III domain" is meant a domain having 7 or 8 beta strands which are distributed between two beta sheets, which themselves pack against each other to form the core of the protein, and further containing loops which connect the beta strands to each other and are solvent exposed. There are at least three such loops at each edge of the beta sheet sandwich, where the edge is the boundary of the protein perpendicular to the direction of the beta strands. Preferably, a fibronectin type III domain includes a sequence which exhibits at least 30% amino acid identity, and preferably at least 50% amino acid identity, to the sequence encoding the structure of the $^{10}$Fn3 domain referred to as "1ttg" (ID="1ttg" (one ttg)) available from the RCSB (Research Collaboratory for Structural Bioinformatics) Protein Data Base. Sequence identity referred to in this definition is determined by the Homology program, available from Molecular Simulation (San Diego, Calif.). The invention further includes polymers of $^{10}$Fn3-related molecules, which are an extension of the use of the monomer structure, whether or not the subunits of the polyprotein are identical.

By "naturally occurring" is meant any protein that is encoded by a living organism.

By "randomized" or "mutated" is meant including one or more amino acid alterations relative to a template sequence. By "randomizing" or "mutating" is meant the process of introducing, into a sequence, such an amino acid alteration. Randomization or mutation may be accomplished through intentional, blind, or spontaneous sequence variation, generally of a nucleic acid coding sequence, and may occur by any technique, for example, PCR, error-prone PCR, or chemical DNA synthesis. By a "corresponding, non-mutated protein" is meant a protein that is identical in sequence, except for the introduced amino acid mutations.

By a "protein" is meant any sequence of two or more amino acids, regardless of length, post-translation modification, or function. "Protein" and "peptide" are used interchangeably herein.

By "RNA" is meant a sequence of two or more covalently bonded, naturally occurring or modified ribonucleotides. One example of a modified RNA included within this term is phosphorothioate RNA.

By "DNA" is meant a sequence of two or more covalently bonded, naturally occurring or modified deoxyribonucleotides.

By a "nucleic acid" is meant any two or more covalently bonded nucleotides or nucleotide analogs or derivatives. As used herein, this term includes, without limitation, DNA, RNA, and PNA.

By "pharmaceutically acceptable" is meant a compound or protein that may be administered to an animal (for example, a mammal) without significant adverse medical consequences.

By "physiologically acceptable carrier" is meant a carrier which does not have a significant detrimental impact on the treated host and which retains the therapeutic properties of the compound with which it is administered. One exemplary physiologically acceptable carrier is physiological saline. Other physiologically acceptable carriers and their formulations are known to one skilled in the art and are described, for example, in Remington's Pharmaceutical Sciences, (18$^{th}$ edition), ed. A. Gennaro, 1990, Mack Publishing Company, Easton, Pa., incorporated herein by reference.

By a "fusion protein" is meant a protein that includes (i) a scaffold protein of the invention joined to (ii) a second, different (i.e., "heterologous") protein. "Fusion proteins" are distinguished from "nucleic acid-protein fusions" and "RNA-protein fusions" in that a "fusion protein" is composed entirely of amino acids, while both a "nucleic acid-protein fusion" and an "RNA-protein fusion" include a stretch of nucleic acids (the nucleic acid or RNA component) joined to a stretch of amino acids (the protein component).

By "selecting" is meant substantially partitioning a molecule from other molecules in a population. As used herein, a "selecting" step provides at least a 2-fold, preferably, at least a 30-fold, more preferably, at least a 100-fold, and, most preferably, at least a 1000-fold enrichment of a desired molecule relative to undesired molecules in a population following the selection step. A selection step may be repeated any number of times, and different types of selection steps may be combined in a given approach.

By "binding partner," as used herein, is meant any molecule which has a specific, covalent or non-covalent affinity for a portion of a desired compound (for example, protein) of interest. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of another molecule (for example, a compound or protein).

By a "solid support" is meant, without limitation, any column (or column material), bead, test tube, microtiter dish, solid particle (for example, agarose or sepharose), microchip (for example, silicon, silicon-glass, or gold chip), or membrane (for example, an inorganic membrane, nitrocellulose, or the membrane of a liposome or vesicle) to which an antibody mimic or an affinity complex may be bound, either directly or indirectly (for example, through other binding partner intermediates such as other antibodies or Protein A), or in which an antibody mimic or an affinity complex may be embedded (for example, through a receptor or channel).

The present invention provides a number of advantages. For example, as described in more detail below, the present antibody mimics exhibit improved biophysical properties, such as stability under reducing conditions and solubility at high concentrations. In addition, these molecules may be readily expressed and folded in prokaryotic systems, such as E. coli, in eukaryotic systems, such as yeast, and in in vitro translation systems, such as the rabbit reticulocyte lysate system. Moreover, these molecules are extremely amenable to affinity maturation techniques involving multiple cycles of selection, including in vitro selection using RNA-protein fusion technology (Roberts and Szostak, Proc. Natl. Acad. Sci USA 94:12297, 1997; Szostak et al., U.S. Ser. No. 09/007,005 and U.S. Ser. No. 09/247,190; Szostak et al. WO98/31700), phage display (see, for example, Smith and Petrenko, Chem. Rev. 97:317, 1997), and yeast display systems (see, for example, Boder and Wittrup, Nature Biotech. 15:553, 1997).

Other features and advantages of the present invention will be apparent from the following detailed description thereof, and from the claims.

BRIEF DESCRIPTION OF THE DRAWINGS

FIG. 4 is a graph illustrating a sequence alignment between a fibronectin type III protein domain and related protein domains.

FIG. 25 is a graph listing exemplary TNF-α binders (SEQ ID NOS: 33–140) according to the invention.

DETAILED DESCRIPTION

The novel antibody mimics described herein have been designed to be superior both to antibody-derived fragments and to non-antibody frameworks, for example, those frameworks cited above.

The major advantage of these antibody mimics over antibody fragments is structural. These antibody mimics are derived from whole, stable, and soluble structural scaffolds. For example, the Fn3 scaffold is found in the human body. Consequently, they exhibit better folding and thermostability properties than antibody fragments, whose creation involves the removal of parts of the antibody native fold, often exposing amino acid residues that, in an intact antibody, would be buried in a hydrophobic environment, such as an interface between variable and constant domains. Exposure of such hydrophobic residues to solvent increases the likelihood of aggregation of the antibody fragments.

In addition, the scaffolds described herein have no disulfide bonds, which have been reported to retard or prevent proper folding of antibody fragments under certain conditions. Since the present scaffolds do not rely on disulfides for native fold stability, they are stable under reducing conditions, unlike antibodies and their fragments which unravel upon disulfide bond reduction.

Figure 2:
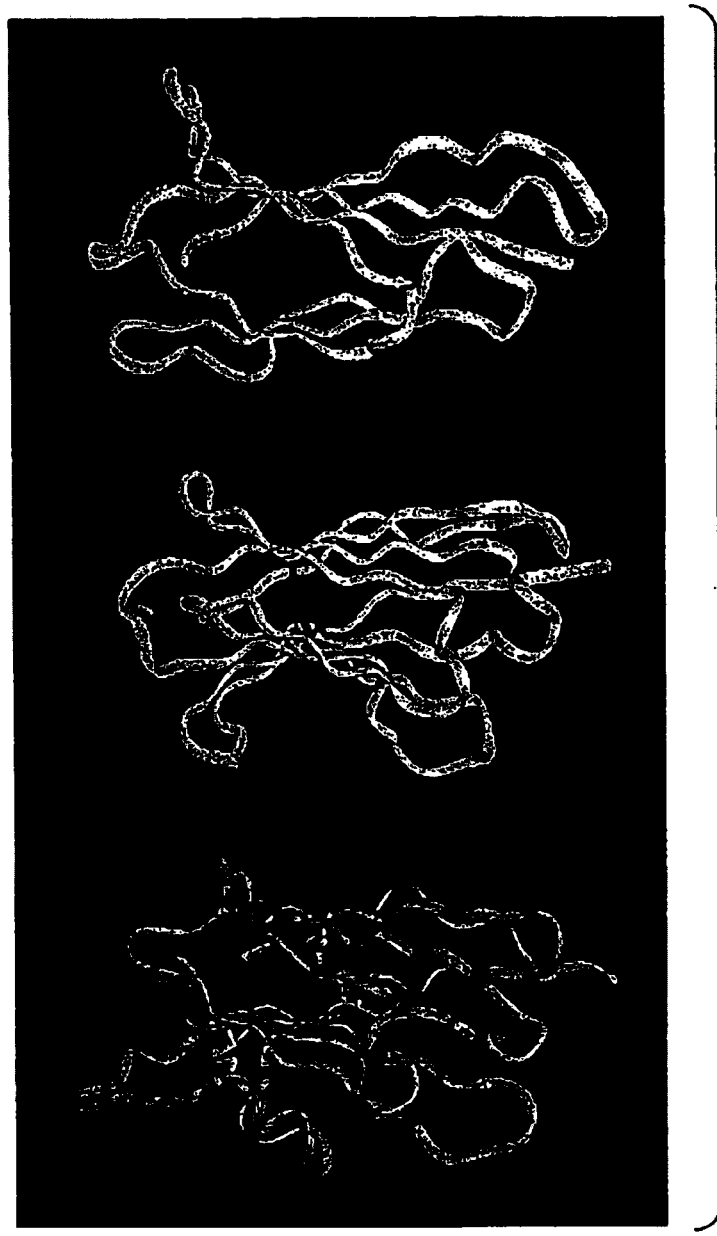
FIG. 2 is a photograph showing a comparison between the structures of the camel antibody heavy chain variable region (dark blue), the llama antibody heavy chain variable region (light blue), and a fibronectin type III module number 10 ($^{10}$Fn3) (yellow).

Moreover, these scaffolds provide the functional advantages of antibody molecules. In particular, despite the fact that the $^{10}$Fn3 module is not an immunoglobulin, its overall fold is close to that of the variable region of the IgG heavy chain (FIG. 2), making it possible to display the three fibronectin loops analogous to CDRs in relative orientations similar to those of native antibodies. Because of this structure, the present antibody mimics possess antigen binding properties that are similar in nature and affinity to those of antibodies, and a loop randomization and shuffling strategy may be employed in vitro that is similar to the process of affinity maturation of antibodies in vivo.

There are now described below exemplary scaffolds, for example, fibronectin-based scaffolds, and their use for identifying, selecting, and evolving novel binding proteins as well as their target ligands. These examples are provided for the purpose of illustrating, and not limiting, the invention.

$^{10}$Fn3 Structural Motif

Figure 1:
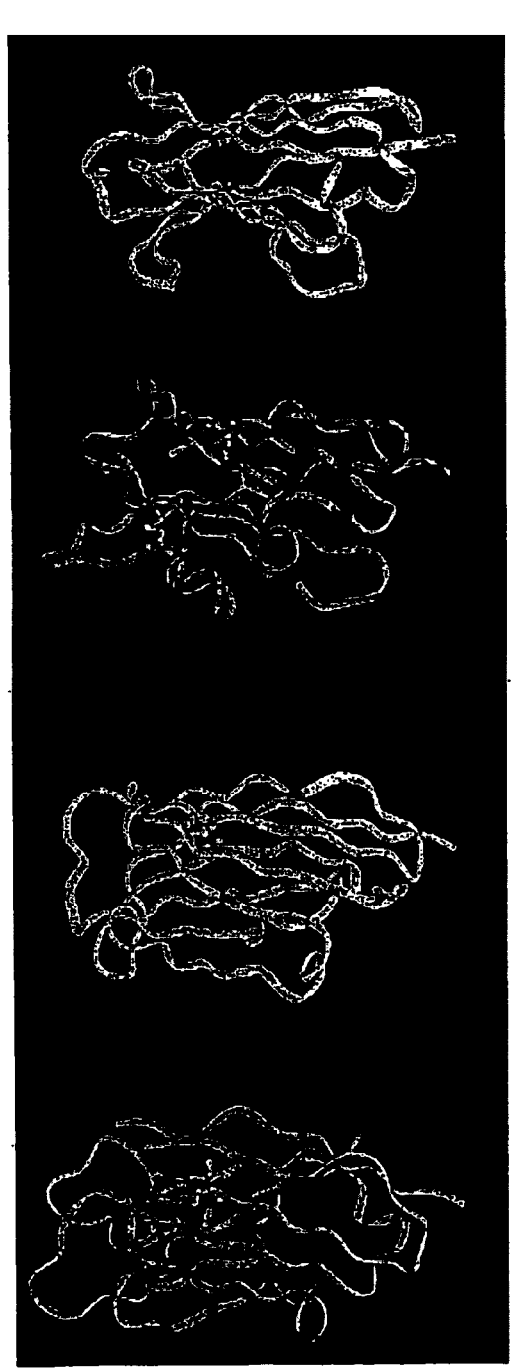
FIG. 1 is a photograph showing a comparison between the structures of antibody heavy chain variable regions from camel (dark blue) and llama (light blue), in each of two orientations.

Preferred antibody mimics of the present invention are based on the structure of a fibronectin module of type III (Fn3), a common domain found in mammalian blood and structural proteins. This domain occurs more than 400 times in the protein sequence database and has been estimated to occur in 2% of the proteins sequenced to date, including fibronectins, tenascin, intracellular cytoskeletal proteins, and prokaryotic enzymes (Bork and Doolittle, Proc. Natl. Acad. Sci. USA 89:8990, 1992; Bork et al., Nature Biotech. 15:553, 1997; Meinke et al., J. Bacteriol. 175:1910, 1993; Watanabe et al., J. Biol. Chem. 265:15659, 1990). A particular scaffold is the tenth module of human Fn3 ($^{10}$Fn3), which comprises 94 amino acid residues. The overall fold of this domain is closely related to that of the smallest functional antibody fragment, the variable region of the heavy chain, which comprises the entire antigen recognition unit in camel and llama IgG (FIG. 1, 2). The major differences between camel and llama domains and the $^{10}$Fn3 domain are that (i) $^{10}$Fn3 has fewer beta strands (seven vs. nine) and (ii) the two beta sheets packed against each other are connected by a disulfide bridge in the camel and llama domains, but not in $^{10}$Fn3.

Figure 3:
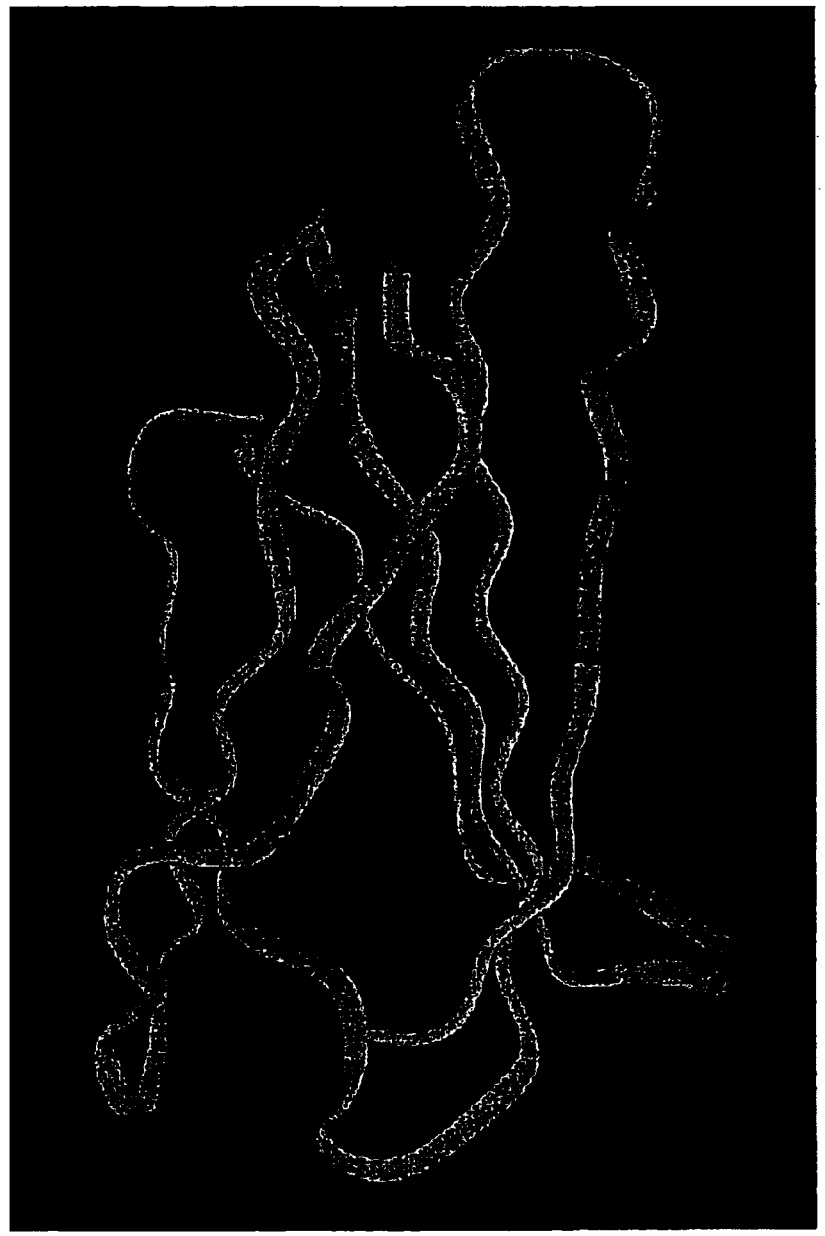
FIG. 3 is a photograph showing a fibronectin type III module number 10 ($^{10}$Fn3), with the loops corresponding to the antigen-binding loops in IgG heavy chains highlighted in red.

The three loops of $^{10}$Fn3 corresponding to the antigen-binding loops of the IgG heavy chain run between amino acid residues 21–31 (BC), 51–56 (DE), and 76–88 (FG) (FIG. 3). The length of the BC and DE loop, 10 and 6 residues, respectively, fall within the narrow range of the corresponding antigen-recognition loops found in antibody heavy chains, that is, 7–10 and 4–8 residues, respectively. Accordingly, once randomized and selected for high antigen affinity, these two loops may make contacts with antigens equivalent to the contacts of the corresponding loops in antibodies.

In contrast, the FG loop of $^{10}$Fn3 is 12 residues long, whereas the corresponding loop in antibody heavy chains ranges from 4–28 residues. To optimize antigen binding, therefore, the length of the FG loop of $^{10}$Fn3 is preferably randomized in length as well as in sequence to cover the CDR3 range of 4–28 residues to obtain the greatest possible flexibility and affinity in antigen binding. Indeed, in general, the lengths as well as the sequences of the CDR-like loops of the antibody mimics may be randomized during in vitro or in vivo affinity maturation (as described in more detail below).

The tenth human fibronectin type III domain, $^{10}$Fn3, refolds rapidly even at low temperature; its backbone conformation has been recovered within 1 second at 5° C. Thermodynamic stability of $^{10}$Fn3 is high ($\Delta G_u$=24 kJ/mol=5.7 kcal/mol), correlating with its high melting temperature of 110° C.

One of the physiological roles of $^{10}$Fn3 is as a subunit of fibronectin, a glycoprotein that exists in a soluble form in body fluids and in an insoluble form in the extracellular matrix (Dickinson et al., J. Mol. Biol. 236:1079, 1994). A fibronectin monomer of 220–250 kD contains 12 type I modules, two type II modules, and 17 fibronectin type III modules (Potts and Campbell, Curr. Opin. Cell Biol. 6:648, 1994). Different type III modules are involved in the binding of fibronectin to integrins, heparin, and chondroitin sulfate. $^{10}$Fn3 was found to mediate cell adhesion through an integrin-binding Arg-Gly-Asp (RGD) motif on one of its exposed loops. Similar RGD motifs have been shown to be involved in integrin binding by other proteins, such as fibrinogen, von Wellebrand factor, and vitronectin (Hynes et al., Cell 69:11, 1992). No other matrix- or cell-binding roles have been described for $^{10}$Fn3.

The observation that $^{10}$Fn3 has only slightly more adhesive activity than a short peptide containing RGD is consistent with the conclusion that the cell-binding activity of $^{10}$Fn3 is localized in the RGD peptide rather than distributed throughout the $^{10}$Fn3 structure (Baron et al., Biochemistry 31:2068, 1992). The fact that $^{10}$Fn3 without the RGD motif is unlikely to bind to other plasma proteins or extracellular matrix makes $^{10}$Fn3 a useful scaffold to replace antibodies. In addition, the presence of $^{10}$Fn3 in natural fibrinogen in the bloodstream suggests that $^{10}$Fn3 itself is unlikely to be immunogenic in the organism of origin.

Figure 5:
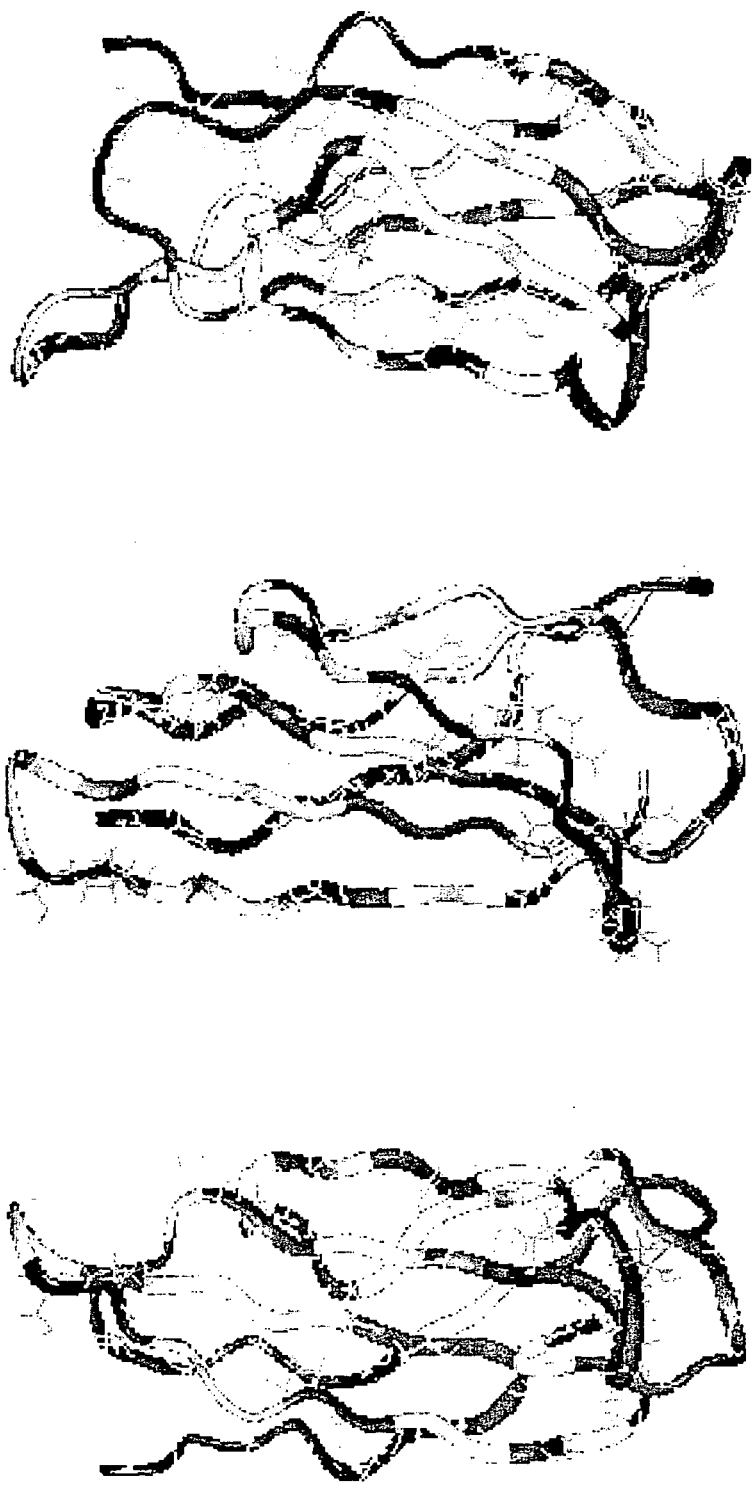
FIG. 5 is a photograph showing the structural similarities between a $^{10}$Fn3 domain and 15 related proteins, including fibronectins, tenascins, collagens, and undulin. In this photograph, the regions are labeled as follows: constant, dark blue; conserved, light blue; neutral, white; variable, red; and RGD integrin-binding motif (variable), yellow.
Figure 6:
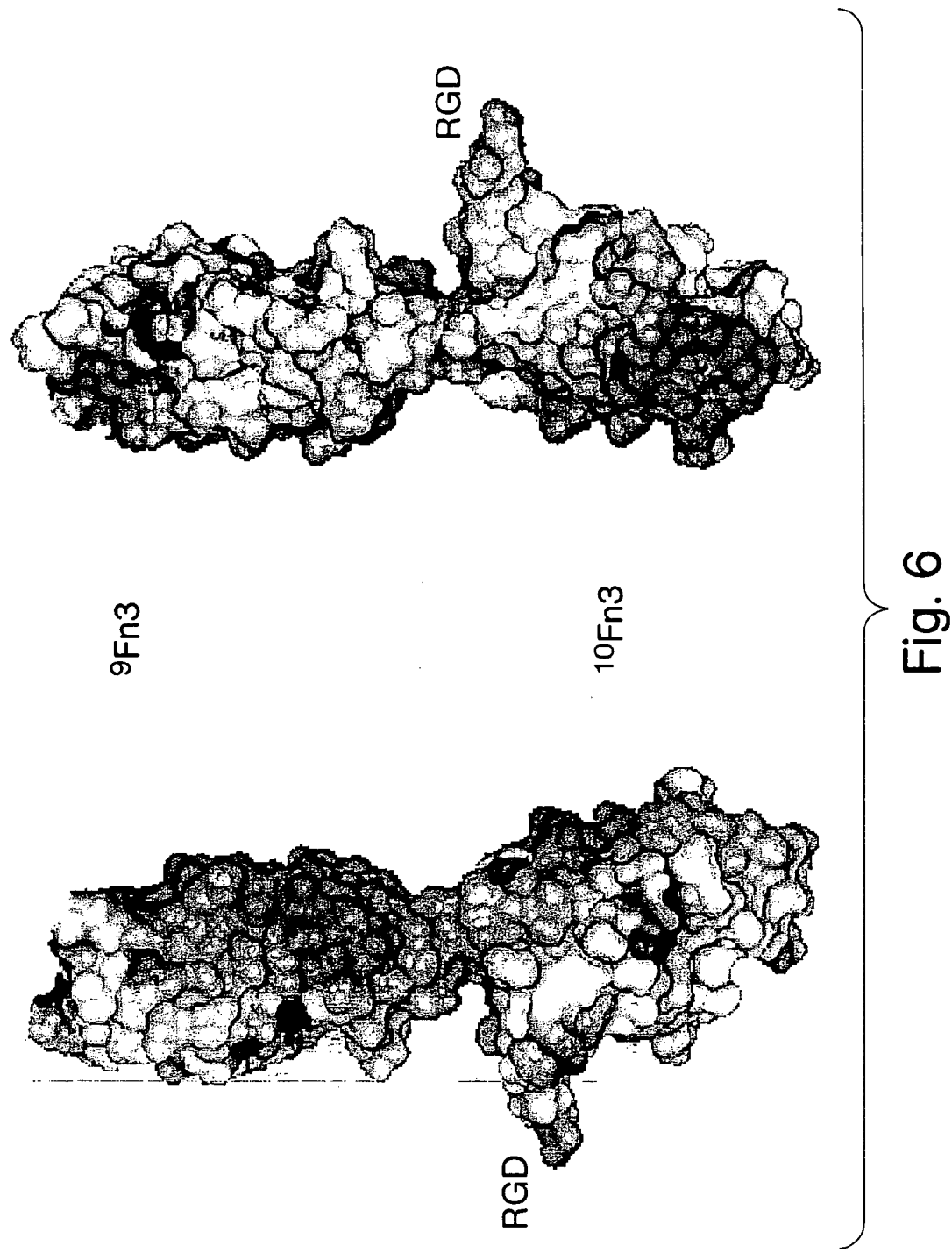
FIG. 6 is a photograph showing space filling models of fibronectin III modules 9 and 10, in each of two different orientations. The two modules and the integrin binding loop (RGD) are labeled. In this figure, blue indicates positively charged residues, red indicates negatively charged residues, and white indicates uncharged residues.
Figure 7:
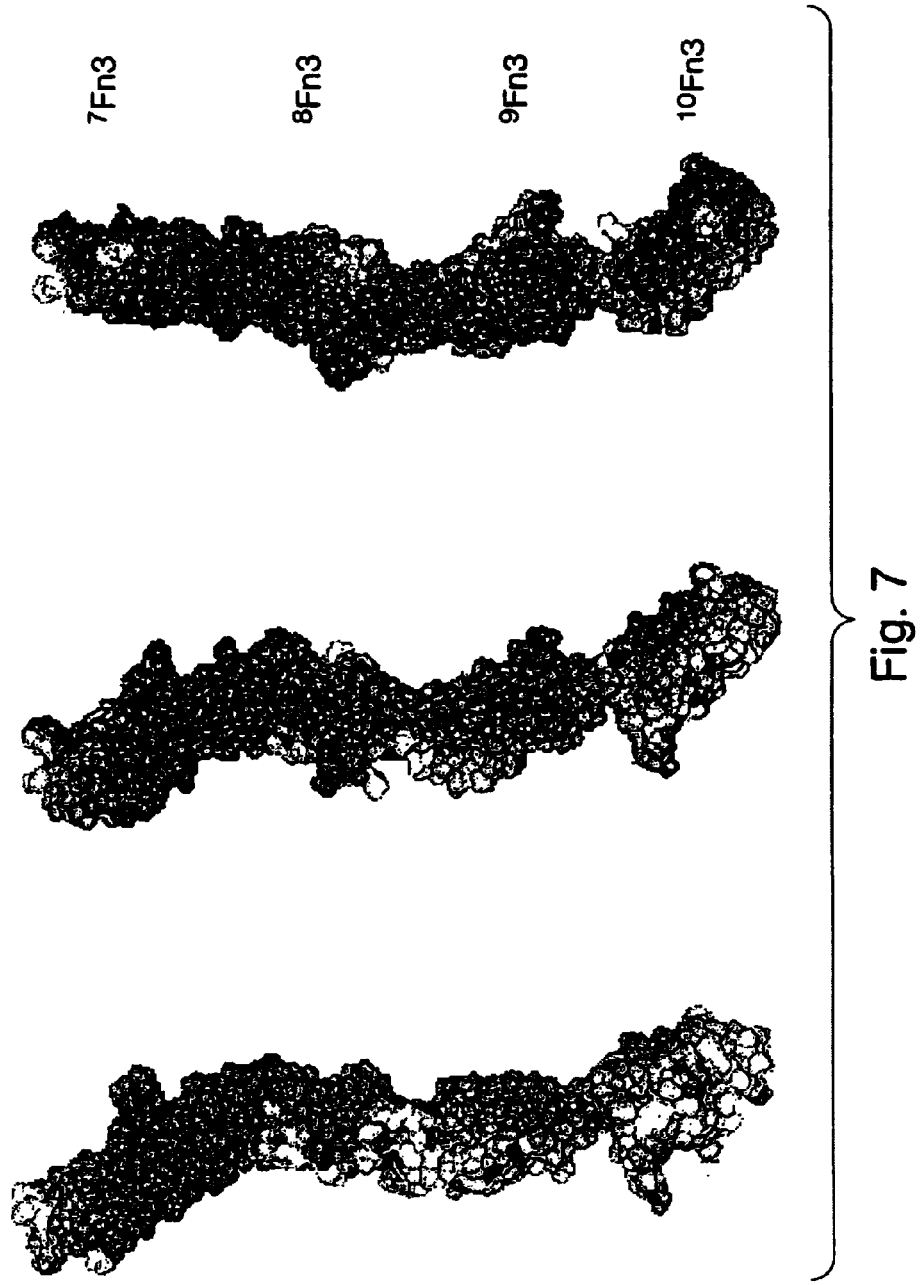
FIG. 7 is a photograph showing space filling models of fibronectin III modules 7–10, in each of three different orientiations. The four modules are labeled. In this figure, blue indicates positively charged residues, red indicates negatively charged residues, and white indicates uncharged residues.

In addition, we have determined that the $^{10}$Fn3 framework possesses exposed loop sequences tolerant of randomization, facilitating the generation of diverse pools of antibody mimics. This determination was made by examining the flexibility of the $^{10}$Fn3 sequence. In particular, the human $^{10}$Fn3 sequence was aligned with the sequences of fibronectins from other sources as well as sequences of related proteins (FIG. 4), and the results of this alignment were mapped onto the three-dimensional structure of the human $^{10}$Fn3 domain (FIG. 5). This alignment revealed that the majority of conserved residues are found in the core of the beta sheet sandwich, whereas the highly variable residues are located along the edges of the beta sheets, including the N- and C-termini, on the solvent-accessible faces of both beta sheets, and on three solvent-accessible loops that serve as the hypervariable loops for affinity maturation of the antibody mimics. In view of these results, the randomization of these three loops are unlikely to have an adverse effect on the overall fold or stability of the $^{10}$Fn3 framework itself.

For the human $^{10}$Fn3 sequence, this analysis indicates that, at a minimum, amino acids 1–9, 44–50, 61–54, 82–94 (edges of beta sheets); 19, 21, 30–46 (even), 79–65 (odd) (solvent-accessible faces of both beta sheets); 21–31, 51–56, 76–88 (CDR-like solvent-accessible loops); and 14–16 and 36–45 (other solvent-accessible loops and beta turns) may be randomized to evolve new or improved compound-binding proteins. In addition, as discussed above, alterations in the lengths of one or more solvent exposed loops may also be included in such directed evolution methods.

Alternatively, changes in the β-sheet sequences may also be used to evolve new proteins. These mutations change the scaffold and thereby indirectly alter loop structure(s). If this approach is taken, mutations should not saturate the sequence, but rather few mutations should be introduced. Preferably, no more than between 3–20 changes should be introduced to the β-sheet sequences by this approach.

Sequence variation may be introduced by any technique including, for example, mutagenesis by Taq polymerase (Tindall and Kunkel, Biochemistry 27:6008 (1988)), fragment recombination, or a combination thereof. Similarly, an increase of the structural diversity of libraries, for example, by varying the length as well as the sequence of the CDR-like loops, or by structural redesign based on the advantageous framework mutations found in selected pools, may be used to introduce further improvements in antibody mimic scaffolds.

Antibody Mimic Fusions

The antibody mimics described herein may be fused to other protein domains. For example, these mimics may be integrated with the human immune response by fusing the constant region of an IgG ($F_c$) with an antibody mimic, such as an $^{10}$Fn3 module, preferably through the C-terminus of $^{10}$Fn3. The $F_c$ in such a $^{10}$Fn3-$F_c$ fusion molecule activates the complement component of the immune response and increases the therapeutic value of the antibody mimic. Similarly, a fusion between an antibody mimic, such as $^{10}$Fn3, and a complement protein, such as C1q, may be used to target cells, and a fusion between an antibody mimic, such as $^{10}$Fn3, and a toxin may be used to specifically destroy cells that carry a particular antigen. In addition, an antibody scaffold, such as $^{10}$Fn3, in any form may be fused with albumin to increase its half-life in the bloodstream and its tissue penetration. Any of these fusions may be generated by standard techniques, for example, by expression of the fusion protein from a recombinant fusion gene constructed using publically available gene sequences.

Scaffold Multimers

In addition to monomers, any of the scaffold constructs described herein may be generated as dimers or multimers of antibody mimics as a means to increase the valency and thus the avidity of antigen binding. Such multimers may be generated through covalent binding. For example, individual $^{10}$Fn3 modules may be bound by imitating the natural $^{8}$Fn3–$^{9}$Fn3–$^{10}$Fn3 C-to-N-terminus binding or by imitating antibody dimers that are held together through their constant regions. A $^{10}$Fn3-Fc construct may be exploited to design dimers of the general scheme of $^{10}$Fn3-Fc::Fc-$^{10}$Fn3. The bonds engineered into the Fc::Fc interface may be covalent or non-covalent. In addition, dimerizing or multimerizing partners other than Fc can be used in hybrids, such as $^{10}$Fn3 hybrids, to create such higher order structures.

In particular examples, covalently bonded multimers may be generated by constructing fusion genes that encode the multimer or, alternatively, by engineering codons for cysteine residues into monomer sequences and allowing disulfide bond formation to occur between the expression products. Non-covalently bonded multimers may also be generated by a variety of techniques. These include the introduction, into monomer sequences, of codons corresponding to positively and/or negatively charged residues and allowing interactions between these residues in the expression products (and therefore between the monomers) to occur. This approach may be simplified by taking advantage of charged residues naturally present in a monomer subunit, for example, the negatively charged residues of fibronectin. Another means for generating non-covalently bonded antibody mimics is to introduce, into the monomer gene (for example, at the amino- or carboxy-termini), the coding sequences for proteins or protein domains known to interact. Such proteins or protein domains include coil-coil motifs, leucine zipper motifs, and any of the numerous protein subunits (or fragments thereof) known to direct formation of dimers or higher order multimers.

Fibronectin-Like Molecules

Figure 21:
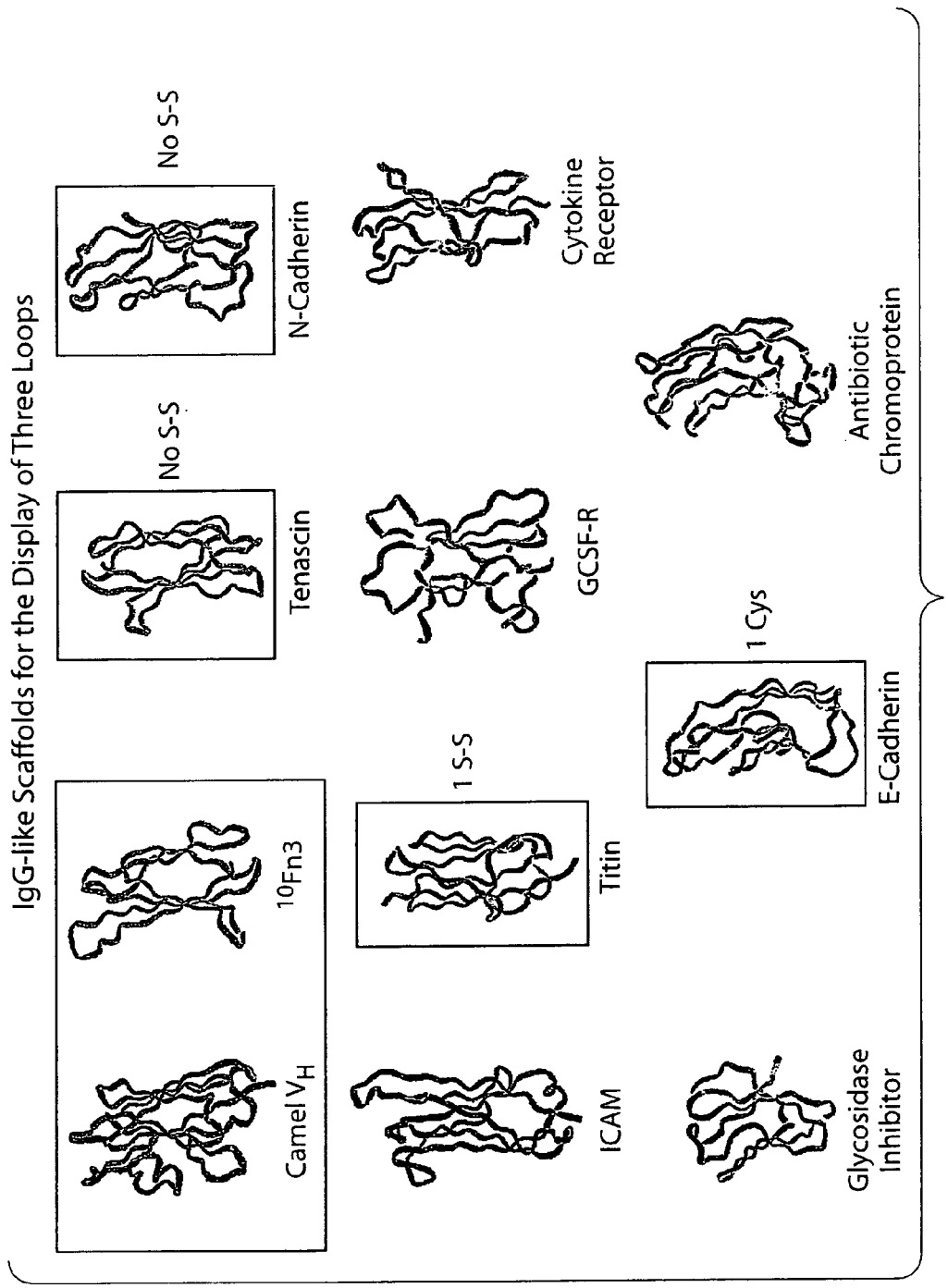
FIG. 21 is a series of IgG-like scaffolds for the display of up to three loops.

Although $^{10}$Fn3 represents a preferred scaffold for the generation of antibody mimics, other molecules may be substituted for $^{10}$Fn3 in the molecules described herein. These include, without limitation, human fibronectin modules $^1$Fn3-$^9$Fn3 and $^{11}$Fn3-$^{17}$Fn3 as well as related Fn3 modules from non-human animals and prokaryotes. In addition, Fn3 modules from other proteins with sequence homology to $^{10}$Fn3, such as tenascins and undulins, may also be used. Other exemplary scaffolds having immunoglobulin-like folds (but with sequences that are unrelated to the $V_H$ domain) are shown in FIG. 21 and include N-cadherin, ICAM-2, titin, GCSF receptor, cytokine receptor, glycosidase inhibitor, E-cadherin, and antibiotic chromoprotein. Yet further domains with related structures may be derived from myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, telikin, NCAM, twitchin, neuroglian, growth hormone receptor, erythropoietin receptor, prolactin receptor, GC-SF receptor, interferon-gamma receptor, β-galactosidase/glucuronidase, β-glucuronidase, and transglutaminase. Alternatively, any other protein that includes one or more immunoglobulin-like folds may be utilized. Such proteins may be identified, for example, using the program SCOP (Murzin et al., J. Mol. Biol. 247:536 (1995); Lo Conte et al., Nucleic Acids Res. 25:257 (2000).

Figure 22:
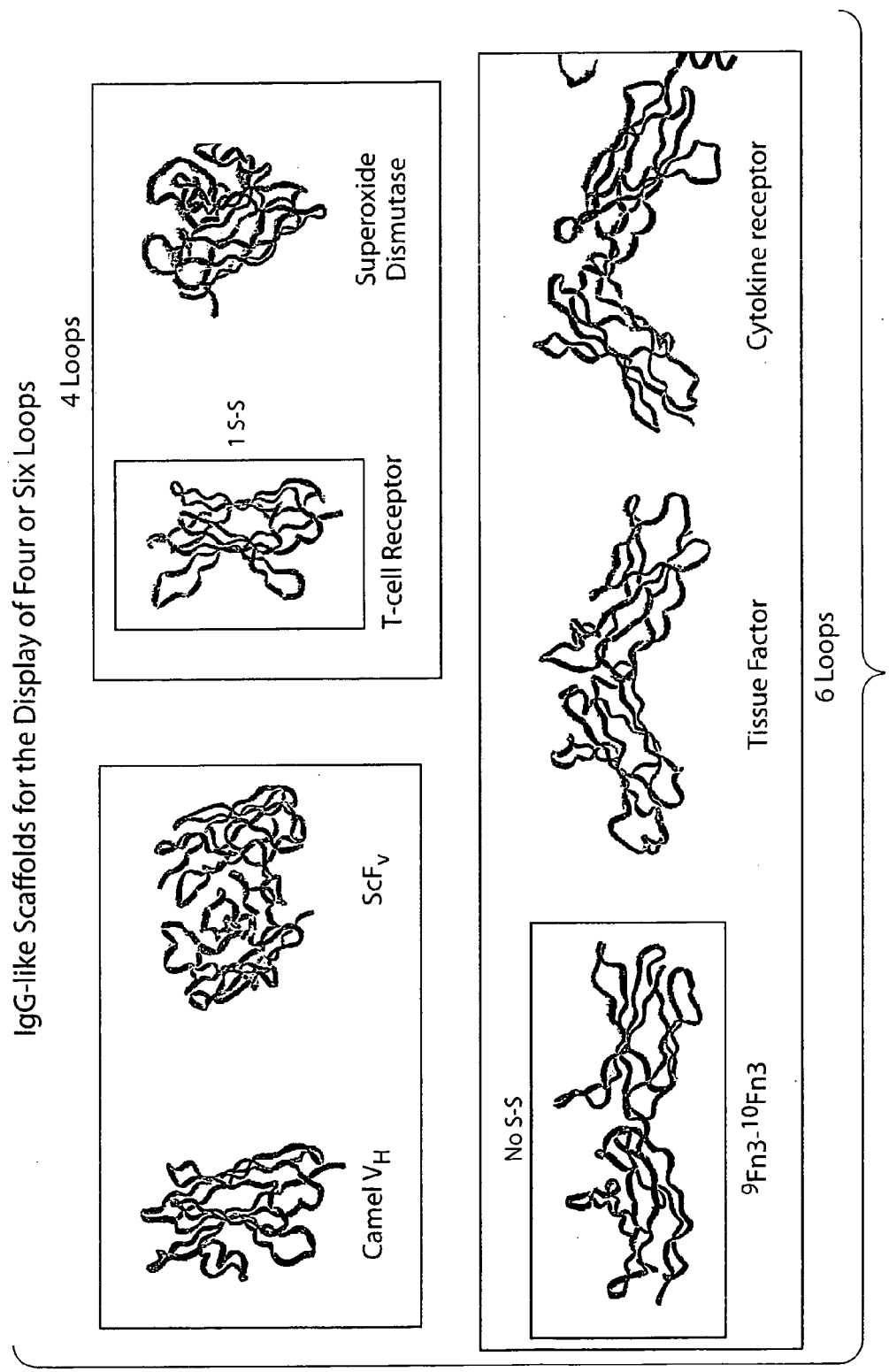
FIG. 22 is a series of IgG-like scaffolds for the display of up to four, or even six, loops.

Generally, any molecule that exhibits a structural relatedness to the $V_H$ domain (as identified, for example, using the computer program above) may be utilized as an antibody mimic. Such molecules may, like fibronectin, include three loops at the N-terminal pole of the molecule and three loops at the C-terminal pole, each of which may be randomized to create diverse libraries; alternatively, larger domains may be utilized, having larger numbers of loops, as long as a number of such surface randomizable loops are positioned closely enough in space that they can participate in antigen binding. FIG. 22 shows examples of useful domains having more than three loops positioned close to each other. These examples include T-cell antigen receptor and superoxide dismutase, which each have four loops that can be randomized; and an Fn3 dimer, tissue factor domains, and cytokine receptor domains, each of which have three sets of two similar domains where three randomizable loops are part of the two domains (bringing the total number of loops to six).

Figure 23:
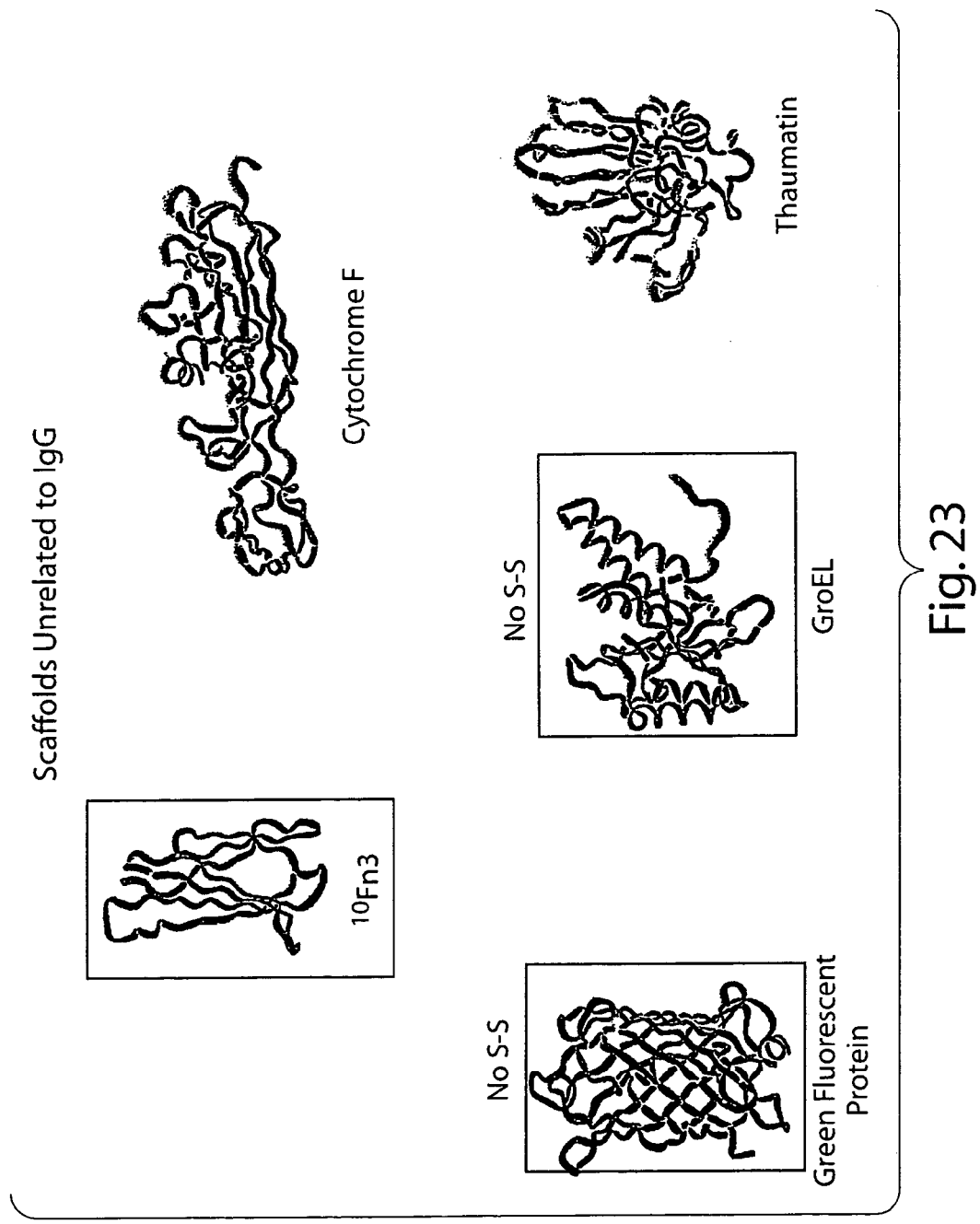
FIG. 23 is a series of scaffolds, unrelated to IgG, for the display of loop structures.

In yet another alternative, any protein having variable loops positioned close enough in space may be utilized for candidate binding protein production. For example, large proteins having spatially related, solvent accessible loops may be used, even if unrelated structurally to an immunoglobulin-like fold. Exemplary proteins include, without limitation, cytochrome F, green fluorescent protein, GroEL, and thaumatin (FIG. 23). The loops displayed by these proteins may be randomized and superior binders selected from a randomized library as described herein. Because of their size, molecules may be obtained that exhibit an antigen binding surface considerably larger than that found in an antibody-antigen interaction. Other useful scaffolds of this type may also be identified using the program SCOP (Murzin et al., J. Mol. Biol. 247:536 (1995)) to browse among candidate proteins having numerous loops, particularly loops positioned among parallel beta sheets or a number of alpha-helices.

Modules from different organisms and parent proteins may be most appropriate for different applications. For example, in designing an antibody mimic, it may be most desirable to generate that protein from a fibronectin or fibronectin-like molecule native to the organism for which a therapeutic is intended. In contrast, the organism of origin is less important or even irrelevant for antibody mimics that are to be used for in vitro applications, such as diagnostics, or as research reagents.

For any of these molecules, libraries may be generated and used to select binding proteins by any of the methods described herein.

Directed Evolution of Scaffold-Based Binding Proteins

The antibody mimics described herein may be used in any technique for evolving new or improved binding proteins. In one particular example, the target of binding is immobilized on a solid support, such as a column resin or microtiter plate well, and the target contacted with a library of candidate scaffold-based binding proteins. Such a library may consist of antibody mimic clones, such as $^{10}$Fn3 clones constructed from the wild type $^{10}$Fn3 scaffold through randomization of the sequence and/or the length of the $^{10}$Fn3 CDR-like loops. If desired, this library may be an RNA-protein fusion library generated, for example, by the techniques described in Szostak et al., U.S. Ser. No. 09/007,005 and Ser. No. 09/247,190; Szostak et al., WO98/31700; and Roberts & Szostak, Proc. Natl. Acad. Sci. USA (1997) vol. 94, p. 12297–12302. Alternatively, it may be a DNA-protein library (for example, as described in Lohse, DNA-Protein Fusions and Uses Thereof, U.S. Ser. No. 60/110,549, U.S. Ser. No. 09/459,190, and WO 00/32823). The fusion library is incubated with the immobilized target, the support is washed to remove non-specific binders, and the tightest binders are eluted under very stringent conditions and subjected to PCR to recover the sequence information or to create a new library of binders which may be used to repeat the selection process, with or without further mutagenesis of the sequence. A number of rounds of selection may be performed until binders of sufficient affinity for the antigen are obtained.

In one particular example, the $^{10}$Fn3 scaffold may be used as the selection target. For example, if a protein is required that binds a specific peptide sequence presented in a ten residue loop, a single $^{10}$Fn3 clone is constructed in which one of its loops has been set to the length of ten and to the desired sequence. The new clone is expressed in vivo and purified, and then immobilized on a solid support. An RNA-protein fusion library based on an appropriate scaffold is then allowed to interact with the support, which is then washed, and desired molecules eluted and re-selected as described above.

Similarly, the scaffolds described herein, for example, the $^{10}$Fn3 scaffold, may be used to find natural proteins that interact with the peptide sequence displayed by the scaffold, for example, in an $^{10}$Fn3 loop. The scaffold protein, such as the $^{10}$Fn3 protein, is immobilized as described above, and an RNA-protein fusion library is screened for binders to the displayed loop. The binders are enriched through multiple rounds of selection and identified by DNA sequencing.

In addition, in the above approaches, although RNA-protein libraries represent exemplary libraries for directed evolution, any type of scaffold-based library may be used in the selection methods of the invention.

Use

The antibody mimics described herein may be evolved to bind any antigen of interest. These proteins have thermodynamic properties superior to those of natural antibodies and can be evolved rapidly in vitro. Accordingly, these antibody mimics may be employed in place of antibodies in all areas in which antibodies are used, including in the research, therapeutic, and diagnostic fields. In addition, because these scaffolds possess solubility and stability properties superior to antibodies, the antibody mimics described herein may also be used under conditions which would destroy or inactivate antibody molecules. Finally, because the scaffolds of the present invention may be evolved to bind virtually any compound, these molecules provide completely novel binding proteins which also find use in the research, diagnostic, and therapeutic areas.

Experimental Results

Exemplary scaffold molecules described above were generated and tested, for example, in selection protocols, as follows.

Library Construction

Figures 18, 19:
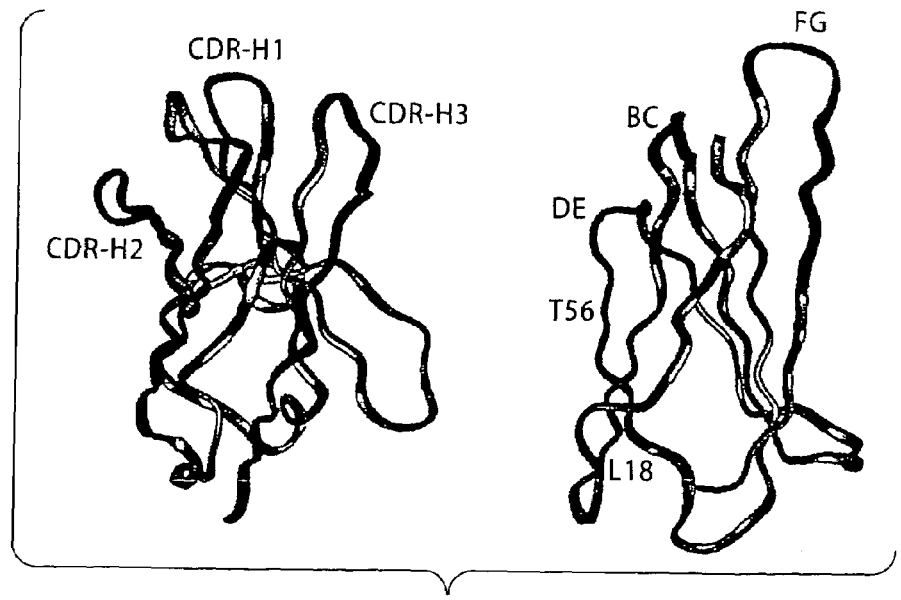
FIG. 18 is a graph showing an alignment of the primary sequences of the llama $V_H$ domain and the wild-type human $^{10}$Fn3 domain. Homologous residues between the two sequences are indicated. The $^{10}$Fn3 residues outside the randomized loops that were found to have mutated in approximately 45% of the selected clones are marked with arrows under the wild-type $^{10}$Fn3 sequence and with the letter that identifies the selected residue.
FIG. 19 shows schematic representations of the llama $V_H$ domain and the wild-type human $^{10}$Fn3 domain. The locations of the mutated framework residues are indicated.

A complex library was constructed from three fragments, each of which contained one randomized area corresponding to a CDR-like loop. The randomized residues are indicated in FIG. 18 as underlined sequences, specifically, residues 23–29 of the $^{10}$Fn3 BC loop (corresponding to CDR-H1 of the llama $V_H$); residues 52–55 of the $^{10}$Fn3 DE loop (corresponding to CDR-H2 of the llama $V_H$); and residues 78–87 of the $^{10}$Fn3 FG loop (corresponding to CDR-H3 of the llama $V_H$). The fragments were named BC, DE, and FG based on the names of the CDR-H-like loops contained within them; in addition to $^{10}$Fn3 and a randomized sequence, each of the fragments contained stretches encoding an N-terminal His$_6$ domain or a C-terminal FLAG peptide tag. At each junction between two fragments (i.e., between the BC and DE fragments or between the DE and FG fragments), each DNA fragment contained recognition sequences for the EarI Type IIS restriction endonuclease. This restriction enzyme allowed the splicing together of adjacent fragments while removing all foreign, non-$^{10}$Fn3, sequences. It also allowed for a recombination-like mixing of the three $^{10}$Fn3 fragments between cycles of mutagenesis and selection.

The wild-type, human $^{10}$Fn3 gene was cloned from a human liver library (Maxim Biotech, South San Francisco, Calif.) using the primers Hu5PCR-NdeI 5'CATATG-GTTTCTGATGTTCCGAGG3'; SEQ ID NO: 28) and Hu3PCR-EcoRI (5'GAATTCCTATGTTCGGTAAT-TAATGGAAATTG3'; SEQ ID NO: 29). Three different libraries were constructed from the wild-type segments obtained by the PCR of the $^{10}$Fn3 clone and from randomized segments obtained by oligonucleotide synthesis. The BC$_r$-DE$_r$-FG$_r$ library was obtained by randomizing the selected residues in BC, DE, and FG loops; the BC$_r$-DE$_{wt}$-FG$_r$ library was obtained by randomizing the selected residues in BC and FG loops, leaving the DE loop sequence wild-type; and the BC$_{wt}$-DE$_{wt}$-FG$_r$ library was obtained by randomizing the selected residues in the FG loop only.

The BC$_r$, DE$_r$, and FG$_r$ fragments were made synthetically. Each fragment was assembled from two overlapping oligonucleotides, which were first annealed, then extended to form the double-stranded DNA form of the fragment. The oligonucleotides that were used to construct and process the three fragments are listed below; the "Top" and "Bottom" species for each fragment are the oligonucleotides that contained the entire $^{10}$Fn3 encoding sequence. In these oligonucleotides designations, "N" indicates A, T, C, or G; and "S" indicates C or G.

HfnLbcTop (His):

5'-GG AAT TCC TAA TAC GAC TCA CTA      (SEQ ID NO: 1)

TAG GGA CAA TTA CTA TTT ACA ATT ACA

ATG CAT CAC CAT CAC CAT CAC GTT TCT

GAT GTT CCG AGG GAC CTG GAA GTT GTT

GCT GCG ACC CCC ACC AGC-3'

HfnLbcTop (an alternative N-terminus):

5'-GG AAT TCC TAA TAC GAC TCA CTA      (SEQ ID NO: 2)

TAG GGA CAA TTA CTA TTT ACA ATT ACA

ATG GTT TCT GAT GTT CCG AGG GAC CTG

GAA GTT GTT GCT GCG ACC CCC ACC

AGC-3'

HFnLBCBot-flag8:

5'-AGC GGA TGC CTT GTC GTC GTC GTC      (SEQ ID NO: 3)

CTT GTA GTC GCT CTT CCC TGT TTC TCC

GTA AGT GAT CCT GTA ATA TCT (SNN)$_7$

CCA GCT GAT CAG TAG GCT GGT GGG GGT

CGC AGC-3'

HFnBC3'-flag8:

5'-AGC GGA TGC CTT GTC GTC GTC GTC      (SEQ ID NO: 4)

CTT GTA GTC GCT CTT CCC TGT TTC TCC

GTA AGT GAT CC-3'

HFnLDETop:

5'-GG AAT TCC TAA TAC GAC TCA CTA      (SEQ ID NO: 5)

TAG GGA CAA TTA CTA TTT ACA ATT ACA

ATG CAT CAC CAT CAC CAT CAC CTC TTC

ACA GGA GGA AAT AGC CCT GTC C-3'

HFnLDEBot-flag8:

5'-AGC GGA TGC CTT GTC GTC GTC GTC      (SEQ ID NO: 6)

CTT GTA GTC GCT CTT CGT ATA ATC AAC

TCC AGG TTT AAG GCC GCT GAT GGT AGC

TGT (SNN)$_4$ AGG CAC AGT GAA

CTC CTG GAC AGG GCT ATT TCC TCC

TGT-3'

HFnDE3'-flag8:

5'-AGC GGA TGC CTT GTC GTC GTC GTC    (SEQ ID NO: 7)
CTT GTA GTC GCT CTT CGT ATA ATC AAC
TCC AGG TTT AAG G-3'

HFnLFGTop:

5'-GG AAT TCC TAA TAC GAC TCA CTA     (SEQ ID NO: 8)
TAG GGA CAA TTA CTA TTT ACA ATT ACA
ATG CAT CAC CAT CAC CAT CAC CTC TTC
TAT ACC ATC ACT GTG TAT GCT GTC-3'

HFnLFGBot-flag8:

5'-AGC GGA TGC CTT GTC GTC GTC GTC    (SEQ ID NO: 9)
CTT GTA GTC TGT TCG GTA ATT AAT GGA
AAT TGG (SNN)$_{10}$ AGT GAC AGC ATA CAC
AGT GAT GGT ATA-3'

HFnFG3'-flag8:

5'-AGC GGA TGC CTT GTC GTC GTC GTC    (SEQ ID NO: 10)
CTT GTA GTC TGT TCG GTA ATT AAT
GGA AAT TGG-3'

T7Tmv (introduces T7 promoter and TMV untranslated region needed for in vitro translation):

5'-GCG TAA TAC GAC TCA CTA TAG GGA    (SEQ ID NO: 11)
CAA TTA CTA TTT ACA ATT ACA-3'

ASAflag8:

5'-AGC GGA TGC CTT GTC GTC GTC GTC    (SEQ ID NO: 12)
CTT GTA GTC-3'

Unispl-s (spint oligonucleotide used to ligate mRNA to the puromycin-containing linker, described by Roberts et al, 1997, supra):

5'-TTTTTTTTTNAGCGGATGC-3'     (SEQ ID NO: 13)

A18 - - - 2PEG (DNA-puromycin linker):

5'-(A)$_{18}$(PEG)$_2$CCPur          (SEQ ID NO: 14)

The oligonucleotide pair BC$_{Top}$ and BC$_{Bot-flag8}$ was used to construct the fragment which contains the randomized BC loop; the pair DE$_{Top}$ and DE$_{Bot-flag 8}$ was used to construct the fragment which contains the randomized DE loop; the pair BC$_{Top}$ and DE$_{3-Flag8}$ was used to PCR-amplify the BC$_{wt}$-DE$_{wt}$ fragments; and the pair FG$_{Top}$ and FG$_{Bot-Flag8}$ was used to construct the fragment which contains the randomized FG loop. The pairs of oligonucleotides (500 pmol of each) were annealed in 100 µL of 10 mM Tris 7.5, 50 mM NaCl for 10 minutes at 85° C., followed by a slow (0.5–1 hour) cooling to room temperature. The annealed fragments with single-stranded overhangs were then extended using 100 U Klenow (New England Biolabs, Beverly, Mass.) for each 100 µL aliquot of annealed oligos, and the buffer made of 838.5 µl H$_2$O, 9 µl 1 M Tris 7.5, 5 µl 1M MgCl$_2$, 20 µl 10 mM dNTPs, and 7.5 µl 1M DTT. The extension reactions proceeded for 1 hour at 25° C.

In order to reduce the frequency of stop codons introduced by the random sequences, the randomized residues were encoded by (NNS)$_n$, where N stands for any nucleotide and S for an equimolar mixture of C and G; only one of the three stop codons (TAG) conforms to the NNS restriction. In addition to the sequence encoding $^{10}$Fn3, the gene fragments contained the 5' Tobacco Mosaic Virus (TMV) untranslated region and the T7 promoter, as well as the sequences encoding a 5' hexahistidine protein purification tag and a 3'FLAG epitope purification tag. In addition, as noted above, Ear I restriction endonuclease recognition sites were engineered into the overlaps between adjacent fragments in order to facilitate the assembly of the three fragments.

Next, each of the double-stranded fragments was transformed into an RNA-protein fusion (PROfusion™) using the technique developed by Szostak et al., U.S. Ser. No. 09/007,005 and U.S. Ser. No. 09/247,190; Szostak et al., WO98/31700; and Roberts & Szostak, Proc. Natl. Acad. Sci. USA (1997) vol. 94, p. 12297–12302. Briefly, the fragments were transcribed using an Ambion in vitro transcription kit, T7-MEGAshortscript™ (Ambion, Austin, Tex.), and the resulting mRNA was gel-purified and ligated to a 5'-phosphorylated DNA-puromycin linker, preferably, 5' dA$_{18}$PEG$_2$dCdCPur) using DNA ligase (Promega, Madison, Wis.); the mRNA was aligned with the DNA linker using a DNA splint oligonucleotide (5' TTTTTTTTTNAGCG-GATGC 3'; SEQ ID NO: 30) as described in Szostak (supra). The mRNA-DNA-puromycin molecule was then translated using the Ambion rabbit reticulocyte lysate-based translation kit in the presence of $^{35}$S-methionine. The resulting mRNA-DNA-puromycin-protein fusion was purified using Oligo(dT) cellulose, (Type 7, Amersham Pharmacia, Piscataway, N.J.) and a complementary DNA strand was synthesized using reverse transcriptase (Superscript™II, Gibco, Life Technologies, Rockville, Md.) and the RT primers described above (Unisplint-S or flagASA), following the manufacturer's instructions (preferably, a two-minute annealing at 70° C. and a 40 minute reaction at 42° C.).

The RNA-protein fusion with annealing cDNA obtained for each fragment was next purified on the resin appropriate to its peptide purification tag, i.e., on Ni-NTA agarose (Qiagen, Valencia, Calif.) for the His$_6$-tag and M2 Anti-Flag Agarose (Sigma, St. Louis, Mo.) for the FLAG-tag, following the procedures recommended by the manufacturers. The fragment-encoding genetic information recovered by KOH elution was amplified by PCR using Pharmacia Ready-to-Go PCR Beads, 10 pmol of 5' and 3' PCR primers, and the following PCR program (Pharmacia, Piscataway, N.J.): Step 1: 95° C. for 3 minutes; Step 2: 95° C. for 30 seconds, 58/62° C. for 30 seconds, 72° C. for 1 minute, 20/25/30 cycles, as required; Step 3: 72° C. for 5 minutes; Step 4: 4° C. until end (typically, 25 cycles).

The resulting DNA was cleaved by 5–6 U EarI (New England Biolabs) per µg DNA; the reaction took place in T4 DNA Ligase Buffer (New England Biolabs) at 37° C., for 1 hour, and was followed by an optional incubation at 70° C.

for 15 minutes to inactivate Ear I. Equal amounts of the BC, DE, and FG fragments were combined and ligated to form a full-length $^{10}$Fn3 gene with randomized loops. The ligation required 10 U of fresh EarI (New England Biolabs) and 20 U of T4 DNA Ligase (Promega, Madison, Wis.), and took 1 hour at 37° C. EarI and ligase were then inactivated by a 15 minute incubation at 65° C.

Three different libraries, $BC_{wt}$-$DE_{wt}$-$FG_r$, $BC_r$-$DE_{wt}$-$FG_r$, and $BC_r$-$DE_r$-$FG_r$, were made in the manner described above. Each contained the form of the FG loop with 10 randomized residues. The BC and the DE loops of the first library bore the wild type $^{10}$Fn3 sequence; a BC loop with 7 randomized residues and a wild type DE loop made up the second library; and a BC loop with 7 randomized residues and a DE loop with 4 randomized residues made up the third library. The complexity of the FG loop in each of these three libraries was $10^{13}$; the further two randomized loops provided the potential for a complexity too large to be sampled in a laboratory. The combination of these libraries provided a master library having $10^{12}$ unique clones.

The sequences of 76 randomly picked clones from the original, randomized, $BC_r$-$DE_r$-$FG_r$ library showed no pattern in the randomized loops (data not shown); the amino acid frequency in the library varied in proportion to the number of codons available that encoded each residue, between 1% per position (glutamic acid, methionine, tryptophan) and 14% per position (proline). In contrast, the average probability for a residue in the preserved, beta-sheet framework to have remained as wild type was found to be 99%.

Figure 8:
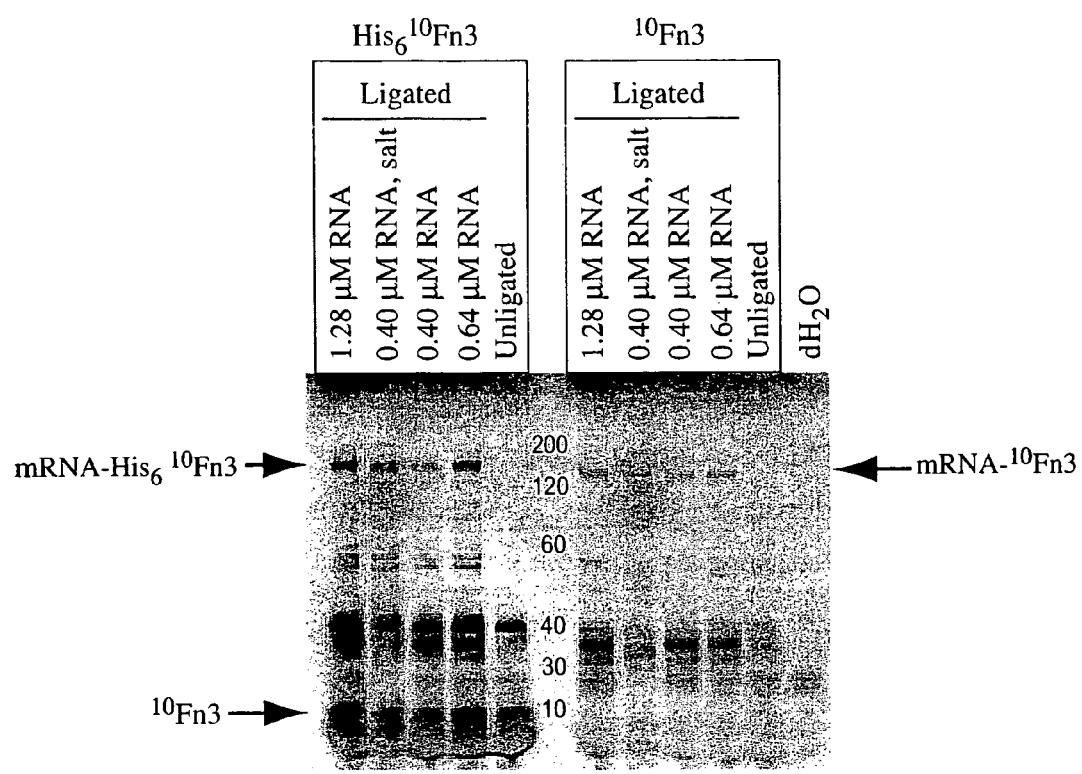
FIG. 8 is a photograph illustrating the formation, under different salt conditions, of RNA-protein fusions which include fibronectin type III domains.

Equimolar amounts of the three libraries (2 pmoles of DNA each) were combined into one master library in order to simplify the selection process; target binding itself was expected to select the most suitable library for a particular challenge. RNA-protein fusions were obtained from the master library following the general procedure described in Szostak et al., U.S. Ser. No. 09/007,005 and Ser. No. 09/247,190; Szostak et al., WO98/31700; and Roberts & Szostak, Proc. Natl. Acad. Sci. USA (1997) vol. 94, p. 12297–12302 (FIG. 8), except that affinity purification performed in rounds three to ten used only M2-Sepharose (see below).

Fusion Selections

The master library in the RNA-protein fusion form was subjected to selection for binding to TNF-α (Pepro Tech, Rocky Hill, N.J.). Two initial protocols were employed: one in which the target was immobilized on an agarose column and one in which the target was immobilized on a BIACORE chip. First, an extensive optimization of conditions to minimize background binders to the agarose column yielded the favorable buffer conditions of 50 mM HEPES pH 7.4, 0.02% Triton, 100 μg/ml sheared salmon sperm DNA. In this buffer, the non-specific binding of the $^{10}$Fn3-RNA fusion to TNF-α Sepharose was 0.3%. The non-specific binding background of the $^{10}$Fn3-RNA/cDNA library to TNF-α Sepharose was found to be 0.1%.

During each round of selection on TNF-α Sepharose, the library was first preincubated for an hour with underivatized Sepharose to remove any remaining non-specific binders; the flow-through from this pre-clearing was incubated for another hour with TNF-α Sepharose. The TNF-α Sepharose was washed for 3–30 minutes.

Figure 9:
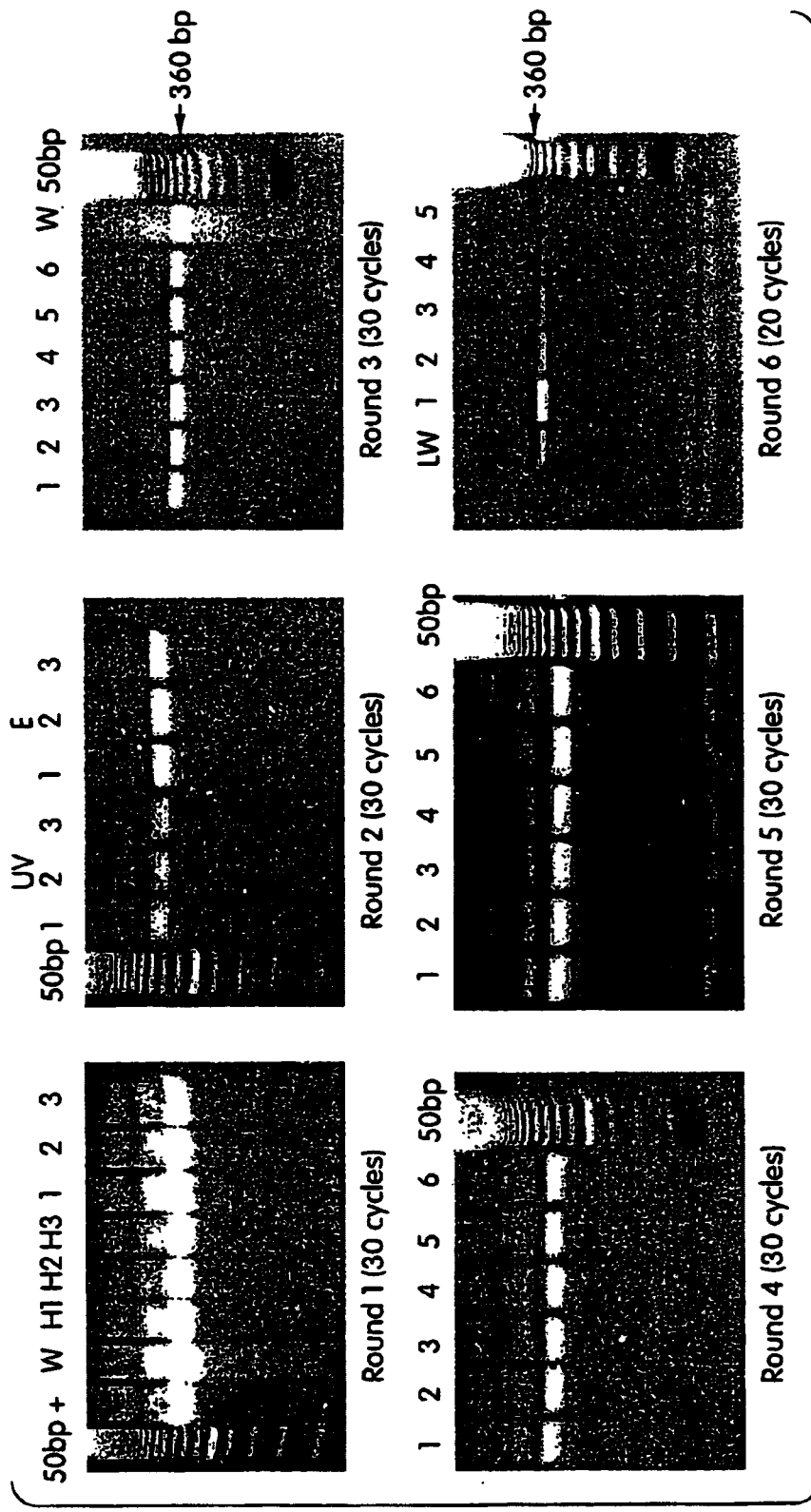
FIG. 9 is a series of photographs illustrating the selection of fibronectin type III domain-containing RNA-protein fusions, as measured by PCR signal analysis.

After each selection, the cDNA component of the complex that had been eluted from the solid support with 0.3 M NaOH or 0.1M KOH was amplified by PCR; a DNA band of the expected size persisted through multiple rounds of selection (FIG. 9); similar results were observed in the two alternative selection protocols, and only the data from the agarose column selection is shown in FIG. 9.

Figure 10:
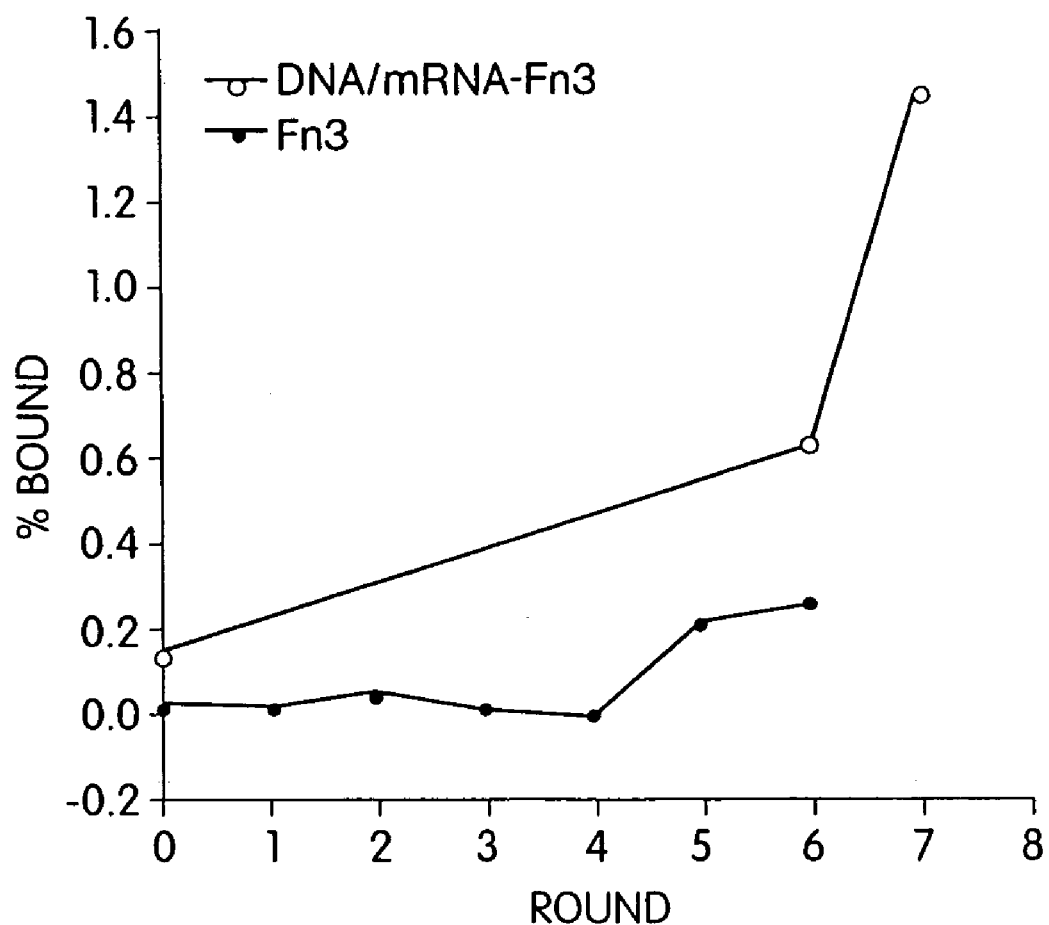
FIG. 10 is a graph illustrating an increase in the percent TNF-α binding during the selections described herein, as well as a comparison between RNA-protein fusion and free protein selections.

In this selection, in the first seven rounds, the binding of Fn3-RNA/cDNA molecules to the target remained low; in contrast, when free protein was translated from DNA pools at different stages of the selection, the proportion of the column binding species increased significantly between rounds (FIG. 10).

Figure 13:
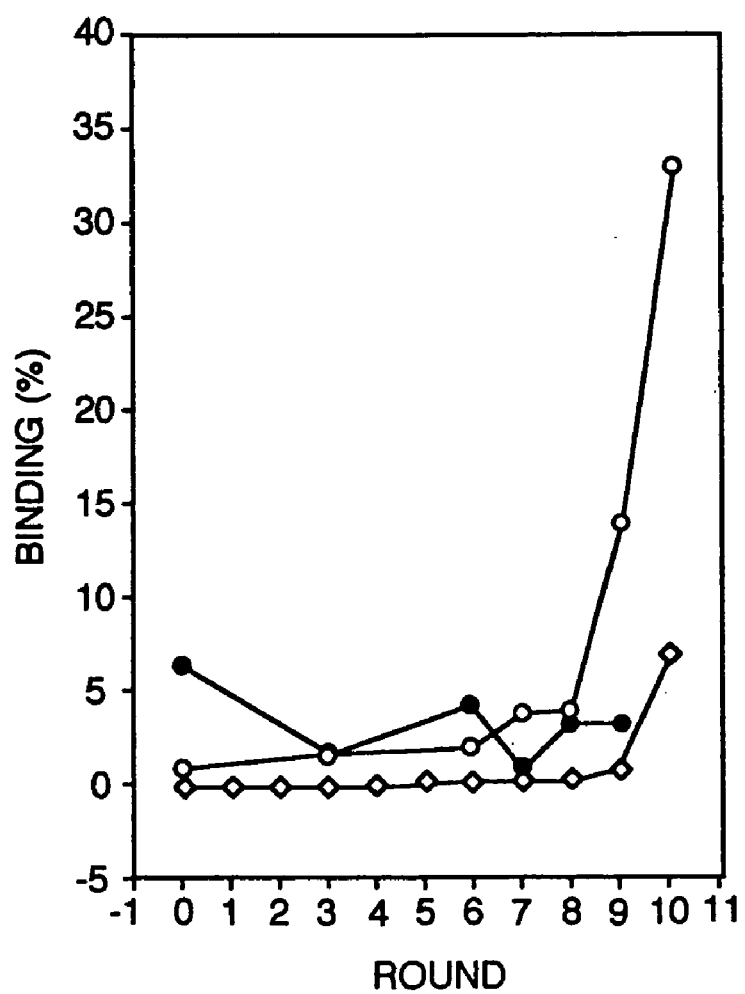
FIG. 13 is a graph showing the time course of an exemplary $^{10}$Fn3-based nucleic acid-protein fusion selection of TNF-α binders. The proportion of nucleic acid-protein fusion pool (open diamonds) and free protein pool (open circles) that bound to TNF-α-Sepharose, and the proportion of free protein pool (full circles) that bound to underivatized Sepharose, are shown.

In later selections, the fusion pools selected in the first eight rounds of selection (R1–8) bound to TNF-α-Sepharose at levels close to the background (<0.25%) (FIG. 13). After nine rounds of selection (R9), the binding of fusion to TNF-α-Sepharose increased sharply to 0.7%, and, after ten rounds of selection (R10), the binding increased further to 7% (FIG. 13). These selections were carried out using TNF-α immobilized on Epoxy-Activated Sepharose™ 6B (Amersham Pharmacia) at 10 mg TNF/g Sepharose in 10 mL. Before use, the TNF-α-derivatized Sepharose was blocked in Binding Buffer (50 mM HEPES, pH 7.4, 0.02% Triton, 0.1 mg/mL sheared salmon sperm DNA (Ambion)), overnight, at 4° C.

The $^{10}$Fn3-based master library was transcribed, ligated to the puromycin-bearing linker, translated into an mRNA-protein library in the presence of 5–10 μL/300 μL $^{35}$S-methionine, affinity purified on Oligo(dT) Cellulose, reverse-transcribed into a DNA/mRNA-protein library, and affinity-purified on M2-Sepharose (for rounds 3–10), as described above. Forty pmol of DNA/mRNA-protein fusion library molecules, the equivalent of 20 copies of $4 \times 10^{12}$ different sequences, were recovered, then subjected to the first round (R1) of the selection.

In the first step of the selection, 40 pmoles of the DNA/mRNA-protein library was incubated for 1 hour at 4° C., with tumbling, in 300 μL of Binding Buffer with 30 μL of Epoxy-Sepharose that had been subjected to the derivatization procedure in the absence of TNF-α. In the second round, 24 pmol of the library was added, and in the remaining eight rounds, 0.1–2 pmol of the library was added. The supernatant was recovered by microcentrifugation through a Micro Bio-Spin® chromatography column (BIO-RAD, Hercules, Calif.), then incubated with 30 μL of TNF-α-Sepharose (6 μM) in 300 μL of the Binding Buffer for 1 hour at 4° C. (during Rounds 7–10, the Binding Buffer contained an additional 1 mg/mL of BSA). The TNF-α-Sepharose was recovered on a spin column, then washed with 3×300 μL of Binding Buffer, eluted with 100 μL of 0.1 M KOH, and finally neutralized with 1 μL of 1 M Tris 8.0, 8 μL of 1 M HCl. Samples of the library, of the TNF-α-Sepharose before and after the elution, of the washes, and of the elutions were quantified by counting $^{35}$S-methionine in the sample in a scintillation counter. The next round of selection began with the formation of a new DNA/mRNA-protein pool by PCR amplification, which was transcribed, translated, and reverse-transcribed from the PCR product.

The DNA pools obtained from the elution after nine and after ten rounds were cloned into the TOPO™ TA®, pCR2.1 cloning vector (Invitrogen, Carlsbad, Calif.) and transformed into E. coli. Between 30 and 100 clones were picked and grown into plasmid minipreps (Qiagen). Thirty-eight clones from R9 and 29 clones from R10 were picked at random and sequenced (DNA Sequencing Core Facility, Massachusetts General Hospital, Dept. of Molecular Biology, Boston, Mass.). The program ClustalW[60] was used to align the resulting protein sequences.

Amino Acid Residue Sequences of the TNF-α Binding Clones

Thirty-eight of the 61 clones derived from R9 and from R10 had unique amino acid sequences, a surprising diversity. The ten clones that were isolated more than once, presumably because of their superior binding to TNF-α, are listed in Table 1 (full sequences in FIG. 25).

Of the 61 clones picked randomly from the winning pool, only one (clone T09.08, sequence not shown) had its origin in the $BC_{wt}$-$DE_{wt}$-$FG_r$ library, with another six from the $BC_r$-$DE_{wt}$-$FG_r$ library. The observation that the remaining 54 (88% of the winners) were selected from the $BC_r$-$DE_r$-$FG_r$ library points out the importance for TNF-α cooperative binding of the target by several loops.

The most common motif found in the selected loop sequences is PWA(S/T), which is found in the DE loop of 33 of the 61 clones; the more loosely defined sequence of PW(A/G) is seen in 41/61 clones. Such a strong selection for a specific DE sequence is surprising since the analogous CDR-H2 loops of antibody $V_H$ domains generally make only a small contribution to antigen binding. On the other hand, the short length of the DE loop, which means that $10^7$ copies of each possible tetrapeptide sequence would be expected to be present in the library, would facilitate the optimization of any contribution of the DE loop to the selected properties. A survey of other Fn3 domains (Dickenson et al., J. Mol. Biol. 236:1079–1092 (1994)) shows that proline is found at positions equivalent to the $^{10}$Fn3 residue 52 as frequently as is the wild-type glycine; similarly, alanine, glycine, and the wild-type lysine are all common at positions equivalent to the $^{10}$Fn3 position 54. In consequence, it appears likely that the selected residues at positions 52 and 54 are at least consistent with favorable biophysical properties. In contrast, no tryptophan is found at the position equivalent to the $^{10}$Fn3 residue 53, which suggests that Tryptophan 53 may have been selected for a reason specific to the present selection, such as due to a contribution to TNF-α binding. This is consistent with the absence of this motif in later selections against other antigens, again suggesting that the PWA/G motif is more likely to contribute to TNF-α binding directly than through stability or solubility of the $^{10}$Fn3 domain. The preference for the PWA/G motif on loop DE suggests another possible reason for the preference for the $BC_r$-$DE_r$-$FG_r$ library during the selection: the $BC_r$-$DE_r$-$FG_r$ library alone contained the randomized DE loop, and would be expected to outcompete the other two libraries if the PWA/G sequence were important to target binding.

The sequences selected most frequently in the BC loop is NRSGLQS (12/61) (SEQ ID NO: 31), whereas the sequence selected most commonly in the FG loop is AQTGHHLHDK (6/61) (SEQ ID NO: 32). An NRSGLQS BC loop and an AQTGHHLHDK FG loop have not been found in the same molecule, but two clones were found which contain the most frequently isolated sequences on two of the three randomized loops. These clones, T10.06 (BC: NRSGLQS, DE: PWA) and T09.12 (DE: PWA, FG: AQTGHHLHDK), have two of the lowest four dissociation constants from TNF-α of the clones examined (Table 1).

Due to the use of a Taq polymerase that contains no proofreading activity, every round of PCR introduced additional random mutations into both the CDR-like loops and the beta-sheet scaffold of the $^{10}$Fn3 sequence, at the estimated rate of 0.01% per base pair, i.e., 3% per $^{10}$Fn3 gene per round of PCR and approximately 75% per round of selection. Consequently, it is likely that the residues preserved as wild-type and those preserved in a non-wild-type stable sequence indicate that such sequences were selected due to their superior properties. In the mutated loops, it is impossible to distinguish between the mutations introduced by oligonucleotide synthesis or by PCR mutagenesis, but in the beta-strand scaffold, most of the mutations selected originate from Taq errors. The selected clones showed several conserved changes in the scaffold of the protein, which had not been randomized intentionally. FIG. 18 indicates the residues in the $^{10}$Fn3 beta sheet that had not been randomized, but nevertheless mutated during selection. This mutagenesis occurred at the frequency of 26–28 of the 61 clones; these mutations are marked with arrows under the wild-type $^{10}$Fn3 sequence and with the letter that identifies the selected residue. In particular, 28 of the 61 clones mutated from Leucine 18 to Arginine or to Glutamine, and 26 clones mutated from Threonine 56 to Isoleucine. FIG. 19 shows the location of these scaffold mutations. Whereas position 56 is at the stem loop DE and thus would be expected to affect the conformation and the target-binding properties of this loop, the distance of position 18 from the presumed TNF-α-binding loops suggests that the selective advantage of this mutation may arise from an indirect effect on the conformation of loop BC or from an effect on the stability of the protein (FIG. 19). This is supported by an experiment in which clone T10.06, which contains the frequently seen L18R and T56I changes from the wild-type, was mutagenized to reverse position 18 back to the wild-type leucine. This change caused an increase of the $K_d$ of the variant by approximately 10-fold. The weaker binding of the T10.06(L18) protein to TNF-α suggests that the residue at position 18 has an effect on the binding of the target by the CDR-like loops, possibly by a minor structural change that is transmitted through the beta-strand to loop BC.

Affinity and Specificity of the Selected TNF-α Binding Pools

The apparent average $K_d$ values of free protein pools for TNF-α after nine and after ten rounds of selection were found to be indistinguishable (4 and 6 nM, respectively; Table 1); this similarity in affinity is consistent with the relatively low (10 fold) level of enrichment observed in the last round of selection and with the similarity in the sequence composition of the two pools. The apparent average $K_d$ values of free protein pool after four further rounds of selection was 3 nM, also indistinguishable from those of R9 and R10 pools In order to assess the specificity of the binding of the pool selected after ten rounds of selection, we compared the binding of two different free protein pools to three cytokines immobilized on Sepharose to TNF-α, the target of the selection, and to IL-1α and IL-13, which were irrelevant to the selection. The first pool had been transcribed and translated from the initial, randomized DNA library before the selection (R0), and the second pool, from the library after ten rounds of selection (R10).

To carry out these experiments, the PCR product of the elution after the tenth round of selection was transcribed and translated in vitro, in the presence of $^{35}$S-methionine but without forming the mRNA-protein fusion. The resulting fraction of the free protein bound to TNF-α-Sepharose, to IL-1α-Sepharose, to IL-13-Sepharose at approximately 10 μM, 30 μM, and 50 μM, respectively, and to underivatized Sepharose was compared (FIG. 20), using the procedure described above for DNA/mRNA-protein fusion binding to TNF-α-Sepharose. The amount of the selected pool bound to each of the targets was measured by scintillation counting of the washed beads.

Figure 20:
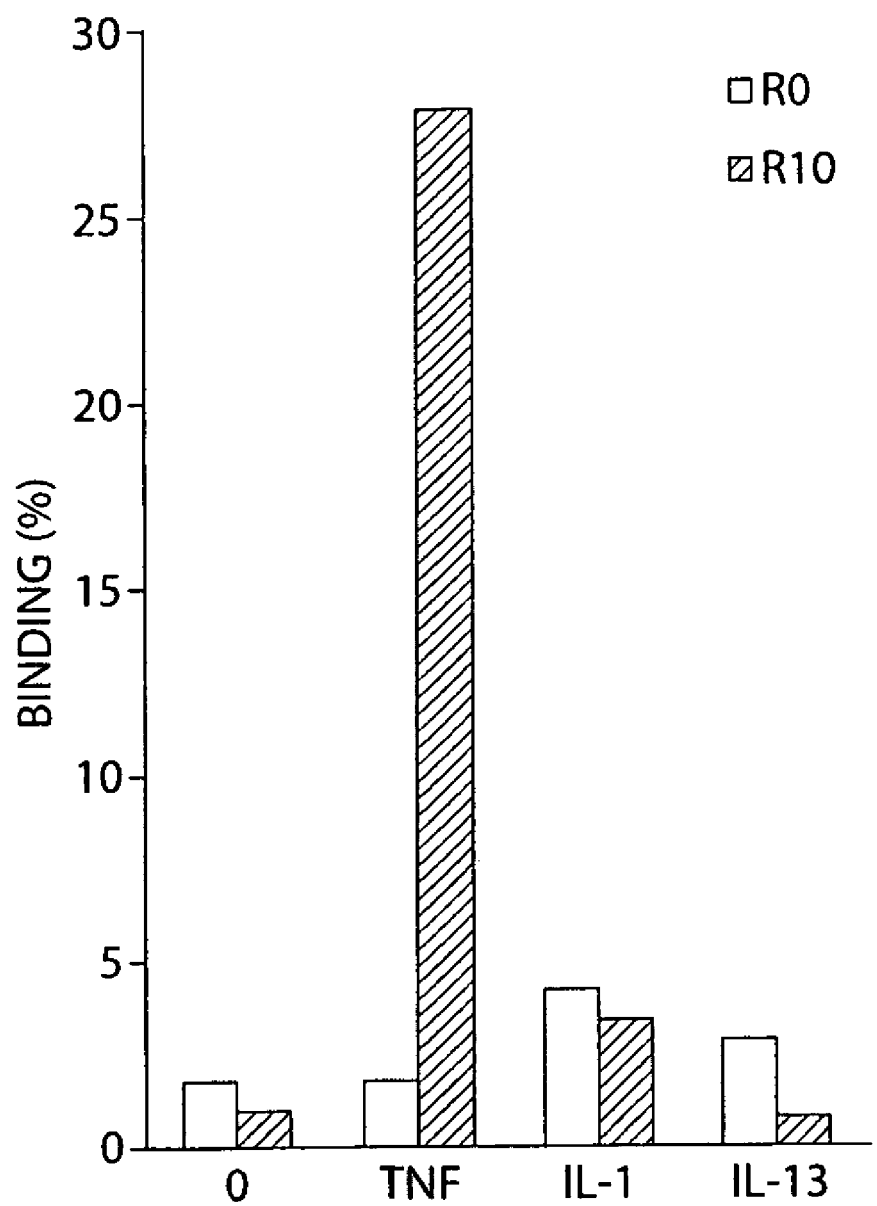
FIG. 20 is a graph illustrating the efficiency and specificity of binding of a free-protein pool translated from the original library (R0) and after ten rounds of selection with TNF-α (R10). Protein pool binding to underivatized Sepharose, to TNF-α-Sepharose, to IL-1α-Sepharose, and to IL-13-Sepharose is compared.

FIG. 20 shows that, whereas the binding of R0 to TNF-α, IL-1α, and IL-13 was similar (2%, 4%, and 3%, respectively), the ten rounds of selection resulted in 32% binding to the targeted TNF-α, in 3% binding to IL-1α, and in 1% binding to IL-13. The absolute and the relative increase of protein binding to TNF-α demonstrates the ability of the $^{10}$Fn3 scaffold and of the DNA/mRNA-protein fusion-based selection system to select target-specific binders.

Figure 24A:
FIGS. 24A–24D are photographic and graphic illustrations demonstrating the specific capture of a target (TNF-α) by a mimic immobilized on a solid surface.
Figure 24B:
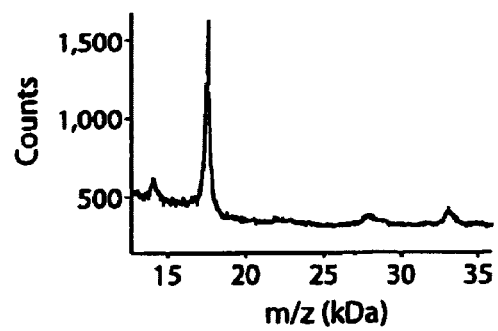
Figure 24C:
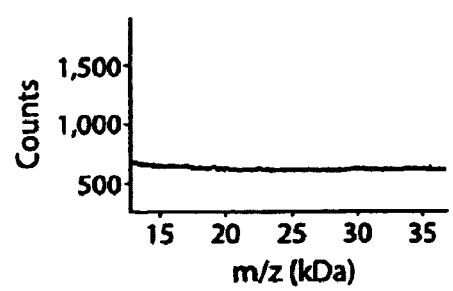
Figure 24D:
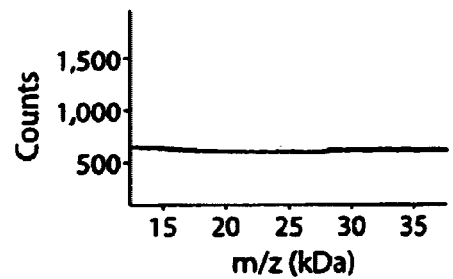

To examine the specificity of binding further, clone T09.12 was immobilized in a microarray format (as generally described below) and was tested for binding to soluble TNF-α. Specific binding of TNF-α to this clone was detected using fluorescence detection (FIG. 24A) and mass spectroscopy (FIG. 24B). For the mass spectroscopy results, binding assays were carried out in the presence of fetal bovine serum, an exemplary complex biological fluid containing a variety of potential interfering proteins. For fluorescence detection (FIG. 24A), a mixture of RNA-$^{10}$Fn3 fusion of wild-type $^{10}$Fn3 and of the T09.12 variant (Table 1) was hybridized onto a DNA microarray on which oligonucleotides complementary to the RNA portion of the fusion molecules had been immobilized at 600 micron pitch, with 24 replicate features. After removal of unhybridized fusion by washing, the surface was exposed to biotin-TNF-α (2.6 µg/mL in TBS, 0.02% Tween-20, 0.2% BSA), washed, and air-dried. The captured biotin-TNF-α was detected by Cy3-labeled anti-biotin monoclonal antibody (Sigma) using a ScanArray 5000 system (GSI Lumonics). For mass spectroscopy detection, RNA-$^{10}$Fn3 fusion of the T09.12 variant (FIG. 24B) and wild-type $^{10}$Fn3 (FIG. 24C) was treated with RNase A to generate a fusion between the protein and the DNA linker. The resulting DNA-linked protein was hybridized to a glass coverslip arrayed with an immobilized oligonucleotide complementary to the DNA linker (FIGS. 24B and 24C; no fusion was applied in FIG. 24D). After washing, the above surfaces were exposed to TNF-α (1.5 mg/mL in 90% v/v PBS/10% fetal bovine serum). The dried chip was spotted with MALDI matrix and analyzed with a Voyager DE MALDI-TOF mass spectrometer (PerSeptive Biosystems). A signal at 17.4 kD, which corresponded to the expected molecular mass of monomeric TNF-α, was detected on the 200 µm features that contained T09.12 protein (FIG. 24A), but not on the features that contained wild-type $^{10}$Fn3 (FIG. 24B) nor on the features that did not contain DNA-protein fusion (FIG. 24C).

$K_d$ of the Selected TNF-α Binding Clones

Dissociation constants were determined for all the clones that were represented more than once in the two pools generated after nine and after ten rounds of selection, as well as for the only clone that originated from the $BC_{wt}$-$DE_{wt}$-$FG_r$ library (clone T09.08).

To determine these binding constants, biotinylated TNF-α was prepared using the NHS-LC-LC-Biotin reagent supplied by Pierce (Rockford, Ill.). MALDI-TOF mass spectrometry was used to estimate that more than 80% of the monomeric TNF-α, and hence more than 99% of the trimer, was biotinylated.

For the R9 and R10 pools (and the R14 and M12 pools discussed below), as well as for the characterized clones derived from these two pools, eleven samples of 0.25 nM, in vitro-translated, $^{35}$S-methionine-labeled free protein were incubated with the biotinylated TNF-α at a concentration between 17 pM and 23 nM, in 200 µL 10 mM HEPES, pH 7.4, 150 mM NaCl, 1% BSA, 0.02% Triton, for one hour at room temperature. Subsequently, each sample was loaded on a pre-soaked, SAM$^{2R}$ Biotin Capture Membrane (Promega, Madison, Wis.) using a 96 well, Easy-Titer™ ELIFA system (Pierce). Under vacuum, each spot was washed with 200 µL of HBS pH 7.4, 1% BSA, 0.05% Triton; next the entire membrane was rinsed in the buffer and air-dried. The membrane was exposed with a Storage Phosphor Screen (Molecular Dynamics, Sunnyvale, Calif.) overnight, and the intensities of the resulting individual spots were quantified using a STORM 860 phosphoimager with the ImageQuaNT densitometry program (Molecular Dynamics). The $K_d$ of the binding was determined by fitting the equilibrium equation to the resulting binding curve (KaleidaGraph, Synergy Software); the error of the experiment was estimated from 2–4 independent experiments.

In these studies, the $K_d$ values were found to be in the narrow range of 1–24 nM (Table 1). The T09.12 and T10.06 clones, which contained the most commonly isolated sequences in two loops each, have the low $K_d$ of 4 and 2 nM, respectively; on the other hand, a number of clones with less frequently seen loops, such as clones T09.07 and T10.15, showed similarly tight binding.

A sample comparison of TNF-α binding between free protein and the cDNA/mRNA-protein complex derived from the same sequence showed that the two dissociation constants were within experimental error of each other, a property of the system that makes it possible to use the cDNA/mRNA-protein complex to select for target-binding properties of the protein itself.

High-Stringency Selection of TNF-α Binding Clones

Despite the duplicate clones isolated, the TNF-α-binding pools after nine and after ten rounds of selection contained numerous different clones, i.e., 38 different sequences in 61 clones sampled. Therefore, further selection, with more stringent binding requirements, was undertaken to recover a subset of these clones with superior TNF-α binding properties. Consequently, four further rounds of selections (R11–R14) were conducted in solution, where the concentration of the target was controlled more easily. The concentration of TNF-α was limited to 0.5 nM and the concentration of DNA/mRNA-$^{10}$Fn3 pool to 0.1 nM; in addition, the length and the temperature of the washes of the $^{10}$Fn3/TNF-α complex bound to streptavidin-coated paramagnetic beads were increased.

Specifically, these selections were carried out as follows. For rounds 11–13, 0.1 nM DNA/mRNA-$^{10}$Fn3 fusion library, which had been made as described above, was pre-cleared by tumbling for 1 hour at 4° C. with 100 µL of Dynabeads® M-280 (streptavidin-coated paramagnetic beads; Dynal, Lake Success, N.Y.) that had been pre-blocked in Binding Buffer. The resulting pre-cleared fusion mixture was combined with 0.5 nM biotinylated TNF-α in 300 µL of the above Binding Buffer, and the complex incubated at 4° C. for 1 hour. Next, 100 µl of resuspended Dynabeads® M-280 Streptavidin at 1.3 g/cm$^3$, which had been blocked by overnight incubation in Binding Buffer, were added to the mixture and incubated at 4° C., with tumbling, for 45 additional minutes. The paramagnetic beads were separated from the supernatant on a Dynal MPC-S rack, the supernatant was removed, and the beads were washed with the Binding Buffer for 1, 15, and 30 minutes in the case of R11 and R12, or for 1 minute, followed by nine ten-minute washes in the case of R13–R14. DNA was eluted from the washed DNA/mRNA-$^{10}$Fn3:TNF-α-biotin:streptavidin-bead complexes with two washes of 100 µL 0.1 M KOH, and treated as described above for the column-based selection to produce the next generation DNA/mRNA-$^{10}$Fn3 fusion library. Round 14 differed from R11–R13 in that the selection was performed at 30° C. and in the presence of an additional 150 mM NaCl. Except for the elevated temperature, the sequence of washes was the same for R14 as for R13.

Twenty-two clones derived from the DNA eluted after four further rounds of selection (R14) were picked at random and found to represent 15 different loop sequences (Table 2; full sequences in FIG. 25). The clone T10.06, isolated previously from R10 as described above, was picked eight separate times, whereas the remaining sequences, including T09.31, which had been isolated from the R9 pool, were found in one isolate each. Similar to the isolates from rounds nine and ten, the R14 clones examined showed a preference (18 of 22 clones) for the PWA/G sequence in the DE loop, and four new, non-wild-type DE sequences were revealed.

Whereas the apparent average $K_d$ values of the R14 free protein pool, 3 nM, is similar to those measured for the pools after nine and ten rounds (4 and 6 nM, respectively), several $K_d$ values of the clones isolated from the R14 pool were an order of magnitude lower than the lowest values observed in the R9 and R10 pools (Table 2). The clones that bound TNF-α most tightly, T14.07 and T14.25, had a $K_d$ of 90 pmol. Thus, the conditions used in the last four rounds of selections were stringent enough to favor $^{10}$Fn3 molecules with subnanomolar $K_d$, but not so stringent as to eliminate such molecules.

Mutagenic Affinity Maturation

As discussed above, the selections described herein may also be combined with mutagenesis after all or a subset of the selection steps to further increase library diversity. In one parallel selection strategy, error-prone PCR was incorporated into the amplification of DNA between rounds (Cadwell and Joyce, PCR Methods Appl 2:28 (1992)). This technique was carried out beginning with the diverse DNA pool eluted after R8 above. This pool was amplified using error-prone PCR, with the pool divided into seven equal parts and mutagenized at the target frequency of 0.8%, 1.6%, 2.4%, 3.2%, 4.0%, 4.8%, and 5.6%. The seven PCR reactions were combined, and cDNA/RNA-protein fusion was made from the mixture and subjected to a round of selection in solution. Before the second mutagenic round, M10, error-prone PCR was performed in three separate reactions, at 0.8%, 1.6%, and 2.4%. The two remaining rounds, M11 and M12, were performed using standard Taq PCR. Except for mutagenesis, the selection conditions for M9-M12 were the same as for R11–R14. The twenty M12 clones tested showed tighter binding to TNF-α than the clones selected using the two earlier selection protocols (Table 3; full sequences in FIG. 25); the tightest binding of TNF-α was seen in M12.04, and had the observed $K_d$ of 20 pM. These results demonstrated that low-level, random mutagenesis late in a selection can improve both the binding affinity of selected antibody mimics (20 pM vs. 90 pM) and the speed with which they can be selected (12 rounds vs. 14 rounds). In addition, the frequency of tight binders in this mutagenesis approach was observed to be about 5%, whereas the frequency is approximately 3% in other selections.

Superiority of Fn Binders

The selection of $^{10}$Fn3 variants capable of binding to TNF-α, performed using covalent mRNA-protein fusion as the unit of selection, was won by molecules with dissociation constants as low as 20 pM. These $K_d$ values compared favorably against the standards of selection of others that used other antibody mimic scaffolds and selection methods. Consequently, the $^{10}$Fn3-based scaffold and covalent mRNA-protein fusion-based in vitro selection method may be utilized for the development of antibody mimics against a broad range of antigens. In addition, the subnanomolar, TNF-α-binding $^{10}$Fn3 variants described herein represent potential therapeutic, research, and diagnostic agents. Moreover, since this in vitro selection method can be automated, such a combination of scaffold and selection methods have applications on the genomic scale.

One of the factors that contributed to the success of the present selection was the randomization of all three CDR-like loops of $^{10}$Fn3; similar libraries which contained only one or two randomized loops were less likely to include tight binders than the library with three randomized, CDR-like loops.

In the selection reported above, the randomized loops remained the length of the corresponding, wild-type $^{10}$Fn3 loops. To generate further library diversity, the length of the loops as well as their sequences may be varied, to incorporate favorable mutations in the $^{10}$Fn3 beta-sheet into the wild-type scaffold used for library construction, and to create libraries with randomized beta-sheet scaffolds which will allow selection of structures even more successful at mimicking antibodies.

Selections similar to those described herein may be carried out with any other binding species target (for example, IL-1 or IL-13).

Animal Studies

Wild-type $^{10}$Fn3 contains an integrin-binding tripepetide motif, Arginine 78-Glycine 79-Aspartate 80 (the "RGD motif") at the tip of the FG loop. In order to avoid integrin binding and a potential inflammatory response based on this tripeptide in vivo, a mutant form of $^{10}$Fn3 was generated that contained an inert sequence, Serine 78-Glycine 79-Glutamate 80 (the "SGE mutant"), a sequence which is found in the closely related, wild-type $^{11}$Fn3 domain. This SGE mutant was expressed as an N-terminally $His_6$-tagged, free protein in E. coli, and purified to homogeneity on a metal chelate column followed by a size exclusion column.

In particular, the DNA sequence encoding $His_6$-$^{10}$Fn3 (SGE) was cloned into the pET9a expression vector and transformed into BL21 DE3 pLysS cells. The culture was then grown in LB broth containing 50 μg/mL kanamycin at 37° C., with shaking, to $A_{560}$=1.0, and was then induced with 0.4 mM IPTG. The induced culture was further incubated, under the same conditions, overnight (14–18 hours); the bacteria were recovered by standard, low speed centrifugation. The cell pellet was resuspended in 1/50 of the original culture volume of lysis buffer (50 mM Tris 8.0, 0.5 M NaCl, 5% glycerol, 0.05% Triton X-100, and 1 mM PMSF), and the cells were lysed by passing the resulting paste through a Microfluidics Corporation Microfluidizer M110-EH, three times. The lysate was clarified by centrifugation, and the supernatant was filtered through a 0.45 μm filter followed by filtration through a 0.2 μm filter. 100 mL of the clarified lysate was loaded onto a 5 mL Talon cobalt column (Clontech, Palo Alto, Calif.), washed by 70 mL of lysis buffer, and eluted with a linear gradient of 0–30 mM imidazole in lysis buffer. The flow rate through the column through all the steps was 1 mL/min. The eluted protein was concentrated 10-fold by dialysis (MW cutoff=3,500) against 15,000–20,000 PEG. The resulting sample was dialysed into buffer 1 (lysis buffer without the glycerol), then loaded, 5 mL at a time, onto a 16×60 mm Sephacryl 100 size exclusion column equilibrated in buffer 1. The column was run at 0.8 mL/min, in buffer 1; all fractions that contained a protein of the expected MW were pooled, concentrated 10× as described above, then dialyzed into PBS. Endotoxin screens and animal studies were performed on the resulting sample (Toxikon; MA).

The endotoxin levels in the samples examined to date have been below the detection level of the assay. In a preliminary animal toxicology study, this protein was injected into two mice at the estimated 100× therapeutic dose of 2.6 mg/mouse. The animals survived the two weeks of the study with no apparent ill effects. These safety results support the use of $^{10}$Fn3 incorporated into an IV drug.

Alternative Constructs for In Vivo Use

Figure 11:
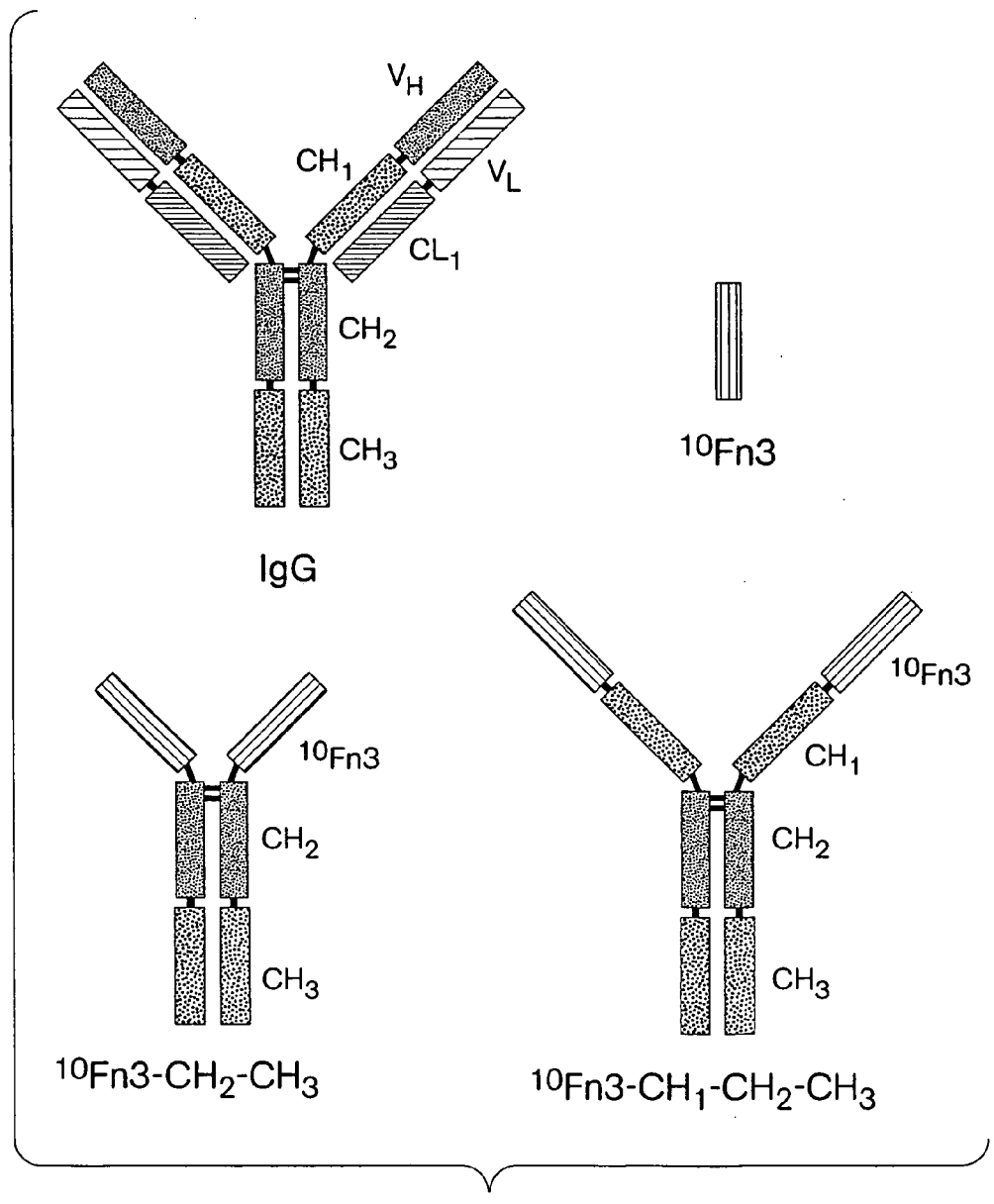
FIG. 11 is a series of schematic representations showing IgG, $^{10}$Fn3, Fn-CH$_1$—CH$_2$—CH$_3$, and Fn-CH$_2$—CH$_3$ (clockwise from top left).
Figure 12:
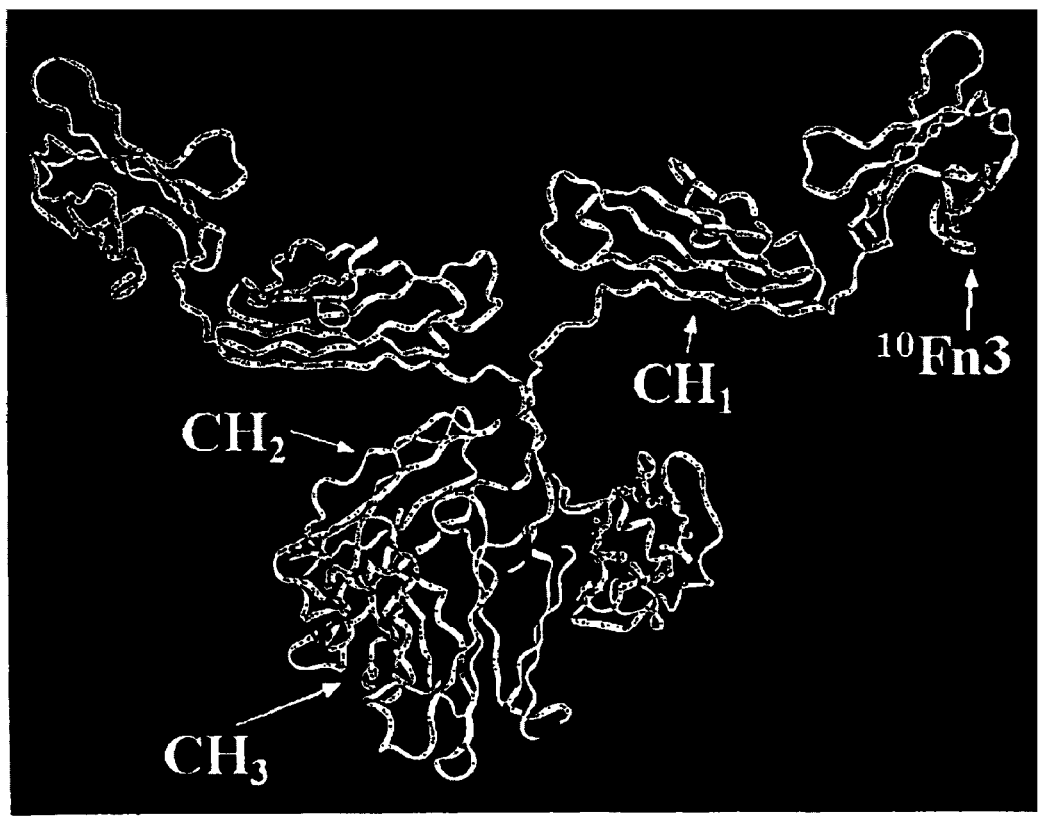
FIG. 12 is a photograph showing a molecular model of Fn-CH$_1$—CH$_2$—CH$_3$ based on known three-dimensional structures of IgG (X-ray crystallography) and $^{10}$Fn3 (NMR and X-ray crystallography).

To extend the half life of the 8 kD $^{10}$Fn3 domain, a larger molecule has also been constructed that mimics natural antibodies. This $^{10}$Fn3-F$_c$ molecule contains the —CH$_1$—CH$_2$—CH$_3$ (FIG. 11) or —CH$_2$—CH$_3$ domains of the IgG constant region of the host; in these constructs, the $^{10}$Fn3 domain is grafted onto the N-terminus in place of the IgG V$_H$ domain (FIGS. 11 and 12). Such antibody-like constructs are to improve the pharmacokinetics of the protein as well as its ability to harness the natural immune response.

In order to construct the murine form of the $_{10}$Fn3-CH$_1$—CH$_2$—CH$_3$ clone, the —CH$_1$—CH$_2$—CH$_3$ region was first amplified from a mouse liver spleen cDNA library (Clontech), then ligated into the pET25b vector. The primers used in the cloning were 5' Fc Nest and 3' 5 Fc Nest, and the primers used to graft the appropriate restriction sites onto the ends of the recovered insert were 5'Fc HIII and 3'Fc Nhe:

```
5' Fc Nest
5' GCG GCA GGG TTT GCT TAC TGG GGC    (SEQ ID NO: 15)

CAA GGG 3';

3' Fc Nest
5' GGG AGG GGT GGA GGT AGG TCA CAG    (SEQ ID NO: 16)

TCC 3';

3' Fc Nhe
5' TTT GCT AGC TTT ACC AGG AGA GTG    (SEQ ID NO: 17)

GGA GGC 3';
and

5' Fc HIII
5' AAA AAG CTT GCC AAA ACG ACA CCC    (SEQ ID NO: 18)

CCA TCT GTC 3'.
```

Further PCR was used to remove the CH$_1$ region from this clone and to create the Fc part of the shorter, $_{10}$Fn3-CH$_2$—CH$_3$ clone. The sequence encoding $^{10}$Fn3 was spliced onto the 5' end of each clone; either the wild type $^{10}$Fn3 cloned from the same mouse spleen cDNA library or a modified $^{10}$Fn3 obtained by mutagenesis or randomization of the molecules can be used. The oligonucleotides used in the cloning of murine wild-type $^{10}$Fn3 were:

```
Mo 5PCR-NdeI:
5' CATATGGTTTCTGATATTCCGAGAGATCTG    (SEQ ID NO: 19)

GAG 3';

Mo5PCR-His-NdeI (for an alternative
N-terminus
with the His₆ purification tag):
5' CAT ATG CAT CAC CAT CAC CAT CAC    (SEQ ID NO: 20)

GTT TCT GAT ATT CCG AGA G 3';
``` and

```
Mo3PCR-EcoRI:
5' GAATTCCTATGTTTTATAATTGATGGA       (SEQ ID NO: 21)

AAC 3'.
```

The human equivalents of the clones are constructed using the same strategy with human oligonucleotide sequences.

Antibody Mimics in Protein Chip Applications

Any of the antibody mimics described herein may be immobilized on a solid support, such as a microchip. The suitability of the present scaffolds, for example, the $^{10}$Fn3 scaffold, for protein chip applications is the consequence of (1) their ability to support many binding functions which can be selected rapidly on the bench or in an automated setup, and (2) their superior biophysical properties.

The versatile binding properties of $^{10}$Fn3 are a function of the loops displayed by the Fn3 immunoglobulin-like, beta sandwich fold. As discussed above, these loops are similar to the complementarity determining regions of antibody variable domains and can cooperate in a way similar to those antibody loops in order to bind antigens. In our system, $^{10}$Fn3 loops BC (for example, residues 21–30), DE (for example, residues 51–56), and FG (for example, residues 76–87) are randomized either in sequence, in length, or in both sequence and length in order to generate diverse libraries of mRNA-$^{10}$Fn3 fusions. The binders in such libraries are then enriched based on their affinity for an immobilized or tagged target, until a small population of high affinity binders are generated. Also, error-prone PCR and recombination can be employed to facilitate affinity maturation of selected binders. Due to the rapid and efficient selection and affinity maturation protocols, binders to a large number of targets can be selected in a short time.

As a scaffold for binders to be immobilized on protein chips, the $^{10}$Fn3 domain has the advantage over antibody fragments and single-chain antibodies of being smaller and easier to handle. For example, unlike single-chain scaffolds or isolated variable domains of antibodies, which vary widely in their stability and solubility, and which require an oxidizing environment to preserve their structurally essential disulfide bonds, $^{10}$Fn3 is extremely stable, with a melting temperature of 110° C., and solubility at a concentration >16 mg/mL. The $^{10}$Fn3 scaffold also contains no disulfides or free cysteines; consequently, it is insensitive to the redox potential of its environment. A further advantage of $^{10}$Fn3 is that its antigen-binding loops and N-terminus are on the edge of the beta-sandwich opposite to the C-terminus; thus the attachment of a $^{10}$Fn3 scaffold to a chip by its C-terminus aligns the antigen-binding loops, allowing for their greatest accessibility to the solution being assayed. Since $^{10}$Fn3 is a single domain of only 94 amino acid residues, it is also possible to immobilize it onto a chip surface at a higher density than is used for single-chain antibodies, with their approximately 250 residues. In addition, the hydrophilicity of the $^{10}$Fn3 scaffold, which is reflected in the high solubility of this domain, minimizes unwanted binding of $^{10}$Fn3 to a chip surface.

The stability of the $^{10}$Fn3 scaffold as well as its suitability for library formation and selection of binders are likely to be shared by the large, Fn3-like class of protein domains with an immunoglobulin-like fold, such as the domains of tenascin, N-cadherin, E-cadherin, ICAM, titin, GCSF-R, cytokine receptor, glycosidase inhibitor, and antibiotic chromoprotein. The key features shared by all such domains are a stable framework provided by two beta-sheets, which are packed against each other and which are connected by at least three solvent-accessible loops per edge of the sheet; such loops can be randomized to generate a library of potential binders without disrupting the structure of the framework (as described above). In addition, as with $^{10}$Fn3, any of these loops (or similar loops from other proteins) may be immobilized alone or in combination with other loops onto a solid support surface.

Immobilization of Fn3-Based Antibody Mimics

To immobilize antibody mimics, such as Fn3-based antibody mimics, to a chip surface, a number of exemplary techniques may be utilized. For example, such antibody mimics may be immobilized as RNA-protein fusions by Watson-Crick hybridization of the RNA moiety of the fusion to a base complementary DNA immobilized on the chip surface (as described, for example, in Addressable Protein Arrays, U.S. Ser. No. 60/080,686; U.S. Ser. No. 09/282,734; and WO 99/51773; and Methods for Encoding and Sorting In Vitro Translated Proteins, U.S. Ser. No. 60/151,261 and U.S. Ser. No. 09/648,040). Alternatively, antibody mimics can be immobilized as free proteins directly on a chip surface. Manual as well as robotic devices may be used for deposition of the antibody mimics on the chip surface. Spotting robots can be used for deposition of antibody mimics with high density in an array format (for example, by the method of Lueking et al., Anal Biochem. 1999 May 15;270(1):103–11). Different methods may also be utilized for anchoring the antibody mimic on the chip surface. A number of standard immobilization procedures may be used including those described in Methods in Enzymology (K. Mosbach and B. Danielsson, eds.), vols. 135 and 136, Academic Press, Orlando, Fla., 1987; Nilsson et al., Protein Expr. Purif. 1997 October;11(1):1–16; and references therein. Oriented immobilization of antibody mimics can help to increase the binding capacity of chip-bound antibody mimics. Exemplary approaches for achieving oriented coupling are described in Lu et al., The Analyst (1996), vol. 121, p. 29R–32R; and Turkova, J Chromatogr B Biomed Sci App. 1999 Feb. 5;722(1–2):11–31. In addition, any of the methods described herein for anchoring antibody mimics to chip surfaces can also be applied to the immobilization of antibody mimics on beads, or other supports.

Target Protein Capture and Detection

Selected populations of scaffold-binders may be used for detection and/or quantitation of analyte targets, for example, in samples such as biological samples. To carry out this type of diagnostic assay, selected scaffold-binders to targets of interest are immobilized on an appropriate support to form multi-featured protein chips. Next, a sample is applied to the chip, and the components of the sample that associate with the binders are identified based on the target-specificity of the immobilized binders. Using this technique, one or more components may be simultaneously identified or quantitated in a sample (for example, as a means to carry out sample profiling).

Methods for target detection allow measuring the levels of bound protein targets and include, without limitation, radiography, fluorescence scanning, mass spectroscopy (MS), and surface plasmon resonance (SPR). Autoradiography using a phosphorimager system (Molecular Dynamics, Sunnyvale, Calif.) can be used for detection and quantification of target protein which has been radioactively labeled, e.g., using $^{35}$S methionine. Fluorescence scanning using a laser scanner (see below) may be used for detection and quantification of fluorescently labeled targets. Alternatively, fluorescence scanning may be used for the detection of fluorescently labeled ligands which themselves bind to the target protein (e.g., fluorescently labeled target-specific antibodies or fluorescently labeled streptavidin binding to target-biotin, as described below).

Mass spectroscopy can be used to detect and identify bound targets based on their molecular mass. Desorption of bound target protein can be achieved with laser assistance directly from the chip surface as described below. Mass detection also allows determinations, based on molecular mass, of target modifications including post-translational modifications like phosphorylation or glycosylation. Surface plasmon resonance can be used for quantification of bound protein targets where the scaffold-binder(s) are immobilized on a suitable gold-surface (for example, as obtained from Biacore, Sweden).

Described below are exemplary schemes for selecting binders (in this case, Fn-binders specific for the protein, TNF-α) and the use of those selected populations for detection on chips. This example is provided for the purpose of illustrating the invention, and should not be construed as limiting.

Selection of TNF-α Binders Based on $^{10}$Fn3 Scaffold

In one exemplary use for scaffold selection on chips, an $^{10}$Fn3-based selection was performed against TNF-α, using a library of human $^{10}$Fn3 variants with randomized loops BC, DE, and FG. The library was constructed from three DNA fragments, each of which contained nucleotide sequences that encoded approximately one third of human $^{10}$Fn3, including one of the randomized loops. The DNA sequences that encoded the loop residues listed above were rebuilt by oligonucleotide synthesis, so that the codons for the residues of interest were replaced by $(NNS)_n$, where N represents any of the four deoxyribonucleotides (A, C, G, or T), and S represents either C or G. The C-terminus of each fragment contained the sequence for the FLAG purification tag.

Once extended by Kienow, each DNA fragment was transcribed, ligated to a puromycin-containing DNA linker, and translated in vitro, as described by Szostak et al. (Roberts and Szostak, Proc. Natl. Acad. Sci USA 94:12297, 1997; Szostak et al., U.S. Ser. No. 09/007,005 and U.S. Ser. No. 09/247,190; Szostak et al., WO98/31700), to generate an mRNA-peptide fusion, which was then reverse-transcribed into a DNA-mRNA-peptide fusion. The binding of the FLAG-tagged peptide to M2 agarose separated full-length fusion molecules from those containing frameshifts or superfluous stop codons; the DNA associated with the purified full-length fusion was amplified by PCR, then the three DNA fragments were cut by Ear I restriction endonuclease and ligated to form the full length template. The template was transcribed, ligated to puromycin-containing DNA linkers, and translated to generate a $^{10}$Fn3-RNA/cDNA library, which was then reverse-transcribed to yield the DNA-mRNA-peptide fusion library which was subsequently used in the selection.

Selection for TNF-α binders took place in 50 mM HEPES, pH 7.4, 0.02% Triton-X, 0.1 mg/mL salmon sperm DNA. The PROfusion™ library was incubated with Sepharose-immobilized TNF-α; after washing, the DNA associated with the tightest binders was eluted with 0.1 M KOH, amplified by PCR, and transcribed, ligated, translated, and reverse-transcribed into the starting material for the next round of selection.

Ten rounds of such selection were performed (as shown in FIG. 13); they resulted in a PROfusion™ pool that bound to TNF-α-Sepharose with the apparent average $K_d$ of 120 nM. Specific clonal components of the pool that were characterized showed TNF-α binding in the range of 50–500 nM.

Immobilization, Target Protein Capture, and MALDI-TOF Detection

As a first step toward immobilizing Fn3 fusions to a chip surface, an oligonucleotide capture probe was prepared with an automated DNA synthesizer (PE BioSystems Expedite 8909) using the solid-support phosphoramidite approach. All reagents were obtained from Glen Research. Synthesis was initiated with a solid support containing a disulfide bond to eventually provide a 3'-terminal thiol functionality. The first four monomers to be added were hexaethylene oxide units, followed by 20 T monomers. The 5'-terminal DMT group was not removed. The capture probe was cleaved from the solid support and deprotected with ammonium hydroxide, concentrated to dryness in a vacuum centrifuge, and purified by reverse-phase HPLC using an acetonitrile gradient in triethylammonium acetate buffer. Appropriate fractions from the HPLC were collected, evaporated to dryness in a vacuum centrifuge, and the 5'-terminal DMT group was removed by treatment with 80% AcOH for 30 minutes. The acid was removed by evaporation, and the oligonucleotide was then treated with 100 mM DTT for 30 minutes to cleave the disulfide bond. DTT was removed by repeated extraction with EtOAc. The oligonucleotide was ethanol precipitated from the remaining aqueous layer and checked for purity by reverse-phase HPLC.

The 3'-thiol capture probe was adjusted to 250 μM in degassed 1×PBS buffer and applied as a single droplet (75 μL) to a 9×9 mm gold-coated chip (Biacore) in an argon-flushed chamber containing a small amount of water. After 18 hours at room temperature, the capture probe solution was removed, and the functionalized chip was washed with 50 mL 1×PBS buffer (2×for 15 minutes each) with gentle agitation, and then rinsed with 50 mL water (2×for 15 minutes each) in the same fashion. Remaining liquid was carefully removed and the functionalized chips were either used immediately or stored at 4° C. under argon.

About 1 pmol of $^{10}$Fn3 fusion pool from the Round 10 TNF-α selection (above) was treated with RNAse A for several hours, adjusted to 5×SSC in 70 μL, and applied to a functionalized gold chip from above as a single droplet. A 50 μL volume gasket device was used to seal the fusion mixture with the functionalized chip, and the apparatus was continuously rotated at 4° C. After 18 hours the apparatus was disassembled, and the gold chip was washed with 50 mL 5×SSC for 10 minutes with gentle agitation. Excess liquid was carefully removed from the chip surface, and the chip was passivated with a blocking solution (1×TBS+0.02% Tween-20+0.25% BSA) for 10 minutes at 4° C. Excess liquid was carefully removed, and a solution containing 500 μg/mL TNF-α in the same composition blocking solution was applied to the chip as a single droplet and incubated at 4° C. for two hours with occasional mixing of the droplet via Pipetman. After removal of the binding solution, the chip was washed for 5 minutes at 4° C. with gentle agitation (50 mL 1×TBS+0.02% Tween-20) and then dried at room temperature. A second chip was prepared exactly as described above, except fusion was not added to the hybridization mix.

Next, MALDI-TOF matrix (15 mg/mL 3,5-dimethoxy-4-hydroxycinnamic acid in 1:1 ethanol/10% formic acid in water) was uniformly applied to the gold chips with a high-precision 3-axis robot (MicroGrid, BioRobotics). A 16-pin tool was used to transfer the matrix from a 384-well microtiter plate to the chips, producing 200 micron diameter features with a 600 micron pitch. The MALDI-TOF mass spectrometer (Voyager DE, PerSeptive Biosystems) instrument settings were as follows: Accelerating Voltage=25k, Grid Voltage=92%, Guide Wire Voltage=0.05%, Delay=200 on, Laser Power=2400, Low Mass Gate=1500, Negative Ions=off. The gold chips were individually placed on a MALDI sample stage modified to keep the level of the chip the same as the level of the stage, thus allowing proper flight distance. The instrument's video monitor and motion control system were used to direct the laser beam to individual matrix features.

Figure 14:
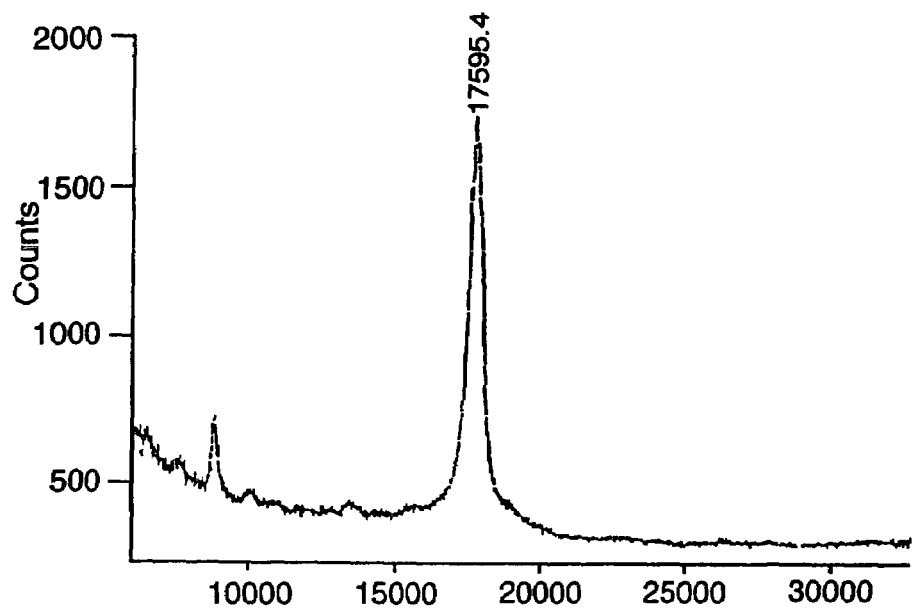
FIGS. 14 and 15 are graphs illustrating TNF-α binding by TNF-α Fn-binders. In particular, these figures show mass spectra data obtained from a $^{10}$Fn3 fusion chip and non-fusion chip, respectively.
Figure 15:
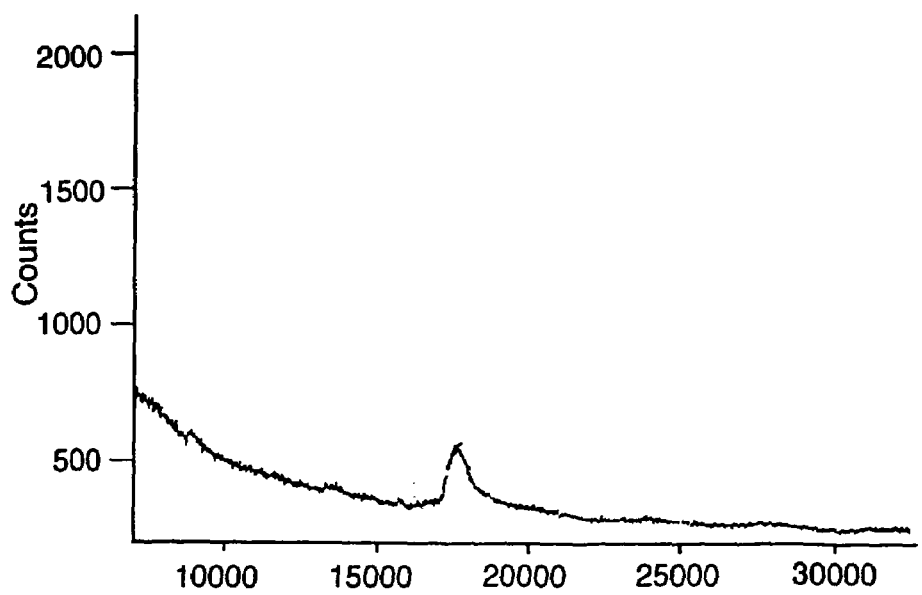

FIGS. 14 and 15 show the mass spectra from the $^{10}$Fn3 fusion chip and the non-fusion chip, respectively. In each case, a small number of 200 micron features were analyzed to collect the spectra, but FIG. 15 required significantly more acquisitions. The signal at 17.4 kDa corresponds to TNF-α monomer.

Immobilization, Target Protein Capture, and Fluorescence Detection

Pre-cleaned 1×3 inch glass microscope slides (Goldseal, #3010) were treated with Nanostrip (Cyantek) for 15 minutes, 10% aqueous NaOH at 70° C. for 3 minutes, and 1% aqueous HCl for 1 minute, thoroughly rinsing with deionized water after each reagent. The slides were then dried in a vacuum desiccator over anhydrous calcium sulfate for several hours. A 1% solution of aminopropyltrimethoxysilane in 95% acetone/5% water was prepared and allowed to hydrolyze for 20 minutes. The glass slides were immersed in the hydrolyzed silane solution for 5 minutes with gentle agitation. Excess silane was removed by subjecting the slides to ten 5-minute washes, using fresh portions of 95% acetone/5% water for each wash, with gentle agitation. The slides were then cured by heating at 110° C. for 20 minutes. The silane treated slides were immersed in a freshly prepared 0.2% solution of phenylene 1,4-diisothiocyanate in 90% DMF/10% pyridine for two hours, with gentle agitation. The slides were washed sequentially with 90% DMF/10% pyridine, methanol, and acetone. After air drying, the functionalized slides were stored at 0° C. in a vacuum desiccator over anhydrous calcium sulfate. Similar results were obtained with commercial amine-reactive slides (3-D Link, Surmodics).

Oligonucleotide capture probes were prepared with an automated DNA synthesizer (PE BioSystems Expedite 8909) using conventional phosphoramidite chemistry. All reagents were from Glen Research. Synthesis was initiated with a solid support bearing an orthogonally protected amino functionality, whereby the 3'-terminal amine is not unmasked until final deprotection step. The first four monomers to be added were hexaethylene oxide units, followed by the standard A, G, C and T monomers. All capture oligo sequences were cleaved from the solid support and deprotected with ammonium hydroxide, concentrated to dryness, precipitated in ethanol, and purified by reverse-phase HPLC using an acetonitrile gradient in triethylammonium acetate buffer. Appropriate fractions from the HPLC were collected, evaporated to dryness in a vacuum centrifuge, and then coevaporated with a portion of water.

The purified, amine-labeled capture oligos were adjusted to a concentration of 250 μM in 50 mM sodium carbonate buffer (pH 9.0) containing 10% glycerol. The probes were spotted onto the amine-reactive glass surface at defined positions in a 5×5×6 array pattern with a 3-axis robot (MicroGrid, BioRobotics). A 16-pin tool was used to transfer the liquid from 384-well microtiter plates, producing 200 micron features with a 600 micron pitch. Each sub-grid of 24 features represents a single capture probe (i.e., 24 duplicate spots). The arrays were incubated at room temperature in a moisture-saturated environment for 12–18 hours. The attachment reaction was terminated by immersing the chips in 2% aqueous ammonium hydroxide for five minutes with gentle agitation, followed by rinsing with distilled water (3× for 5 minutes each). The array was finally soaked in 10×PBS solution for 30 minutes at room temperature, and then rinsed again for 5 minutes in distilled water.

Specific and thermodynamically isoenergetic sequences along the $^{10}$Fn3 mRNA were identified to serve as capture points to self-assemble and anchor the $^{10}$Fn3 protein. The software program HybSimulator v4.0 (Advanced Gene Computing Technology, Inc.) facilitated the identification and analysis of potential capture probes. Six unique capture probes were chosen and printed onto the chip, three of which are complementary to common regions of the $^{10}$Fn3 fusion pool's mRNA (CP3', CP5', and CPflag). The remaining three sequences (CPneg1, CPneg2, and CPneg3) are not complementary and function in part as negative controls. Each of the capture probes possesses a 3'-amino terminus and four hexaethylene oxide spacer units, as described above. The following is a list of the capture probe sequences that were employed (5'→3'):

```
CP3':    TGTAAATAGTAATTGTCCC      (SEQ ID NO: 22)

CP5':    TTTTTTTTTTTTTTTTTTTT     (SEQ ID NO: 23)

CPneg1:  CCTGTAGGTGTCCAT          (SEQ ID NO: 24)

CPflag:  CATCGTCCTTGTAGTC         (SEQ ID NO: 25)

CPneg2:  CGTCGTAGGGGTA            (SEQ ID NO: 26)

CPneg3:  CAGGTCTTCTTCAGAGA        (SEQ ID NO: 27)
```

About 1 pmol of $^{10}$Fn3 fusion pool from the Round 10 TNF-α selection was adjusted to 5×SSC containing 0.02% Tween-20 and 2 mM vanadyl ribonucleotide complex in a total volume of 350 μL. The entire volume was applied to the microarray under a 400 μL gasket device and the assembly was continuously rotated for 18 hours at room temperature. After hybridization the slide was washed sequentially with stirred 500 mL portions of 5×SSC, 2.5×SSC, and 1×SSC for 5 minutes each. Traces of liquid were removed by centrifugation and the slide was allowed to air-dry.

Recombinant human TNF-α (500 μg, lyophilized, from PreproTech) was taken up in 230 μL 1×PBS and dialyzed against 700 mL stirred 1×PBS at 4° C. for 18 hours in a Microdialyzer unit (3,500 MWCO, Pierce). The dialyzed TNF-α was treated with EZ-Link NHS-LC-LC biotinylation reagent (20 μg, Pierce) for 2 hours at 0° C., and again dialyzed against 700 mL stirred 1×PBS at 4° C. for 18 hours in a Microdialyzer unit (3,500 MWCO, Pierce). The resulting conjugate was analyzed by MALDI-TOF mass spectrometry and was found to be almost completely functionalized with a single biotin moiety.

Each of the following processes was conducted at 4° C. with continuous rotation or mixing. The protein microarray surface was passivated by treatment with 1×TBS containing 0.02% Tween-20 and 0.2% BSA (200 μL) for 60 minutes. Biotinylated TNF-α (100 nM concentration made up in the passivation buffer) was contacted with the microarray for 120 minutes. The microarray was washed with 1×TBS containing 0.02% Tween-20 (3×50 mL, 5 minutes each wash). Fluorescently labeled streptavidin (2.5 μg/mL Alexa 546-streptavidin conjugate from Molecular Probes, made up in the passivation buffer) was contacted with the microarray for 60 minutes. The microarray was washed with 1×TBS containing 0.02% Tween-20 (2×50 mL, 5 minutes each wash) followed by a 3 minute rinse with 1×TBS. Traces of liquid were removed by centrifugation, and the slide was allowed to air-dry at room temperature.

Fluorescence laser scanning was performed with a GSI Lumonics ScanArray 5000 system using 10 μM pixel resolution and preset excitation and emission wavelengths for Alexa 546 dye. Phosphorimage analysis was performed with a Molecular Dynamics Storm system. Exposure time was 48 hours with direct contact between the microarray and the phosphor storage screen. Phosphorimage scanning was performed at the 50 micron resolution setting, and data was extracted with ImageQuant v.4.3 software.

Figure 16:
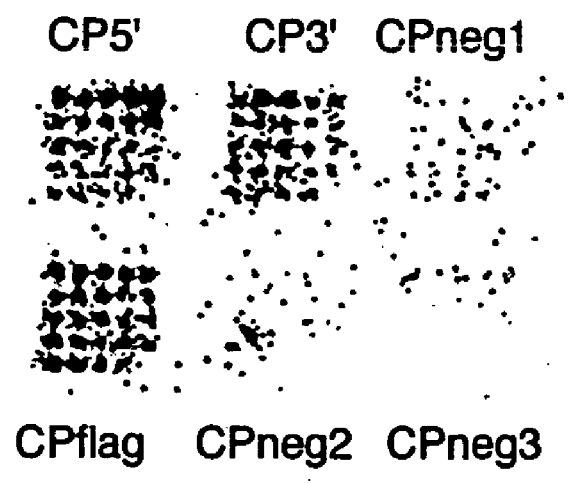
FIGS. 16 and 17 are the phosphorimage and fluorescence scan, respectively, of an $^{10}$Fn3 array, illustrating TNF-α binding.
Figure 17:
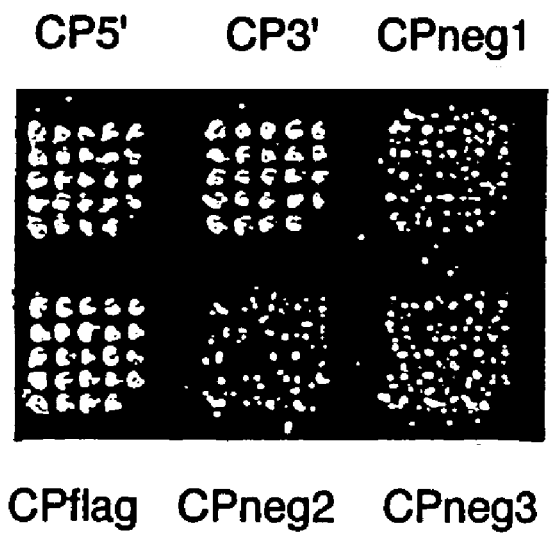

FIGS. 16 and 17 are the phosphorimage and fluorescence scan, respectively, of the same array. The phosphorimage shows where the $^{10}$Fn3 fusion hybridized based on the $^{35}$S methionine signal. The fluorescence scan shows where the labeled TNF-α bound.

OTHER EMBODIMENTS

Other embodiments are within the claims.

All publications, patents, and patent applications mentioned herein are hereby incorporated by reference.

What is claimed is:

1. A non-antibody protein comprising a domain having an immunoglobulin-like fold, said non-antibody protein deriving from a reference protein having an immunoglobulin-like fold by having a mutated amino acid sequence, wherein said domain having an immunoglobulin-like fold has a sequence that is at least 80% identical to the seciuence of SEQ ID NO: 81 and, wherein said non-antibody protein binds with a Kd at least as tight as 1 μM to a compound that is not bound as tightly by said reference protein.

2. The derivative protein of claim 1, said derivative protein binding with a Kd at least as tight as 500 nM.

3. The derivative protein of claim 2, said derivative protein binding with a Kd at least as tight as 100 nM.

4. The derivative protein of claim 3, said derivative protein binding with a Kd at least as tight as 10 nM.

5. The derivative protein of claim 4, said derivative protein binding with Kd at least as tight as 1 nM.

6. The derivative protein of claim 5, said derivative protein binding with a Kd at least as tight as 500 pM.

7. The derivative protein of claim 6, said derivative protein binding with a Kd at least as tight as 100 pM.

8. The derivative protein of claim 7, said derivative protein binding with a Kd at least as tight as 20 pM.

9. The derivative protein of claim 1, wherein said domain having an immunoglobulin-like fold and a sequence that is at least 80% identical to the sequence of SEQ ID NO: 81 contains one, two, or three mutated loops and wherein at least one of said loops contributes to the binding of said derivative protein to said compound.

10. The derivative protein of claim 9, wherein at least two of said loops contribute to said binding of said derivative protein to said compound.

11. The derivative protein of claim 9, wherein three of said loops contribute to said binding of said derivative protein to said compound.

12. The derivative protein of claim 1, wherein said reference protein lacks disulfide bonds.

13. The derivative protein of claim 12, wherein said derivative protein has at least one disulfide bond.

14. The derivative protein of claim 1, wherein said domain having an immunoglobulin-like fold and a sequence that is at least 80% identical to the sequence of SEQ ID NO: 81 has a molecular mass less than 10 kD.

15. The derivative protein of claim 1, wherein said domain having an immunoglobulin-like fold and a sequence that is at least 80% identical to the sequence of SEQ ID NO: 81 has a molecular mass greater than 7.5 kD.

16. The derivative protein of claim 1, wherein said domain having an immunoglobulin-like fold and a sequence that is at least 80% identical to the sequence of SEQ ID NO: 81 has a molecular mass between 7.5–10 kD.

17. The derivative protein of claim 1, wherein said derivative protein is a monomer under physiological conditions.

18. The derivative protein of claim 1, wherein said derivative protein is a dimer under physiological conditions.

19. The derivative protein of claim 1, wherein said reference protein is a naturally-occurring mammalian protein.

20. The derivative protein of claim 1, wherein said domain having an immunoglobulin-like fold and a sequence that is at least 80% identical to the sequence of SEQ ID NO: 81 is mutated and comprises up to 34% mutated amino acids as compared to the immunoglobulin-like fold of said reference protein.

21. The derivative protein of claim 1, said derivative protein being immobilized on a solid support.

22. The derivative protein of claim 21, said derivative protein being part of an array immobilized on a solid support.

23. The derivative protein of claim 21, said solid support being a chip or bead.

24. The derivative protein of claim 1, wherein said derivative protein is derived from a fibronectin or fibronectin dimer.

25. A method of obtaining a derivative non-antibody protein which binds to a compound, said method comprising:

(a) providing a non-antibody scaffold protein comprising a domain having an immunoglobulin-like fold, wherein said scaffold protein does not bind to said compound with a Kd as tight as 1 μM;

(b) generating mutated derivatives of said non-antibody scaffold protein wherein said derivatives comprise a domain having an immunoglobulin-like fold and a sequence that is at least 80% identical to the sequence of SEQ ID NO: 81, thereby producing a library of mutated proteins;

(c) contacting said library with said compound;

(d) selecting from said library at least one derivative protein which binds to said compound with a Kd at least as tight as 1 μM; and (e) optionally repeating steps (b)–(d) substituting for the non-antibody scaffold protein in repeated step (b) the product from the previous step (d).

26. A method for obtaining a non-antibody protein which binds to a compound, said method comprising:

(a) contacting said compound with a candidate protein, said candidate protein being a derivative non-antibody protein comprising a domain having an immunoglobulin-like fold and a sequence that is at least 80% identical to the sequence of SEQ ID NO:81, said non-antibody protein deriving from a reference protein by having a mutated amino acid sequence wherein said non-antibody protein binds with a Kd at least as tight as 1 μM to a compound that is not bound as tightly by said reference protein, wherein said contacting is carried out under conditions that allow compound-protein complex formation; and (b) obtaining, from said complex, said derivative protein which binds to said compound.

27. A method for obtaining a compound which binds to a non-antibody protein, said non-antibody protein comprising a domain having an immunoglobulin-like fold and a sequence that is at least 80% identical to the sequence of SEQ ID NO: 81 and deriving from a reference protein by having a mutated amino acid sequence, wherein said non-antibody protein binds with a Kd at least as tight as 1 µM to a compound that is not bound as tightly by said reference protein, said method comprising:
  (a) contacting said derivative protein with a candidate compound, wherein said contacting is carried out under conditions that allow compound-protein complex formation; and
  (b) obtaining, from said complex, said compound which binds to said derivative proteins.

28. A method for detecting a compound in a sample, said method comprising:
  (a) contacting said sample with a non-antibody protein comprising a domain having an immunoglobulin-like fold and a sequence that is at least 80% identical to the SEQ ID NO: 81, said non-antibody protein deriving from a reference protein by having a mutated amino acid sequence wherein said non-antibody protein binds with a Kd at least as tight as 1 µM to a compound that is not bound as tightly by said reference protein, wherein said contacting is carried out under conditions that allow compound-protein complex formation; and
  (b) detecting said complex, thereby detecting said compound in said sample.

29. A non-antibody protein that binds tumor necrosis factor-α (TNF-α) with a Kd at least as tight as 1 µM, said protein having a sequence that is less than 20% identical to TNF-α receptor and is at least 80% identical to the seciuence of SEQ ID NO: 81.

30. The non-antibody protein of claim 29, wherein said non-antibody protein comprises a mutated fibronectin type III domain and wherein said protein is mutated in the DE, BC, and FG loops.

31. The non-antibody protein of claim 30, wherein said FG loop is the same length as the wild-type FG loop.

32. The non-antibody protein of claim 29, wherein said protein comprises a sequence shown in FIG. 25.

33. A loop structure on a protein, said loop comprising an amino acid sequences that is at least 80% identical to the sequence of SEQ ID NO: 81, wherein said loop binds with a Kd at least as tight as 1 µM to a compound that is not bound as tightly by said reference protein.

* * * * *

SEQUENCE LISTING

```
<160> NUMBER OF SEQ ID NOS: 202

<210> SEQ ID NO 1
<211> LENGTH: 122
<212> TYPE: DNA
<213> ORGANISM: Homo sapiens

<400> SEQUENCE: 1
ggaattccta atacgactca ctatagggac aattactatt tacaattaca atgcatcacc      60
atcaccatca cgtttctgat gttccgaggg acctggaagt tgttgctgcg accccacca     120 gc                                                                   122
```

```
<210> SEQ ID NO 2
<211> LENGTH: 104
<212> TYPE: DNA
<213> ORGANISM: Homo sapiens

<400> SEQUENCE: 2
ggaattccta atacgactca ctatagggac aattactatt tacaattaca atgtttctg      60 atgttccgag ggacctggaa gttgttgctg cgaccccac cagc                      104

<210> SEQ ID NO 3
<211> LENGTH: 126
<212> TYPE: DNA
<213> ORGANISM: Homo sapiens
<220> FEATURE:
<221> NAME/KEY: misc_feature
<222> LOCATION: (1)...(126)
<223> OTHER INFORMATION: n = A,T,C or G
<220> FEATURE:
<221> NAME/KEY: misc_feature
<222> LOCATION: (1)...(126)
<223> OTHER INFORMATION: s = C or G
<220> FEATURE:
<221> NAME/KEY: misc_feature
<222> LOCATION: 74, 75, 77, 78, 80, 81, 83, 84, 86, 87, 89, 90, 92, 93
<223> OTHER INFORMATION: n = A,T,C or G

<400> SEQUENCE: 3
agcggatgcc ttgtcgtcgt cgtccttgta gtcgctcttc cctgtttctc cgtaagtgat      60
cctgtaatat ctsnnsnnsn nsnnsnnsnn snnccagctg atcagtaggc tggtgggggt     120
cgcagc                                                               126

<210> SEQ ID NO 4
<211> LENGTH: 62
<212> TYPE: DNA
<213> ORGANISM: Homo sapiens

<400> SEQUENCE: 4
agcggatgcc ttgtcgtcgt cgtccttgta gtcgctcttc cctgtttctc cgtaagtgat      60
cc                                                                    62

<210> SEQ ID NO 5
<211> LENGTH: 99
<212> TYPE: DNA
<213> ORGANISM: Homo sapiens

<400> SEQUENCE: 5
ggaattccta atacgactca ctatagggac aattactatt tacaattaca atgcatcacc      60
atcaccatca cctcttcaca ggaggaaata gccctgtcc                            99

<210> SEQ ID NO 6
<211> LENGTH: 132
<212> TYPE: DNA
<213> ORGANISM: Homo sapiens
<220> FEATURE:
<221> NAME/KEY: misc_feature
<222> LOCATION: (1)...(132)
<223> OTHER INFORMATION: n = A,T,C or G
<220> FEATURE:
<221> NAME/KEY: misc_feature
<222> LOCATION: (1)...(132)
<223> OTHER INFORMATION: s = C or G
<220> FEATURE:
<221> NAME/KEY: misc_feature
<222> LOCATION: 83, 84, 86, 87, 89, 90, 92, 93
<223> OTHER INFORMATION: n = A,T,C or G
```

```
<400> SEQUENCE: 6
agcggatgcc ttgtcgtcgt cgtccttgta gtcgctcttc gtataatcaa ctccaggttt    60
aaggccgctg atggtagctg tsnnsnnsnn snnaggcaca gtgaactcct ggacagggct   120
atttcctcct gt                                                       132

<210> SEQ ID NO 7
<211> LENGTH: 64
<212> TYPE: DNA
<213> ORGANISM: Homo sapiens

<400> SEQUENCE: 7
agcggatgcc ttgtcgtcgt cgtccttgta gtcgctcttc gtataatcaa ctccaggttt    60
aagg                                                                 64

<210> SEQ ID NO 8
<211> LENGTH: 101
<212> TYPE: DNA
<213> ORGANISM: Homo sapiens

<400> SEQUENCE: 8
ggaattccta atacgactca ctagggac aattactatt tacaattaca atgcatcacc      60
atcaccatca cctcttctat accatcactg tgtatgctgt c                       101

<210> SEQ ID NO 9
<211> LENGTH: 114
<212> TYPE: DNA
<213> ORGANISM: Homo sapiens
<220> FEATURE:
<221> NAME/KEY: misc_feature
<222> LOCATION: (1)...(114)
<223> OTHER INFORMATION: n = A,T,C or G
<220> FEATURE:
<221> NAME/KEY: misc_feature
<222> LOCATION: (1)...(114)
<223> OTHER INFORMATION: s = C or G
<220> FEATURE:
<221> NAME/KEY: misc_feature
<222> LOCATION: 59, 60, 62, 63, 65, 66, 68, 69, 71, 72, 74, 75, 77, 78,
      80, 81, 83, 84, 86, 87
<223> OTHER INFORMATION: n = A,T,C or G

<400> SEQUENCE: 9
agcggatgcc ttgtcgtcgt cgtccttgta gtctgttcgg taattaatgg aaattggsnn    60
snnsnnsnns nnsnnsnnsn nsnnsnnagt gacagcatac acagtgatgg tata          114

<210> SEQ ID NO 10
<211> LENGTH: 57
<212> TYPE: DNA
<213> ORGANISM: Homo sapiens

<400> SEQUENCE: 10
agcggatgcc ttgtcgtcgt cgtccttgta gtctgttcgg taattaatgg aaattgg        57

<210> SEQ ID NO 11
<211> LENGTH: 45
<212> TYPE: DNA
<213> ORGANISM: T7 phage and tobacco mosaic virus

<400> SEQUENCE: 11
gcgtaatacg actcactata gggacaatta ctatttacaa ttaca                     45
```

```
<210> SEQ ID NO 12
<211> LENGTH: 33
<212> TYPE: DNA
<213> ORGANISM: Artificial Sequence
<220> FEATURE:
<223> OTHER INFORMATION: Flag sequence

<400> SEQUENCE: 12
agcggatgcc ttgtcgtcgt cgtccttgta gtc                          33

<210> SEQ ID NO 13
<211> LENGTH: 19
<212> TYPE: DNA
<213> ORGANISM: Artificial Sequence
<220> FEATURE:
<223> OTHER INFORMATION: Splint oligonucleotide
<220> FEATURE:
<221> NAME/KEY: misc_feature
<222> LOCATION: (1)...(19)
<223> OTHER INFORMATION: n = A,T,C or G
<220> FEATURE:
<221> NAME/KEY: misc_feature
<222> LOCATION: 10
<223> OTHER INFORMATION: n = A,T,C or G

<400> SEQUENCE: 13
tttttttttn agcggatgc                                          19

<210> SEQ ID NO 14
<211> LENGTH: 20
<212> TYPE: DNA
<213> ORGANISM: Artificial Sequence
<220> FEATURE:
<223> OTHER INFORMATION: Puromycin linker oligonucleotide

<400> SEQUENCE: 14
aaaaaaaaaa aaaaaaaacc                                         20

<210> SEQ ID NO 15
<211> LENGTH: 30
<212> TYPE: DNA
<213> ORGANISM: Mus musculus

<400> SEQUENCE: 15
gcggcagggt ttgcttactg gggccaaggg                              30

<210> SEQ ID NO 16
<211> LENGTH: 27
<212> TYPE: DNA
<213> ORGANISM: Mus musculus

<400> SEQUENCE: 16
gggaggggtg gaggtaggtc acagtcc                                 27

<210> SEQ ID NO 17
<211> LENGTH: 30
<212> TYPE: DNA
<213> ORGANISM: Mus musculus

<400> SEQUENCE: 17
tttgctagct ttaccaggag agtgggaggc                              30

<210> SEQ ID NO 18
<211> LENGTH: 33
<212> TYPE: DNA
<213> ORGANISM: Mus musculus
```

```
<400> SEQUENCE: 18
aaaaagcttg ccaaaacgac accccatct gtc                              33

<210> SEQ ID NO 19
<211> LENGTH: 33
<212> TYPE: DNA
<213> ORGANISM: Mus musculus

<400> SEQUENCE: 19
catatggttt ctgatattcc gagagatctg gag                             33

<210> SEQ ID NO 20
<211> LENGTH: 43
<212> TYPE: DNA
<213> ORGANISM: Mus musculus

<400> SEQUENCE: 20
catatgcatc accatcacca tcacgtttct gatattccga gag                  43

<210> SEQ ID NO 21
<211> LENGTH: 30
<212> TYPE: DNA
<213> ORGANISM: Mus musculus

<400> SEQUENCE: 21
gaattcctat gttttataat tgatggaaac                                 30

<210> SEQ ID NO 22
<211> LENGTH: 19
<212> TYPE: DNA
<213> ORGANISM: Homo sapiens

<400> SEQUENCE: 22
tgtaaatagt aattgtccc                                             19

<210> SEQ ID NO 23
<211> LENGTH: 20
<212> TYPE: DNA
<213> ORGANISM: Homo sapiens

<400> SEQUENCE: 23
tttttttttt tttttttttt                                            20

<210> SEQ ID NO 24
<211> LENGTH: 15
<212> TYPE: DNA
<213> ORGANISM: Artificial Sequence
<220> FEATURE:
<223> OTHER INFORMATION: Oligonucleotide

<400> SEQUENCE: 24
cctgtaggtg tccat                                                 15

<210> SEQ ID NO 25
<211> LENGTH: 16
<212> TYPE: DNA
<213> ORGANISM: Homo sapiens

<400> SEQUENCE: 25
catcgtcctt gtagtc                                                16

<210> SEQ ID NO 26
<211> LENGTH: 13
```

```
<212> TYPE: DNA
<213> ORGANISM: Artificial Sequence
<220> FEATURE:
<223> OTHER INFORMATION: Oligonucleotide

<400> SEQUENCE: 26
cgtcgtaggg gta                                                     13

<210> SEQ ID NO 27
<211> LENGTH: 17
<212> TYPE: DNA
<213> ORGANISM: Artificial Sequence
<220> FEATURE:
<223> OTHER INFORMATION: Oligonucleotide

<400> SEQUENCE: 27
caggtcttct tcagaga                                                 17

<210> SEQ ID NO 28
<211> LENGTH: 24
<212> TYPE: DNA
<213> ORGANISM: Homo sapiens

<400> SEQUENCE: 28
catatggttt ctgatgttcc gagg                                         24

<210> SEQ ID NO 29
<211> LENGTH: 32
<212> TYPE: DNA
<213> ORGANISM: Homo sapiens

<400> SEQUENCE: 29
gaattcctat gttcggtaat taatggaaat tg                                32

<210> SEQ ID NO 30
<211> LENGTH: 19
<212> TYPE: DNA
<213> ORGANISM: Artificial Sequence
<220> FEATURE:
<223> OTHER INFORMATION: DNA splint Oligonucleotide
<220> FEATURE:
<221> NAME/KEY: misc_feature
<222> LOCATION: 10
<223> OTHER INFORMATION: n = A,T,C or G

<400> SEQUENCE: 30 ttttttttn agcggatgc                                                19

<210> SEQ ID NO 31
<211> LENGTH: 7
<212> TYPE: PRT
<213> ORGANISM: Homo sapien

<400> SEQUENCE: 31

Asn Arg Ser Gly Leu Gln Ser
 1               5

<210> SEQ ID NO 32
<211> LENGTH: 10
<212> TYPE: PRT
<213> ORGANISM: Homo sapien

<400> SEQUENCE: 32

Ala Gln Thr Gly His His Leu His Asp Lys
 1               5                  10
```

<210> SEQ ID NO 33
<211> LENGTH: 94
<212> TYPE: PRT
<213> ORGANISM: Homo sapien

<400> SEQUENCE: 33

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 34
<211> LENGTH: 95
<212> TYPE: PRT
<213> ORGANISM: Homo sapiens

<400> SEQUENCE: 34

Val Ser Glu Ile Pro Arg Asp Leu Glu Val Val Ala Ala Thr Pro Thr
1               5                   10                  15

Ser Leu Leu Phe Ser Trp Asp Ala Pro Ala Val Thr Val Arg Tyr Tyr
            20                  25                  30

Arg Ile Thr Tyr Gly Glu Thr Gly Gly Asn Ser Leu Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Asn Thr Ile Thr Gly Tyr Ala Val Thr Thr Thr Tyr
65                  70                  75                  80

Arg Thr Arg Ile Asp Lys Gln Pro Ile Ser Ile Asn Tyr Arg Thr
                85                  90                  95

<210> SEQ ID NO 35
<211> LENGTH: 90
<212> TYPE: PRT
<213> ORGANISM: Homo sapien

<400> SEQUENCE: 35

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Lys Gly Gly Asn Ser Pro Val Gln Glu Phe
        35                  40                  45

Thr Val Pro Glu Leu Asn Pro Thr Ala Thr Ile Ser Arg Leu Lys Pro
    50                  55                  60

Gly Val Asp Tyr Thr Ile Thr Val Tyr Ala Val Thr Gln Asn Gly Thr
65                  70                  75                  80

Pro Arg Arg His Leu Arg Pro Asn Phe His
                85                  90

-continued

```
<210> SEQ ID NO 36
<211> LENGTH: 95
<212> TYPE: PRT
<213> ORGANISM: Homo sapien

<400> SEQUENCE: 36

Val Ser Asp Val Pro Arg Asp Leu Glu Val Val Ala Ala Thr Pro Thr
1               5                   10                  15

Gly Leu Leu Ile Ser Trp Asn Lys Ser Arg Met Thr Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Val Thr Asp Ser Thr Ala Thr Ile Ser Gly Leu Lys Pro
50                  55                  60

Gly Val Asp Tyr Asn Thr Ile Ile Val His Ala Val Thr Leu Thr Asn
65                  70                  75                  80

Gln Asn Ser Asp His Thr Tyr Pro Ile Ser Ile Asn Tyr Arg Thr
                85                  90                  95

<210> SEQ ID NO 37
<211> LENGTH: 91
<212> TYPE: PRT
<213> ORGANISM: Homo sapien

<400> SEQUENCE: 37

Val Ser Asp Val Pro Arg Asp Leu Asp Val Val Ala Ala Thr Pro Thr
1               5                   10                  15

Ser Leu Leu Ile Ser Trp Asp Ser Ser His Arg Tyr Tyr Arg Ile Thr
            20                  25                  30

Tyr Gly Glu Thr Gly Gly Asn Ser Pro Val Gln Glu Phe Thr Ala Pro
        35                  40                  45

Asn Asn Pro Pro Thr Ala Thr Ile Ser Gly Leu Lys Pro Gly Val Asp
50                  55                  60

Tyr Thr Ile Thr Val Tyr Ala Val Thr Pro Asp Gly Ser Arg His Met
65                  70                  75                  80

Leu Thr Lys Pro Ile Ser Ile Asn Tyr Arg Thr
                85                  90

<210> SEQ ID NO 38
<211> LENGTH: 88
<212> TYPE: PRT
<213> ORGANISM: Homo sapiens

<400> SEQUENCE: 38

Val Ser Asp Val Pro Arg Asp Leu Glu Val Val Ala Ala Thr Pro Thr
1               5                   10                  15

Ser Leu Leu Ile Ser Trp His Asn Asn His Ile Asp Met Arg Tyr Tyr
            20                  25                  30

Arg Ser Ala Asn Gly Glu Thr Gly Gly Asn Ser Pro Val Gln Val Phe
        35                  40                  45

Thr Val Pro Gln Arg Arg Gln Thr Ala Thr Ile Ser Gly Leu Lys Pro
50                  55                  60

Gly Val Asp Tyr Thr Ile Thr Val Tyr Ala Val Thr Pro Lys Asn Gln
65                  70                  75                  80

Gly Arg Arg Arg Gln Gly Ile Arg
                85

<210> SEQ ID NO 39
```

-continued

<211> LENGTH: 94
<212> TYPE: PRT
<213> ORGANISM: Homo sapiens

<400> SEQUENCE: 39

Val Ser Asp Val Pro Arg Asp Leu Glu Val Val Ala Ala Thr Ser Thr
1               5                   10                  15

Ser Leu Leu Ile Ser Trp Arg Thr Pro Ala Ser Pro His Gly Tyr Tyr
            20                  25                  30

Arg Ile Thr Tyr Gly Glu Thr Gly Gly Asn Ser Pro Val Glu Glu Phe
        35                  40                  45

Thr Val Pro Leu Leu Trp Pro Thr Ala Thr Ile Ser Gly Leu Lys Pro
    50                  55                  60

Gly Val Asp Tyr Thr Ile Thr Val Tyr Ala Val Thr Pro Thr His Met
65                  70                  75                  80

Leu Lys Pro Gln Ser Met Pro Ile Ser Ile Asn Tyr Arg Thr
                85                  90

<210> SEQ ID NO 40
<211> LENGTH: 94
<212> TYPE: PRT
<213> ORGANISM: Homo sapien

<400> SEQUENCE: 40

Val Ser Asp Val Pro Arg Asp Leu Glu Val Val Ala Ala Thr Pro Thr
1               5                   10                  15

Ser Leu Leu Ile Ser Trp Arg Thr Pro Ala Ser Pro His Gly Tyr Tyr
            20                  25                  30

Arg Ile Thr Tyr Gly Glu Thr Gly Gly Asn Ser Pro Val Glu Glu Phe
        35                  40                  45

Thr Val Pro Leu Leu Trp Pro Thr Ala Thr Ile Ser Gly Leu Lys Pro
    50                  55                  60

Gly Val Asp Tyr Thr Ile Thr Val Tyr Ala Val Thr Pro Thr His Met
65                  70                  75                  80

Leu Lys Pro Gln Ser Met Pro Ile Ser Ile Asn Tyr Arg Thr
                85                  90

<210> SEQ ID NO 41
<211> LENGTH: 94
<212> TYPE: PRT
<213> ORGANISM: Homo sapien

<400> SEQUENCE: 41

Val Ser Asp Val Pro Arg Asp Leu Glu Val Val Ala Ala Ala Ser Thr
1               5                   10                  15

Ser Leu Leu Ile Ser Trp Arg Pro Asn Pro Arg Leu Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Leu Phe Ser Thr Ala Thr Ile Ser Gly Leu Asn Pro
    50                  55                  60

Gly Val Asp Tyr Thr Ile Thr Val Tyr Ala Val Thr Pro Lys Glu Thr
65                  70                  75                  80

Ser Asn Ile Phe Ile Ala Pro Ile Ser Ile Asn Tyr Arg Thr
                85                  90

<210> SEQ ID NO 42
<211> LENGTH: 94

```
<212> TYPE: PRT
<213> ORGANISM: Homo sapien

<400> SEQUENCE: 42

Val Ser Asp Val Pro Arg Asp Leu Glu Val Val Ala Ala Thr Ser Thr
  1               5                  10                  15

Cys Leu Leu Ile Ser Trp Arg Pro Asn Pro Arg Leu Ser Arg Tyr Tyr
             20                  25                  30

Arg Ile Thr Tyr Gly Glu Thr Gly Asn Ser Pro Val Gln Glu Phe
             35                  40                  45

Thr Val Pro Gly Leu Phe Ser Thr Ala Thr Ile Ser Gly Leu Lys Pro
         50                  55                  60

Gly Val Asp Tyr Thr Ile Thr Val Tyr Ala Val Thr Pro Lys Glu Thr
 65                  70                  75                  80

Ser Asn Ile Phe Ile Ala Pro Ile Ser Ile Asn Tyr Arg Thr
                 85                  90

<210> SEQ ID NO 43
<211> LENGTH: 94
<212> TYPE: PRT
<213> ORGANISM: Homo sapien

<400> SEQUENCE: 43

Val Ser Asp Val Pro Arg Asp Pro Glu Val Val Ala Ala Thr Pro Thr
  1               5                  10                  15

Ser Leu Leu Ile Ser Trp Asp Pro Asn Ile Arg Leu Arg Arg Tyr Tyr
             20                  25                  30

Arg Ile Thr Tyr Gly Glu Thr Gly Gly Asn Ser Pro Val Gln Glu Phe
             35                  40                  45

Thr Val Pro Gly Phe Phe Ser Thr Ala Thr Ile Ser Gly Leu Lys Pro
         50                  55                  60

Gly Val Asp Tyr Thr Ile Thr Val Tyr Ala Val Thr Ala Ser Arg Asn
 65                  70                  75                  80

Glu Asp Thr Arg Phe Gly Pro Ile Ser Ile Asn Tyr Arg Thr
                 85                  90

<210> SEQ ID NO 44
<211> LENGTH: 94
<212> TYPE: PRT
<213> ORGANISM: Homo sapiens

<400> SEQUENCE: 44

Val Ser Asp Val Pro Arg Asp Leu Glu Val Val Ala Ala Thr Pro Thr
  1               5                  10                  15

Ser Leu Leu Ile Ser Trp Phe Arg Ser Leu Gln Arg Asp Arg Asp Tyr
             20                  25                  30

Arg Ile Thr Tyr Gly Glu Thr Gly Gly Asn Ser Pro Val Gln Glu Phe
             35                  40                  45

Thr Val Pro Phe Arg Met Lys Thr Ala Thr Ile Ser Gly Leu Lys Pro
         50                  55                  60

Gly Val Asp Tyr Thr Ile Thr Val Tyr Ala Ile Thr Pro Pro Asp Lys
 65                  70                  75                  80

Met Glu Pro Pro Lys Gly Pro Ile Ser Ile Asn Tyr Arg Thr
                 85                  90

<210> SEQ ID NO 45
<211> LENGTH: 94
<212> TYPE: PRT
```

<213> ORGANISM: Homo sapiens

<400> SEQUENCE: 45

Val Ser Asp Val Pro Arg Asp Leu Glu Val Val Ala Ala Thr Pro Thr
1               5                   10                  15

Ser Leu Leu Ile Ser Trp Tyr Arg His Thr Tyr Arg Asp Arg Tyr Tyr
            20                  25                  30

Arg Ile Thr Tyr Gly Glu Thr Gly Gly Asn Ser Pro Val Gln Glu Ser
        35                  40                  45

Thr Val Pro Pro Trp Ala Thr Thr Ala Thr Ile Ser Gly Leu Lys Pro
    50                  55                  60

Gly Val Asp Tyr Thr Ile Ala Val Tyr Ala Val Thr Asp Thr Gly Tyr
65                  70                  75                  80

Asp Val His Thr Lys Arg Pro Ile Ser Ile Asn Tyr Arg Thr
                85                  90

<210> SEQ ID NO 46
<211> LENGTH: 94
<212> TYPE: PRT
<213> ORGANISM: Homo sapiens

<400> SEQUENCE: 46

Val Ser Asp Val Pro Arg Asp Leu Glu Val Val Ala Ala Ala Pro Thr
1               5                   10                  15

Ser Leu Leu Ile Ser Trp Tyr Arg His Thr Tyr Arg Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Thr Thr Ala Ala Ile Ser Gly Leu Lys Pro
    50                  55                  60

Gly Val Asp Tyr Ala Ile Ala Val Tyr Ala Val Thr Asp Thr Gly Tyr
65                  70                  75                  80

Asp Val His Thr Lys Arg Pro Ile Ser Ile Asn Tyr Arg Thr
                85                  90

<210> SEQ ID NO 47
<211> LENGTH: 94
<212> TYPE: PRT
<213> ORGANISM: Homo sapiens

<400> SEQUENCE: 47

Val Ser Asp Val Pro Arg Asp Leu Glu Val Val Ala Ala Thr Pro Thr
1               5                   10                  15

Ser Gln Leu Ile Ser Trp Pro Phe Gly Trp Tyr Pro Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Arg Thr Ala Thr Ile Ser Gly Leu Lys Pro
    50                  55                  60

Gly Val Asp Tyr Thr Ile Thr Val Tyr Ala Val Thr Asp Tyr Ser Asp
65                  70                  75                  80

Phe Ser Gln Val His Thr Pro Asn Ser Ile Asn Tyr Arg Thr
                85                  90

<210> SEQ ID NO 48
<211> LENGTH: 93
<212> TYPE: PRT
<213> ORGANISM: Homo sapiens

```
<400> SEQUENCE: 48

Val Ser Asp Val Pro Arg Asp Leu Glu Val Val Ala Ala Thr Pro Thr
 1               5                  10                  15

Ser Arg Leu Ile Ser Trp Arg Pro Gly Arg Thr Tyr Ser Arg Tyr Arg
                20                  25                  30

Ile Thr Tyr Gly Glu Thr Gly Gly Asn Ser Pro Val Gln Glu Phe Thr
            35                  40                  45

Val Pro Pro Trp Ala Asn Thr Ala Thr Ile Ser Gly Leu Lys Pro Gly
        50                  55                  60

Val Asp Tyr Thr Ile Thr Val Tyr Ala Val Thr Pro Leu Pro Ile Pro
65                  70                  75                  80

Thr Leu Val His Gly Pro Ile Ser Ile Asn Tyr Arg Thr
                85                  90

<210> SEQ ID NO 49
<211> LENGTH: 94
<212> TYPE: PRT
<213> ORGANISM: Homo sapiens

<400> SEQUENCE: 49

Val Ser Asp Val Pro Arg Asp Leu Glu Val Val Ala Ala Thr Pro Thr
 1               5                  10                  15

Ser Arg Leu Ile Ser Trp Ala Ser Pro Met Trp Cys Arg Tyr Tyr
                20                  25                  30

Arg Ile Thr Tyr Gly Glu Thr Gly Gly Asn Gly Pro Val Gln Glu Phe
            35                  40                  45

Thr Val Pro Pro Trp Ala Thr Thr Ala Thr Ile Ser Gly Leu Lys Pro
        50                  55                  60

Gly Val Asp Tyr Thr Ile Thr Val Tyr Ala Val Thr Glu Tyr Leu Pro
65                  70                  75                  80

Glu Trp Asn Met Thr Gln Pro Ile Ser Ile Asn Tyr Arg Thr
                85                  90

<210> SEQ ID NO 50
<211> LENGTH: 94
<212> TYPE: PRT
<213> ORGANISM: Homo sapiens

<400> SEQUENCE: 50

Val Ser Asp Val Pro Arg Asp Leu Glu Val Val Ala Ala Thr Pro Thr
 1               5                  10                  15

Ser Arg Leu Ile Ser Trp Ala Ser Pro Met Trp Cys Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Thr Thr Ala Thr Ile Ser Gly Leu Lys Pro
        50                  55                  60

Gly Val Asp Tyr Thr Ile Thr Met Tyr Ala Val Thr Glu Tyr Leu Pro
65                  70                  75                  80

Glu Trp Asn Met Thr Gln Pro Ile Ser Ile Asn Tyr Arg Thr
                85                  90

<210> SEQ ID NO 51
<211> LENGTH: 93
<212> TYPE: PRT
<213> ORGANISM: Homo sapiens
```

```
<400> SEQUENCE: 51

Asn Thr Thr His Tyr Arg Lys Asn Asn Tyr Ala Thr Pro Thr Ser
1               5                   10                  15

Arg Leu Ile Ser Trp Asn Arg Ser Gly Leu Gln Ser Arg Tyr Tyr Arg
            20                  25                  30

Ile Thr Tyr Gly Glu Thr Gly Gly Asn Ser Pro Val Gln Glu Phe Thr
                35                  40                  45

Val Pro Pro Trp Ala Ser Ile Ala Thr Ile Ser Gly Leu Lys Pro Gly
50                  55                  60

Val Asp Tyr Thr Ile Thr Val Tyr Ala Val Thr Asp Lys Ser Asp Thr
65                  70                  75                  80

Tyr Lys Tyr Asp Asp Pro Ile Ser Ile Asn Tyr Arg Thr
                85                  90

<210> SEQ ID NO 52
<211> LENGTH: 93
<212> TYPE: PRT
<213> ORGANISM: Homo sapiens

<400> SEQUENCE: 52

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
                35                  40                  45

Thr Val Pro Pro Trp Ala Ser Ile Ala Thr Ile Ser Gly Leu Lys Pro
50                  55                  60

Gly Val Asp Tyr Thr Ile Thr Val Tyr Ala Val Thr Ser Ala Thr Arg
65                  70                  75                  80

Thr Val Lys Arg Asp Pro Ile Ser Ile Asn Tyr Arg Thr
                85                  90

<210> SEQ ID NO 53
<211> LENGTH: 94
<212> TYPE: PRT
<213> ORGANISM: Homo sapiens

<400> SEQUENCE: 53

Val Ser Asp Ala Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
                35                  40                  45

Thr Val Pro Pro Trp Ala Ser Ile Ala Thr Ile Ser Gly Leu Lys Pro
50                  55                  60

Gly Val Asp Tyr Thr Ile Thr Met Tyr Ala Val Thr Ser Asn Val Gly
65                  70                  75                  80

Arg Leu Asp Thr Arg Tyr Pro Ile Ser Ile Asn Tyr Arg Thr
                85                  90

<210> SEQ ID NO 54
<211> LENGTH: 94
<212> TYPE: PRT
<213> ORGANISM: Homo sapiens

<400> SEQUENCE: 54
```

Val Ser Asp Val Pro Arg Asp Leu Asp Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
        35                  40                  45

Thr Glu Pro Pro Trp Ala Ser Ile Ala Thr Ile Ser Gly Leu Lys Pro
    50                  55                  60

Gly Val Asp Tyr Thr Ile Thr Val Tyr Ala Val Thr Ser Asn Val Gly
65                  70                  75                  80

Arg Leu Asp Thr Arg Tyr Pro Ile Ser Ile Asn Tyr Arg Thr
                85                  90

<210> SEQ ID NO 55
<211> LENGTH: 94
<212> TYPE: PRT
<213> ORGANISM: Homo sapiens

<400> SEQUENCE: 55

Val Ser Asp Val Pro Arg Asp Leu Glu Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Lys Glu Pro Gln
65                  70                  75                  80

Arg His Ala Leu Val Thr Pro Ile Ser Ile Asn Tyr Arg Thr
                85                  90

<210> SEQ ID NO 56
<211> LENGTH: 94
<212> TYPE: PRT
<213> ORGANISM: Homo sapiens

<400> SEQUENCE: 56

Val Ser Asp Val Pro Arg Asp Leu Glu Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Glu Thr Pro Ser
65                  70                  75                  80

Thr Lys Pro His Asn Val Pro Ile Ser Ile Asn Tyr Arg Thr
                85                  90

<210> SEQ ID NO 57
<211> LENGTH: 74
<212> TYPE: PRT
<213> ORGANISM: Homo sapiens

<400> SEQUENCE: 57

-continued

Val Ser Asp Val Pro Arg Asp Leu Glu Val Ala Ala Thr Pro Thr
1               5                   10                  15

Ser Arg Leu Ile Ser Trp Asn His Pro Gly Pro Phe Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Arg Thr Ala Ile Ile Ser Gly Leu Lys Pro
    50                  55                  60

Gly Val Asp Tyr Thr Ile Thr Val Tyr Ala
65                  70

<210> SEQ ID NO 58
<211> LENGTH: 93
<212> TYPE: PRT
<213> ORGANISM: Homo sapiens

<400> SEQUENCE: 58

Val Ser Asp Val Pro Arg Asp Leu Glu Val Val Ala Ala Thr Thr Ser
1               5                   10                  15

Leu Leu Ile Ser Trp Asp Tyr Asn Arg Thr Gly Asp Arg Tyr Tyr Arg
                20                  25                  30

Ile Thr Tyr Gly Glu Thr Gly Gly Asn Ser Pro Val Gln Glu Phe Thr
            35                  40                  45

Val Pro Pro Trp Ala Ser Ile Ala Thr Ile Gly Gly Leu Lys Pro Gly
    50                  55                  60

Val Asp Tyr Thr Ile Thr Val Tyr Ala Val Thr Ala Gln Thr Gly His
65                  70                  75                  80

His Leu His Asp Lys Pro Ile Ser Ile Asn Tyr Arg Ser
                85                  90

<210> SEQ ID NO 59
<211> LENGTH: 94
<212> TYPE: PRT
<213> ORGANISM: Homo sapiens

<400> SEQUENCE: 59

Val Ser Asp Val Pro Arg Asp Leu Glu Val Val Ala Ala Thr Ser Thr
1               5                   10                  15

Ser Leu Leu Ile Ser Trp His Tyr Leu Arg Arg Gln Pro Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Ser Ile Ala Thr Ile Gly Gly Leu Lys Pro
    50                  55                  60

Gly Val Asp Tyr Thr Ile Thr Val Tyr Ala Val Thr Ala Gln Thr Gly
65                  70                  75                  80

His His Leu His Asp Glu Pro Ile Ser Ile Asn Tyr Arg Thr
                85                  90

<210> SEQ ID NO 60
<211> LENGTH: 94
<212> TYPE: PRT
<213> ORGANISM: Homo sapiens

<400> SEQUENCE: 60

Val Ser Asp Val Pro Arg Asp Leu Gln Ile Val Ala Ala Thr Pro Thr
1               5                   10                  15

Ser Leu Leu Ile Ser Trp Asp Ile Ser Arg Tyr Lys His Arg Tyr Tyr

```
              20                  25                  30
Arg Ile Thr Tyr Gly Glu Thr Gly Asp Ser Pro Val Gln Glu Phe
         35                  40                  45

Thr Ala Pro Pro Trp Ala Ser Ile Ala Thr Ile Gly Gly Leu Lys Pro
 50                  55                  60

Gly Val Asp Tyr Thr Ile Thr Val Tyr Ala Val Thr Ala Gln Thr Gly
 65                  70                  75                  80

His His Leu His Asp Lys Pro Ile Ser Ile Asn Tyr Arg Thr
                 85                  90
```

<210> SEQ ID NO 61
<211> LENGTH: 93
<212> TYPE: PRT
<213> ORGANISM: Homo sapiens

<400> SEQUENCE: 61

```
Val Ser Asp Val Pro Arg Asp Leu Glu Val Val Ala Ala Thr Pro Thr
 1               5                  10                  15

Ser Arg Leu Ile Ser Trp Arg Pro Thr Ser Asn Pro Pro Arg Tyr Tyr
              20                  25                  30

Arg Ile Thr Tyr Gly Glu Thr Gly Asn Ser Pro Val Gln Glu Phe
         35                  40                  45

Thr Val Pro Pro Trp Ala Ser Ile Thr Ile Gly Gly Leu Lys Pro Gly
 50                  55                  60

Val Asp Tyr Thr Ile Thr Val Tyr Ala Val Thr Ala Gln Thr Gly His
 65                  70                  75                  80

His Leu His Asp Lys Pro Ile Ser Ile Asn Tyr Arg Thr
              85                  90
```

<210> SEQ ID NO 62
<211> LENGTH: 94
<212> TYPE: PRT
<213> ORGANISM: Homo sapiens

<400> SEQUENCE: 62

```
Val Ser Asp Val Pro Arg Asp Leu Glu Val Val Ala Ala Thr Pro Thr
 1               5                  10                  15

Ser Arg Leu Ile Cys Trp Arg Pro Thr Ser Asn Pro Pro Arg Tyr Tyr
              20                  25                  30

Arg Ile Thr Tyr Gly Glu Thr Gly Asn Ser Pro Val Gln Glu Phe
         35                  40                  45

Thr Val Pro Pro Trp Ala Ser Ile Ala Thr Ile Gly Gly Leu Lys Pro
 50                  55                  60

Gly Val Asp Tyr Thr Ile Thr Val Tyr Ala Val Thr Ala Gln Thr Gly
 65                  70                  75                  80

His His Leu His Asp Lys Pro Ile Ser Ile Asn Tyr Arg Thr
                 85                  90
```

<210> SEQ ID NO 63
<211> LENGTH: 94
<212> TYPE: PRT
<213> ORGANISM: Homo sapiens

<400> SEQUENCE: 63

```
Val Ser Asp Val Pro Arg Asp Leu Glu Val Val Ala Ala Thr Pro Thr
 1               5                  10                  15

Ser Arg Leu Ile Ser Trp Arg Pro Thr Ser Asn Pro Pro Arg Tyr Tyr
              20                  25                  30
```

-continued

Arg Ile Ser Tyr Gly Glu Thr Gly Asn Ser Pro Val Gln Glu Phe
        35                  40                  45

Thr Val Pro Pro Trp Ala Ser Ile Ala Thr Ile Gly Gly Leu Lys Pro
    50                  55                  60

Gly Val Asp Tyr Thr Ile Thr Val Tyr Ala Val Thr Ala Gln Thr Gly
65                  70                  75                  80

His His Leu His Asp Lys Pro Ile Ser Ile Asn Tyr Arg Thr
            85                  90

<210> SEQ ID NO 64
<211> LENGTH: 94
<212> TYPE: PRT
<213> ORGANISM: Homo sapiens

<400> SEQUENCE: 64

Val Ser Asp Val Pro Arg Asp Leu Glu Val Val Ala Ala Thr Pro Thr
1               5                   10                  15

Ser Gln Leu Ile Ser Trp Lys Thr Thr Asn Pro Thr Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Thr Ile Ala Thr Ile Ser Gly Leu Lys Pro
    50                  55                  60

Gly Val Asp Tyr Thr Ile Thr Val Tyr Ala Val Thr Asn Leu Thr Thr
65                  70                  75                  80

Arg Arg Arg His Arg Ala Pro Ile Ser Ile Asn Tyr Arg Thr
            85                  90

<210> SEQ ID NO 65
<211> LENGTH: 94
<212> TYPE: PRT
<213> ORGANISM: Homo sapiens

<400> SEQUENCE: 65

Val Ser Asp Val Pro Arg Asp Leu Glu Val Val Ala Ala Thr Pro Thr
1               5                   10                  15

Ser Arg Leu Ile Ser Trp Thr Thr Arg His Ser Pro Val Arg Tyr Tyr
            20                  25                  30

Arg Ile Thr Tyr Gly Glu Thr Gly Gly Asn Ser Pro Val Gln Glu Phe
        35                  40                  45

Ile Val Pro Pro Trp Ala Thr Ala Thr Ile Ser Gly Leu Lys Pro
    50                  55                  60

Gly Val Asp Tyr Thr Ile Thr Val Tyr Ala Val Thr Met Pro Thr Asn
65                  70                  75                  80

Trp Arg Phe Pro His Arg Pro Ile Ser Ile Asp Tyr Arg Thr
            85                  90

<210> SEQ ID NO 66
<211> LENGTH: 90
<212> TYPE: PRT
<213> ORGANISM: Homo sapiens

<400> SEQUENCE: 66

Val Ser Asp Val Pro Arg Asp Leu Glu Ala Val Ala Ala Thr Pro Thr
1               5                   10                  15

Ser Leu Leu Ile Arg Glu Arg Glu Arg Arg Tyr Tyr Arg Ile Thr Tyr
            20                  25                  30

```
Gly Glu Thr Gly Gly Asn Ser Pro Val Gln Glu Phe Thr Val Pro Gly
            35                  40                  45

Ser Lys Ser Thr Ala Thr Ile Ser Gly Leu Glu Pro Gly Val Asp Tyr
 50                  55                  60

Thr Ile Thr Val Tyr Ala Val Thr Pro His His Gly His Phe Asp Leu
 65                  70                  75                  80

Glu Leu Pro Ile Ser Ile Asn Tyr Arg Thr
                 85                  90

<210> SEQ ID NO 67
<211> LENGTH: 94
<212> TYPE: PRT
<213> ORGANISM: Homo sapiens

<400> SEQUENCE: 67

Val Ser Asp Val Pro Arg Asp Leu Glu Gly Val Ala Ala Thr Pro Thr
 1               5                  10                  15

Ser Leu Leu Ile Ser Arg Lys Asp Arg Val Ser Arg Arg Tyr Tyr
             20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Ile Ile Ser Gly Leu Lys Pro
 50                  55                  60

Gly Val Asp Tyr Thr Ile Thr Ala Tyr Val Val Thr Pro His His Gly
 65                  70                  75                  80

His Phe Asp Leu Glu Leu Pro Ile Ser Ile Asn Tyr Arg Thr
                 85                  90

<210> SEQ ID NO 68
<211> LENGTH: 95
<212> TYPE: PRT
<213> ORGANISM: Homo spiens

<400> SEQUENCE: 68

Val Ser Asp Val Pro Arg Asp Leu Glu Val Val Ala Ala Thr Pro Thr
 1               5                  10                  15

Ser Leu Leu Ile Ser Trp His Met Ala Thr Pro Asn Thr Arg Tyr Tyr
             20                  25                  30

Arg Thr Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
 50                  55                  60

Gly Val Asp Tyr Asn Thr Asn Thr Val Tyr Ala Val Thr Ser Val Asn
 65                  70                  75                  80

Ala Phe Pro Tyr Glu Gly Met Pro Ile Ser Ile Asn Tyr Arg Thr
                 85                  90                  95

<210> SEQ ID NO 69
<211> LENGTH: 94
<212> TYPE: PRT
<213> ORGANISM: Homo sapiens

<400> SEQUENCE: 69

Val Ser Asp Val Pro Arg Asp Leu Glu Val Val Ala Ala Thr Ala Thr
 1               5                  10                  15

Ser Leu Leu Ser Ser Trp Tyr Leu Cys Thr Gly Asn Asn Arg Asp Tyr
             20                  25                  30

Arg Ile Thr Tyr Gly Glu Thr Gly Gly Asn Ser Pro Val Gln Ala Phe
```

```
                    35                  40                  45
Thr Val Pro Gly Ser Lys Ser Thr Ala Thr Ile Ser Gly Leu Lys Pro
        50                  55                  60

Gly Val Asp Tyr Ile Pro Ser Arg Cys Met Leu Ser Leu Ala Ser Leu
65                  70                  75                  80

Met Ser Thr Arg Asn Lys Pro Ile Ser Ile Asn Tyr Arg Thr
                85                  90

<210> SEQ ID NO 70
<211> LENGTH: 94
<212> TYPE: PRT
<213> ORGANISM: Homo sapiens

<400> SEQUENCE: 70

Val Ser Asp Val Pro Arg Asp Leu Glu Val Ala Ala Thr Pro Thr
1               5                   10                  15

Ser Leu Leu Ile Ser Trp Arg Thr Pro Ala Ser Pro His Gly Tyr Tyr
                20                  25                  30

Arg Ile Thr Tyr Gly Glu Thr Gly Gly Asn Ser Pro Val Glu Glu Phe
            35                  40                  45

Thr Val Pro Leu Leu Trp Pro Thr Ala Thr Ile Ser Gly Leu Lys Pro
        50                  55                  60

Gly Val Asp Tyr Ala Ile Thr Val Tyr Ala Val Thr Pro Thr His Met
65                  70                  75                  80

Leu Lys Pro Leu Ser Met Pro Ile Ser Ile Asn Tyr Arg Thr
                85                  90

<210> SEQ ID NO 71
<211> LENGTH: 93
<212> TYPE: PRT
<213> ORGANISM: Homo sapiens

<400> SEQUENCE: 71

Ile Ser Asp Val Pro Arg Asp Met Glu Val Val Ala Ala Thr Pro Thr
1               5                   10                  15

Ser Leu Leu Ile Ser Trp Asn Met Ala His Pro His Asp Arg Asn Tyr
                20                  25                  30

Arg Ile Thr Tyr Gly Glu Thr Gly Gly Asn Ser Pro Val Gln Glu Ser
            35                  40                  45

Thr Val Pro Arg Tyr Leu Ser Thr Ala Thr Ile Ser Gly Pro Lys Arg
        50                  55                  60

Val Asp Tyr Thr Ile Ile Val Tyr Ala Val Asn Gln Pro Thr Val Ser
65                  70                  75                  80

Ala His Asn His Ala Pro Ile Ser Ile Asn Tyr Arg Thr
                85                  90

<210> SEQ ID NO 72
<211> LENGTH: 93
<212> TYPE: PRT
<213> ORGANISM: Homo sapiens

<400> SEQUENCE: 72

Val Ser Asp Val Pro Arg Asp Leu Lys Val Val Ala Ala Thr Pro Thr
1               5                   10                  15

Ser Leu Leu Ile Ser Trp Phe Pro Asp Asn Ala Thr Pro Arg Tyr Tyr
                20                  25                  30

Arg Ile Thr Tyr Gly Glu Thr Gly Gly Asn Ser Pro Val Gln Glu Phe
            35                  40                  45
```

```
Thr Val Pro Leu Phe Thr Thr Ala Thr Ile Ser Gly Leu Lys Pro Gly
            50                  55                  60

Val Asp Tyr Thr Ile Thr Val Tyr Ala Val Thr Ser His Arg Asp Tyr
 65                  70                  75                  80

His Ser Thr Gly Arg Pro Ile Ser Ile Asn Tyr Arg Thr
                 85                  90

<210> SEQ ID NO 73
<211> LENGTH: 95
<212> TYPE: PRT
<213> ORGANISM: Homo sapiens

<400> SEQUENCE: 73

Val Ser Asp Val Pro Arg Asp Leu Glu Val Val Ala Ala Thr Pro Thr
  1               5                  10                  15

Ser Leu Leu Ile Ser Trp Met Leu Leu Arg Asp Asp Arg Arg Tyr Tyr
                 20                  25                  30

Arg Ile Thr Tyr Gly Glu Thr Gly Gly Asn Ser Pro Val Gln Glu Phe
             35                  40                  45

Thr Val Pro Thr Phe His Pro Thr Ala Thr Ile Ser Gly Arg Lys Pro
        50                  55                  60

Gly Val Asp Tyr Asn Thr Ile Thr Val Tyr Ala Val Thr Gln Ser Thr
 65                  70                  75                  80

Asn Gly Asn Arg Asn Asp Phe Pro Ile Ser Ile Asn Tyr Arg Thr
                 85                  90                  95

<210> SEQ ID NO 74
<211> LENGTH: 94
<212> TYPE: PRT
<213> ORGANISM: Homo sapiens

<400> SEQUENCE: 74

Val Ser Asp Val Pro Arg Asp Leu Glu Val Val Ala Ala Thr Pro Thr
  1               5                  10                  15

Ser Leu Leu Ile Ser Trp Ser Pro Pro Asn Asp Ala His Arg Tyr Tyr
                 20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
        50                  55                  60

Gly Val Asp Tyr Thr Asn Thr Val Tyr Ala Val Thr Asp Gln Gln Ser
 65                  70                  75                  80

Tyr Thr Tyr Tyr Ser Asn Pro Ile Ser Ile Asn Tyr Arg Thr
                 85                  90

<210> SEQ ID NO 75
<211> LENGTH: 94
<212> TYPE: PRT
<213> ORGANISM: Homo sapiens

<400> SEQUENCE: 75

Val Ser Asp Val Pro Arg Asp Leu Glu Val Val Ala Ala Thr Pro Thr
  1               5                  10                  15

Ser Leu Val Ile Ser Trp Ser Pro Pro Asn Asp Ala His Arg Tyr Tyr
                 20                  25                  30

Arg Ile Thr Tyr Gly Glu Thr Gly Gly Asn Ser Pro Val Gln Glu Phe
             35                  40                  45
```

```
Thr Val Pro Gly Ser Lys Ser Thr Ala Thr Ile Ser Gly Leu Lys Pro
            50                  55                  60

Gly Val Asp Tyr Thr Asn Thr Val Tyr Ala Val Thr Asp Gln Gln Ser
65                  70                  75                  80

Tyr Thr Tyr Tyr Ser Asn Pro Ile Ser Ile Asn Tyr Arg Thr
                85                  90
```

<210> SEQ ID NO 76
<211> LENGTH: 92
<212> TYPE: PRT
<213> ORGANISM: Homo sapiens

<400> SEQUENCE: 76

```
Val Ser Asp Val Pro Arg Asp Leu Glu Val Val Ala Ala Thr Pro Thr
1               5                   10                  15

Ser Leu Leu Ile Ser Trp Ser Pro Pro Asn Asp Ala His Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Thr Ala Thr Ile Ser Gly Leu Lys Pro
            50                  55                  60

Gly Val Asp Tyr Thr Ile Thr Val Tyr Thr Met Pro Thr Asn Trp Arg
65                  70                  75                  80

Phe Pro His Arg Pro Ile Ser Ile Asn Tyr Arg Thr
                85                  90
```

<210> SEQ ID NO 77
<211> LENGTH: 94
<212> TYPE: PRT
<213> ORGANISM: Homo sapiens

<400> SEQUENCE: 77

```
Val Ser Asp Val Pro Arg Asp Leu Glu Val Val Ala Ala Thr Pro Thr
1               5                   10                  15

Ser Gln Leu Ile Ser Trp Thr Thr Arg His Ser Pro Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Thr Ala Thr Ile Ser Gly Leu Lys Pro
            50                  55                  60

Gly Val Asp Tyr Thr Ile Thr Val Tyr Ala Val Thr Met Pro Thr Asn
65                  70                  75                  80

Trp Arg Phe Pro His Arg Pro Ile Ser Ile Asn Tyr Arg Thr
                85                  90
```

<210> SEQ ID NO 78
<211> LENGTH: 94
<212> TYPE: PRT
<213> ORGANISM: Homo sapiens

<400> SEQUENCE: 78

```
Val Ser Asp Val Pro Arg Asp Leu Glu Ile Val Ala Ala Thr Pro Thr
1               5                   10                  15

Ser Arg Leu Ile Ser Trp Asn Arg Ser Gly Leu Gln Ser Gly Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Ser Ile Ala Thr Thr Ser Gly Leu Lys Pro
```

```
                    50                  55                  60
Gly Val Asp Tyr Thr Ile Thr Val Tyr Ala Val Thr Ser Asn Val Gly
 65                  70                  75                  80

Arg Leu Asp Thr Arg Tyr Pro Ile Ser Thr Asn Tyr Arg Thr
                 85                  90

<210> SEQ ID NO 79
<211> LENGTH: 93
<212> TYPE: PRT
<213> ORGANISM: Homo sapiens
<220> FEATURE:
<221> NAME/KEY: VARIANT
<222> LOCATION: 17, 30, 34
<223> OTHER INFORMATION: Xaa = Any Amino Acid

<400> SEQUENCE: 79

Val Ser Asp Val Pro Arg Asp Leu Glu Val Val Ala Ala Thr Pro Thr
  1               5                  10                  15

Xaa Arg Leu Ile Ser Trp Asn Arg Ser Gly Leu Gln Ser Xaa Tyr Tyr
                 20                  25                  30

Arg Xaa Thr Tyr Gly Glu Thr Gly Gly Asn Ser Pro Val Gln Glu Phe
             35                  40                  45

Thr Val Pro Pro Trp Ala Ser Ile Ala Ile Ser Gly Leu Lys Pro Gly
         50                  55                  60

Val Asp Tyr Thr Ile Thr Val Tyr Ala Val Thr Ser Asn Val Gly Arg
 65                  70                  75                  80

Leu Asp Thr Arg Tyr Pro Ile Phe Ile Asn Tyr Arg Thr
                 85                  90

<210> SEQ ID NO 80
<211> LENGTH: 76
<212> TYPE: PRT
<213> ORGANISM: Homo sapiens

<400> SEQUENCE: 80

Val Ser Asp Val Pro Arg Asp Leu Glu Val Val Ala Ala Thr Pro Thr
  1               5                  10                  15

Ser Arg Leu Ile Ser Trp Asn Arg Ser Gly Leu Gln Ser Arg Tyr Tyr
                 20                  25                  30

Arg Ile Thr Tyr Gly Glu Thr Gly Gly Asn Ser Pro Val Gln Glu Phe
             35                  40                  45

Thr Val Pro Pro Trp Ala Ser Ile Ala Thr Ile Ser Gly Leu Lys Pro
         50                  55                  60

Gly Val Asp Tyr Thr Ile Thr Val Tyr Ala Val Thr
 65                  70                  75

<210> SEQ ID NO 81
<211> LENGTH: 94
<212> TYPE: PRT
<213> ORGANISM: Homo sapiens

<400> SEQUENCE: 81

Val Ser Asp Val Pro Arg Asp Leu Glu Val Val Ala Ala Thr Pro Thr
  1               5                  10                  15

Ser Arg Leu Ile Ser Trp Asn Arg Ser Gly Leu Gln Ser Arg Tyr Tyr
                 20                  25                  30

Arg Ile Thr Tyr Gly Glu Thr Gly Gly Asn Ser Pro Val Gln Glu Phe
             35                  40                  45

Thr Val Pro Pro Trp Ala Ser Ile Ala Thr Ile Ser Gly Leu Lys Pro
```

```
            50                  55                  60
Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 82
<211> LENGTH: 94
<212> TYPE: PRT
<213> ORGANISM: Homo sapiens

<400> SEQUENCE: 82

Val Ser Asp Val Pro Arg Asp Leu Glu Val Val Ala Ala Thr Pro Thr
  1               5                  10                  15

Ser Arg Leu Ile Ser Cys Asn Arg Ser Gly Leu Gln Ser Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 83
<211> LENGTH: 94
<212> TYPE: PRT
<213> ORGANISM: Homo sapiens

<400> SEQUENCE: 83

Val Ser Asp Val Pro Arg Asp Leu Glu Val Val Ala Ala Thr Pro Thr
  1               5                  10                  15

Ser Arg Leu Ile Ser Trp Asn Arg Ser Gly Leu Gln Ser Arg Tyr Tyr
                 20                  25                  30

Arg Ile Thr Tyr Gly Glu Thr Gly Gly Ser Ser Pro Val Gln Glu Phe
                 35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Pro Thr His Asn
 65                  70                  75                  80

Trp Asn Asp Gln Thr Arg Ser Ile Ser Ile Asn Tyr Arg Thr
                 85                  90

<210> SEQ ID NO 84
<211> LENGTH: 94
<212> TYPE: PRT
<213> ORGANISM: Homo sapiens

<400> SEQUENCE: 84

Val Ser Asp Val Pro Arg Asp Leu Glu Val Val Ala Ala Thr Pro Thr
  1               5                  10                  15

Ser Arg Leu Ile Ser Trp Arg Pro Thr Ser Asn Pro Pro Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Pro Trp Ala Ser Ile Ala Thr Ile Gly Gly Leu Lys Pro
 50                  55                  60
```

-continued

Gly Val Asp Tyr Thr Ile Thr Val Tyr Ala Val Thr Ala Gln Thr Gly
65                  70                  75                  80

Tyr His Leu His Asp Lys Pro Ile Ser Ile Asn Tyr Arg Thr
                85                  90

<210> SEQ ID NO 85
<211> LENGTH: 93
<212> TYPE: PRT
<213> ORGANISM: Homo sapiens
<220> FEATURE:
<221> NAME/KEY: VARIANT
<222> LOCATION: 28, 51, 82
<223> OTHER INFORMATION: Xaa = Any Amino Acid

<400> SEQUENCE: 85

Val Ser Asp Val Pro Arg Asp Leu Glu Val Val Ala Ala Pro Thr Ser
1               5                   10                  15

Arg Leu Ile Ser Trp Arg Pro Gly Arg Thr Tyr Xaa Arg Tyr Tyr Arg
                20                  25                  30

Ile Thr Tyr Gly Glu Thr Gly Gly Asn Ser Pro Val Gln Glu Phe Thr
            35                  40                  45

Val Pro Xaa Trp Ala Asn Thr Ala Thr Ile Ser Gly Leu Lys Pro Gly
        50                  55                  60

Val Asp Tyr Thr Ile Thr Val Tyr Ala Val Thr Phe Pro Pro Gly Tyr
65                  70                  75                  80

Pro Xaa Thr Glu Met Pro Ile Ser Ile Asn Tyr Arg Thr
                85                  90

<210> SEQ ID NO 86
<211> LENGTH: 92
<212> TYPE: PRT
<213> ORGANISM: Homo sapiens

<400> SEQUENCE: 86

Ile Ser Asp Val Pro Arg Asp Leu Glu Val Val Ala Ala Thr Pro Thr
1               5                   10                  15

Ser Leu Leu Ile Ser Trp Arg Arg Trp Pro His Phe Asp Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Thr Ile Ala Thr Ile Ser Gly Leu Lys Pro
        50                  55                  60

Gly Val Asp Tyr Thr Ile Thr Val Tyr Ala Val Thr Asn Pro Leu Ser
65                  70                  75                  80

Pro Thr Thr Leu His Pro Pro Ile Asn Tyr Arg Thr
                85                  90

<210> SEQ ID NO 87
<211> LENGTH: 94
<212> TYPE: PRT
<213> ORGANISM: Homo sapiens

<400> SEQUENCE: 87

Val Ser Asp Val Pro Arg Asp Leu Glu Val Val Ala Ala Thr Pro Thr
1               5                   10                  15

Ser Arg Leu Ile Ser Trp Lys Pro Arg Arg Thr Asn Thr Arg Tyr Tyr
                20                  25                  30

Arg Ile Thr Tyr Gly Glu Thr Gly Gly Asn Ser Pro Val Gln Glu Phe
            35                  40                  45

```
Thr Val Pro Pro Trp Gly Thr Ile Ala Thr Ile Asn Gly Leu Lys Pro
    50                  55                  60

Gly Val Asp Tyr Thr Ile Thr Val Tyr Ala Val Thr Leu Gly Thr Gly
65                  70                  75                  80

Val Tyr Thr Arg Ala Gln Pro Ile Ser Ile Asn Tyr Arg Thr
                85                  90
```

<210> SEQ ID NO 88
<211> LENGTH: 94
<212> TYPE: PRT
<213> ORGANISM: Homo sapiens

<400> SEQUENCE: 88

```
Val Ser Asp Val Pro Arg Asp Leu Glu Val Val Ala Ala Thr Pro Thr
1               5                   10                  15

Ser Gln Leu Ile Ser Trp Pro Phe Gly Trp Tyr Pro Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Arg Thr Ala Thr Ile Ser Gly Leu Lys Pro
    50                  55                  60

Gly Val Asp Tyr Thr Ile Thr Val Tyr Ala Val Thr His Phe Pro Glu
65                  70                  75                  80

Ser Arg Arg Pro Ala Lys Pro Met Ser Ile Asn Tyr Arg Thr
                85                  90
```

<210> SEQ ID NO 89
<211> LENGTH: 94
<212> TYPE: PRT
<213> ORGANISM: Homo  sapiens

<400> SEQUENCE: 89

```
Val Ser Asp Val Pro Arg Asp Leu Glu Val Val Ala Ala Thr Pro Thr
1               5                   10                  15

Ser Leu Leu Ile Ser Trp His Thr Glu Arg Ser Phe Pro Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Gly Ser Ile Ala Thr Ile Ser Gly Leu Lys Pro
    50                  55                  60

Gly Val Asp Tyr Thr Ile Thr Val Tyr Ala Val Thr Glu His Tyr Arg
65                  70                  75                  80

Asp Thr Gly Thr Gly His Pro Ile Pro Ile Asn Tyr Arg Thr
                85                  90
```

<210> SEQ ID NO 90
<211> LENGTH: 94
<212> TYPE: PRT
<213> ORGANISM: Homo sapiens

<400> SEQUENCE: 90

```
Val Ser Asp Val Pro Arg Asp Leu Glu Val Val Ala Ala Thr Pro Thr
1               5                   10                  15

Ser Leu Leu Ile Ser Trp His Thr Glu Arg Ser Phe Pro Arg Tyr Tyr
                20                  25                  30

Arg Ile Thr Tyr Gly Glu Thr Gly Gly Asn Ser Pro Val Gln Glu Phe
            35                  40                  45
```

```
Thr Val Pro Pro Trp Gly Ser Ile Ala Thr Ile Ser Gly Leu Lys Pro
    50                  55                  60

Gly Val Asp Tyr Thr Ile Thr Val Tyr Ala Val Thr Glu His Tyr Arg
65                  70                  75                  80

Asp Thr Gly Thr Gly His Pro Ile Pro Ile Asn Tyr Arg Thr
                85                  90

<210> SEQ ID NO 91
<211> LENGTH: 94
<212> TYPE: PRT
<213> ORGANISM: Homo sapiens

<400> SEQUENCE: 91

Val Ser Asp Val Pro Arg Asp Leu Glu Val Val Ala Ala Thr Pro Thr
1               5                   10                  15

Ser Gln Leu Ile Ser Trp Lys Ser His Thr Phe His Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Thr Ala Ala Ile Ser Gly Leu Lys Pro
    50                  55                  60

Gly Ala Asp Tyr Thr Ile Thr Val Tyr Ala Val Thr Leu Asn Arg Ser
65                  70                  75                  80

Ser Pro Asn Ser Ala Arg Pro Ile Ser Ile Asn Tyr Arg Thr
                85                  90

<210> SEQ ID NO 92
<211> LENGTH: 94
<212> TYPE: PRT
<213> ORGANISM: Homo sapiens

<400> SEQUENCE: 92

Val Ser Asp Val Pro Arg Asp Leu Glu Val Val Ala Ala Thr Pro Thr
1               5                   10                  15

Ser Leu Leu Ile Ser Trp Arg Pro Gln Val Val Ser Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Asn His Lys Ala
65                  70                  75                  80

Asn His His Asp Ala Glu Pro Ile Ser Ile Asn Tyr Arg Thr
                85                  90

<210> SEQ ID NO 93
<211> LENGTH: 94
<212> TYPE: PRT
<213> ORGANISM: Homo sapiens

<400> SEQUENCE: 93

Val Ser Asp Val Pro Arg Asp Leu Glu Val Val Ala Ala Thr Pro Thr
1               5                   10                  15

Ser Arg Leu Ile Ser Trp Arg Pro Thr Ser Asn His Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Gly Gly Leu Lys Pro
```

```
                50              55              60
Gly Val Asp Tyr Thr Ile Thr Val Tyr Ala Val Thr Thr Thr Asn Glu
 65                  70                  75                  80

Asp His Val Tyr Ala Leu Pro Ile Ser Ile Asn Tyr Arg Ile
                 85                  90
```

<210> SEQ ID NO 94
<211> LENGTH: 94
<212> TYPE: PRT
<213> ORGANISM: Homo sapiens

<400> SEQUENCE: 94

```
Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Ser Pro Val Gln Glu Leu
                35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90
```

<210> SEQ ID NO 95
<211> LENGTH: 94
<212> TYPE: PRT
<213> ORGANISM: Homo sapiens

<400> SEQUENCE: 95

```
Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Gly Pro Val Gln Glu Phe
                35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Met Ser Asp
 65                  70                  75                  80

Thr Tyr Lys Tyr Asp Asp Pro Ile Ser Ile Asn Tyr Arg Thr
                 85                  90
```

<210> SEQ ID NO 96
<211> LENGTH: 94
<212> TYPE: PRT
<213> ORGANISM: Homo sapiens
<220> FEATURE:
<221> NAME/KEY: VARIANT
<222> LOCATION: 40
<223> OTHER INFORMATION: Xaa = Any Amino Acid

<400> SEQUENCE: 96

```
Val Ser Asp Val Pro Arg Asp Leu Glu Val Val Ala Ala Thr Pro Thr
 1               5                  10                  15

Ser Leu Leu Ile Ser Trp Asp Thr His Asn Ala Tyr Asn Gly Tyr Tyr
                20                  25                  30

Arg Ile Thr Tyr Gly Glu Thr Xaa Gly Asn Ser Pro Val Arg Glu Phe
```

```
              35                  40                  45
Thr Val Pro His Pro Glu Val Thr Ala Thr Ile Ser Gly Leu Lys Pro
    50                  55                  60

Gly Val Asp Asp Thr Ile Thr Val Tyr Ala Val Thr Asn His His Met
65                  70                  75                  80

Pro Leu Arg Ile Phe Gly Pro Ile Ser Ile Asn His Arg Thr
                85                  90

<210> SEQ ID NO 97
<211> LENGTH: 94
<212> TYPE: PRT
<213> ORGANISM: Homo sapiens
<220> FEATURE:
<221> NAME/KEY: VARIANT
<222> LOCATION: 13, 21
<223> OTHER INFORMATION: Xaa = Any Amino Acid

<400> SEQUENCE: 97

Val Ser Asp Val Pro Arg Asp Leu Glu Val Val Ala Xaa Thr Pro Thr
1               5                   10                  15

Ser Leu Leu Ile Xaa Trp Thr Arg Thr Asn Ala Asn Thr Arg Tyr Tyr
                20                  25                  30

Arg Ile Thr Tyr Gly Glu Thr Gly Gly Asn Ser Pro Val Gln Glu Phe
            35                  40                  45

Thr Ala Pro Asn Asn Pro Pro Thr Ala Thr Ile Gly Gly Leu Lys Pro
    50                  55                  60

Gly Val Asp Tyr Thr Ile Thr Val Tyr Ala Val Thr Pro Asp Gly Ser
65                  70                  75                  80

Arg His Met Leu Thr Lys Pro Ile Ser Ile Asn Tyr Arg Thr
                85                  90

<210> SEQ ID NO 98
<211> LENGTH: 94
<212> TYPE: PRT
<213> ORGANISM: Homo sapiens

<400> SEQUENCE: 98

Leu Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Ser Ile Ala Ala Ile Ser Gly Leu Lys Pro
    50                  55                  60

Gly Val Asp Tyr Thr Ile Thr Val Tyr Ala Val Thr Asp Lys Ser Asp
65                  70                  75                  80

Thr Tyr Lys Tyr Asp Asp Pro Ile Ser Ile Asn Tyr Arg Thr
                85                  90

<210> SEQ ID NO 99
<211> LENGTH: 94
<212> TYPE: PRT
<213> ORGANISM: Homo sapiens

<400> SEQUENCE: 99

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
```

```
            20                  25                  30

Arg Ile Thr Tyr Gly Glu Thr Gly Asn Ser Pro Val Gln Glu Leu
        35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn His Arg Thr
                 85                  90

<210> SEQ ID NO 100
<211> LENGTH: 94
<212> TYPE: PRT
<213> ORGANISM: Homo sapiens

<400> SEQUENCE: 100

Val Ser Asp Val Pro Arg Gly Leu Glu Val Val Ala Ala Thr Pro Thr
 1               5                  10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys His
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 101
<211> LENGTH: 94
<212> TYPE: PRT
<213> ORGANISM: Homo sapiens

<400> SEQUENCE: 101

Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
            20                  25                  30

Arg Ile Thr Tyr Gly Glu Thr Glu Gly Asn Ser Pro Val Gln Glu Phe
        35                  40                  45

Thr Val Pro Pro Trp Ala Ser Met Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 102
<211> LENGTH: 94
<212> TYPE: PRT
<213> ORGANISM: Homo sapiens

<400> SEQUENCE: 102

Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
            20                  25                  30
```

-continued

Arg Ile Thr Tyr Gly Glu Thr Gly Gly Asn Ser Pro Val Gln Glu Phe
                35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Thr Ser Ile Asn Tyr Arg Thr
                 85                  90

<210> SEQ ID NO 103
<211> LENGTH: 94
<212> TYPE: PRT
<213> ORGANISM: Homo sapiens

<400> SEQUENCE: 103

Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Ser Pro Val Gln Glu Phe
                35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Ala Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 104
<211> LENGTH: 94
<212> TYPE: PRT
<213> ORGANISM: Homo sapiens

<400> SEQUENCE: 104

Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Ser Pro Val Gln Glu Phe
                35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                 85                  90

<210> SEQ ID NO 105
<211> LENGTH: 94
<212> TYPE: PRT
<213> ORGANISM: Homo sapiens

<400> SEQUENCE: 105

Val Ser Asp Val Pro Arg Asp Leu Glu Val Val Ala Ala Thr Pro Thr
 1               5                  10                  15

Ser Arg Leu Ile Ser Trp Asn Arg Ser Gly Leu Gln Cys Arg Tyr Tyr
                20                  25                  30

```
Arg Ile Thr Tyr Gly Glu Thr Gly Asn Ser Pro Val Gln Glu Phe
            35                  40                  45

Thr Val Pro Pro Trp Ala Ser Ile Ala Thr Ile Ser Gly Leu Lys Pro
 50                  55                  60

Gly Val Asp Tyr Thr Ile Thr Val Tyr Ala Val Thr Asp Gln Arg Asp
 65                  70                  75                  80

Thr Tyr Arg Tyr Asp Asp Pro Ile Ser Thr Asn Cys Arg Thr
                85                  90
```

<210> SEQ ID NO 106
<211> LENGTH: 94
<212> TYPE: PRT
<213> ORGANISM: Homo sapiens

<400> SEQUENCE: 106

```
Val Ser Asp Val Pro Arg Asp Leu Glu Val Val Ala Ala Thr Pro Thr
 1               5                  10                  15

Ser Arg Leu Ile Ser Trp Arg Asn Ile Tyr Pro Ile Ala Arg Tyr Tyr
            20                  25                  30

Arg Ile Thr Tyr Gly Glu Thr Gly Asn Ser Pro Val Gln Glu Phe
            35                  40                  45

Thr Val Pro Pro Trp Ala Ser Ile Ala Thr Ile Ser Gly Leu Lys Pro
 50                  55                  60

Gly Ala Asp Tyr Thr Ile Thr Val Tyr Ala Val Thr Asp Lys Ser Asp
 65                  70                  75                  80

Thr Tyr Lys Tyr Asp Asp Pro Ile Ser Ile Asn Tyr Arg Thr
                85                  90
```

<210> SEQ ID NO 107
<211> LENGTH: 92
<212> TYPE: PRT
<213> ORGANISM: Homo sapiens
<220> FEATURE:
<221> NAME/KEY: VARIANT
<222> LOCATION: 27
<223> OTHER INFORMATION: Xaa = Any Amino Acid

<400> SEQUENCE: 107

```
Val Ser Asp Val Pro Arg Asp Leu Glu Val Val Ala Ala Thr Ala Thr
 1               5                  10                  15

Ser Gln Leu Ile Ser Trp Pro Trp Pro Ser Xaa Pro Thr Arg Tyr Tyr
            20                  25                  30

Arg Ile Thr Tyr Gly Glu Thr Glu Gly Asn Ser Pro Val Gln Glu Phe
            35                  40                  45

Thr Val Pro Pro Trp Ala Ser Thr Ala Thr Ile Ser Gly Ile Lys Pro
 50                  55                  60

Gly Val Asp Tyr Thr Ile Ala Val Tyr Ala Val Thr Met Pro Glu Arg
 65                  70                  75                  80

Lys Tyr Asp Lys Pro Ile Ser Ile Asn Tyr Arg Thr
                85                  90
```

<210> SEQ ID NO 108
<211> LENGTH: 94
<212> TYPE: PRT
<213> ORGANISM: Homo sapiens

<400> SEQUENCE: 108

```
Val Ser Asp Val Ser Arg Asp Leu Glu Ala Val Ala Ala Thr Pro Thr
 1               5                  10                  15
```

-continued

Ser Leu Leu Ile Ser Trp Asn Pro Asn Arg Ser Phe Ala Arg Tyr Tyr
            20                  25                  30

Arg Ile Thr Tyr Gly Glu Thr Gly Asn Ser Pro Val Gln Glu Phe
            35                  40                  45

Thr Val Pro Pro Trp Ala Ser Ile Ala Thr Ile Gly Gly Leu Lys Pro
 50                      55                  60

Arg Val Asp Tyr Thr Ile Thr Val Tyr Ala Val Thr Ala Gln Thr Gly
 65                  70                  75                  80

His His Leu His Asp Lys Ser Ile Pro Ile Asn Tyr Arg Thr
                85                  90

<210> SEQ ID NO 109
<211> LENGTH: 94
<212> TYPE: PRT
<213> ORGANISM: Homo sapiens

<400> SEQUENCE: 109

Val Ser Asp Val Pro Arg Asp Leu Glu Val Val Ala Ala Thr Pro Thr
 1               5                  10                  15

Ser Arg Leu Ile Ser Trp Arg Pro Gly Arg Thr Tyr Ser Arg Tyr Tyr
            20                  25                  30

Arg Ile Thr Tyr Gly Glu Thr Gly Gly Asn Ser Pro Val Gln Glu Ser
            35                  40                  45

Thr Val Pro Pro Trp Ala Asn Thr Ala Thr Ile Ser Gly Leu Lys Pro
 50                      55                  60

Gly Val Asp Tyr Thr Ile Thr Val Tyr Ala Val Thr Phe Pro Pro Gly
 65                  70                  75                  80

Tyr Pro Leu Thr Glu Met Pro Ile Ser Ile Asn Tyr Arg Thr
                85                  90

<210> SEQ ID NO 110
<211> LENGTH: 94
<212> TYPE: PRT
<213> ORGANISM: Homo sapiens

<400> SEQUENCE: 110

Val Ser Asp Val Pro Arg Asp Leu Glu Val Val Ala Ala Thr Pro Ser
 1               5                  10                  15

Ser Arg Leu Ile Ser Trp Arg Pro Gly Arg Thr Tyr Ser Arg Tyr Tyr
            20                  25                  30

Arg Ile Thr Tyr Gly Glu Thr Gly Gly Asn Ser Pro Val Gln Glu Phe
            35                  40                  45

Thr Val Pro Pro Trp Ala Asn Thr Ala Thr Ile Ser Gly Leu Lys Pro
 50                      55                  60

Gly Val Asp Tyr Thr Ile Ala Val Tyr Ala Val Thr Phe Pro Thr Gly
 65                  70                  75                  80

Tyr Pro Leu Thr Glu Met Pro Ile Ser Ile Asn Tyr Arg Thr
                85                  90

<210> SEQ ID NO 111
<211> LENGTH: 94
<212> TYPE: PRT
<213> ORGANISM: Homo sapiens

<400> SEQUENCE: 111

Val Ser Asp Val Pro Arg Asp Leu Glu Val Val Ala Ala Thr Pro Thr
 1               5                  10                  15

Ser Arg Leu Ile Ser Trp Arg Pro Gly Arg Thr Tyr Ser Arg Tyr Tyr

```
                    20                  25                  30

Arg Ile Thr Tyr Gly Glu Thr Gly Asn Ser Pro Val Gln Glu Phe
            35                  40                  45

Thr Val Pro Pro Trp Ala Asn Thr Ala Thr Ile Ser Gly Leu Lys Pro
         50                  55                  60

Gly Val Asp Tyr Thr Ile Thr Ala Tyr Ala Val Thr Tyr Thr His Ser
65                   70                  75                  80

Thr Pro Met Gln Asp Glu Pro Ile Ser Ile Asn Tyr Arg Thr
                 85                  90

<210> SEQ ID NO 112
<211> LENGTH: 94
<212> TYPE: PRT
<213> ORGANISM: Homo sapiens

<400> SEQUENCE: 112

Val Ser Asp Val Pro Arg Asp Leu Glu Val Val Ala Ala Thr Pro Thr
1               5                   10                  15

Ser Arg Leu Ile Ser Trp Asp Asn Ser Arg Pro Asn Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Gly Ser Ile Ala Thr Ile Ser Gly Leu Lys Pro
         50                  55                  60

Gly Val Lys Tyr Thr Ile Thr Val Tyr Ala Val Thr Thr Ser Glu Cys
65                   70                  75                  80

His Lys Leu Ser Ser Thr Ser Ile Ser Ile Asn Tyr Arg Thr
                 85                  90

<210> SEQ ID NO 113
<211> LENGTH: 91
<212> TYPE: PRT
<213> ORGANISM: Homo sapiens

<400> SEQUENCE: 113

Val Ser Asp Val Pro Arg Asp Leu Glu Val Val Ala Ala Thr Pro Thr
1               5                   10                  15

Ser Leu Leu Ile Ser Trp Thr Arg Thr Asn Ala Ser Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Asn Phe Trp Trp Ile Ser Gly Leu Lys Pro Gly Val Asp
         50                  55                  60

Tyr Thr Ile Thr Val Tyr Ala Val Ala Ser Pro Asp Glu Thr Ser Ala
65                   70                  75                  80

Tyr Ser Glu Pro Ile Ser Ile Asn Tyr Arg Thr
                 85                  90

<210> SEQ ID NO 114
<211> LENGTH: 92
<212> TYPE: PRT
<213> ORGANISM: Homo sapiens
<220> FEATURE:
<221> NAME/KEY: VARIANT
<222> LOCATION: 3, 18, 23
<223> OTHER INFORMATION: Xaa = Any Amino Acid

<400> SEQUENCE: 114

Val Ser Xaa Val Pro Arg Asp Leu Glu Val Val Ala Ala Thr Pro Thr
```

```
                  1               5                  10                 15
Ser Xaa Leu Ile Ser Trp Xaa Pro Arg Ser His His Asp Arg Tyr Tyr
                   20                  25                 30

Arg Ile Thr Tyr Gly Glu Thr Gly Gly Asn Ser Pro Val Gln Glu Phe
                   35                  40                 45

Thr Val Pro Pro Trp Gly Thr Ile Ala Thr Ile Asp Gly Leu Lys Pro
         50                  55                 60

Gly Val Gly Tyr Thr Val Thr Val Tyr Ala Val Thr Asp Asn Pro Asn
65                   70                 75                  80

Ser Ala Lys Ala Gln His Pro Ile Asn Ser Arg Thr
                 85                  90

<210> SEQ ID NO 115
<211> LENGTH: 94
<212> TYPE: PRT
<213> ORGANISM: Homo sapiens

<400> SEQUENCE: 115

Val Ser Asp Val Pro Arg Asp Leu Glu Val Val Ala Thr Pro Thr
1                5                  10                 15

Ser Gln Leu Ile Ser Trp Met Thr Pro His Asn His Val Arg Tyr Tyr
                   20                  25                 30

Gly Ile Thr Tyr Gly Glu Thr Gly Gly Asn Ser Pro Val Gln Glu Ser
                   35                  40                 45

Thr Val Pro Thr Gly Asn Ala Thr Ala Thr Ile Ser Gly Leu Lys Pro
         50                  55                 60

Gly Val Asp Tyr Thr Ile Thr Val Tyr Ala Val Thr Pro His His Gly
65                   70                 75                  80

His Phe Asp Leu Glu Pro Pro Ile Ser Ile Asn Tyr Arg Thr
                 85                  90

<210> SEQ ID NO 116
<211> LENGTH: 94
<212> TYPE: PRT
<213> ORGANISM: Homo sapiens

<400> SEQUENCE: 116

Val Ser Asp Val Pro Arg Asp Leu Glu Val Val Ala Ala Thr Ser Thr
1                5                  10                 15

Gly Leu Leu Ile Ser Trp Arg Thr Pro Ala Ser Pro His Gly Tyr Tyr
                   20                  25                 30

Arg Ile Thr Tyr Gly Glu Thr Gly Gly Asn Ser Pro Val Glu Glu Phe
                   35                  40                 45

Thr Val Pro Leu Leu Trp Pro Thr Ala Thr Ile Ser Gly Leu Lys Pro
         50                  55                 60

Gly Val Asp Tyr Thr Ile Thr Val Tyr Ala Val Thr Pro Thr His Met
65                   70                 75                  80

Leu Lys Pro Gln Ser Met Pro Ile Ser Ile Asn Tyr Arg Thr
                 85                  90

<210> SEQ ID NO 117
<211> LENGTH: 94
<212> TYPE: PRT
<213> ORGANISM: Homo sapiens

<400> SEQUENCE: 117

Val Ser Asp Val Pro Arg Asp Leu Glu Val Val Ala Ala Thr Pro Thr
1                5                  10                 15
```

```
Ser Leu Leu Ile Ser Trp Ser Pro Pro Asn Asp Ala His Arg Tyr Tyr
            20                  25                  30

Arg Ile Thr Tyr Gly Lys Thr Gly Gly Asp Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ser Val Val Tyr Ala Val Thr Asp Gln Gln Ser
 65                  70                  75                  80

Tyr Thr Tyr Tyr Ser Asn Pro Ile Ser Ile Asn Tyr Arg Thr
                85                  90

<210> SEQ ID NO 118
<211> LENGTH: 94
<212> TYPE: PRT
<213> ORGANISM: Homo sapiens
<220> FEATURE:
<221> NAME/KEY: VARIANT
<222> LOCATION: 28
<223> OTHER INFORMATION: Xaa = Any Amino Acid

<400> SEQUENCE: 118

Val Ser Asp Val Pro Ser Asp Leu Glu Val Val Ala Ala Thr Pro Thr
 1               5                  10                  15

Ser Leu Leu Ile Ser Trp Glu Gln Ser Pro Thr Xaa Gly Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Arg Lys Pro
        50                  55                  60

Gly Ala Asp Tyr Thr Ile Thr Val Tyr Ala Val Thr Ile Glu Lys Asp
 65                  70                  75                  80

Arg Ile Pro Leu Phe Gly Pro Ile Ser Ile Ser Tyr Arg Thr
                85                  90

<210> SEQ ID NO 119
<211> LENGTH: 94
<212> TYPE: PRT
<213> ORGANISM: Homo sapiens

<400> SEQUENCE: 119

Val Ser Asp Val Pro Ser Asp Leu Glu Val Val Ala Ala Thr Pro Thr
 1               5                  10                  15

Ser Leu Leu Ile Ser Trp Glu Gln Ser Pro Thr Tyr Gly Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Arg Lys Pro
        50                  55                  60

Gly Ala Asp Tyr Thr Ile Thr Val Tyr Ala Val Thr Ile Glu Lys Asp
 65                  70                  75                  80

Arg Ile Pro Leu Phe Gly Pro Ile Ser Ile Ser Tyr Arg Thr
                85                  90

<210> SEQ ID NO 120
<211> LENGTH: 94
<212> TYPE: PRT
<213> ORGANISM: Homo sapiens
<220> FEATURE:
<221> NAME/KEY: VARIANT
```

<222> LOCATION: 28
<223> OTHER INFORMATION: Xaa = Any Amino Acid

<400> SEQUENCE: 120

Val Ser Asp Val Pro Ser Asp Leu Glu Val Ala Ala Thr Pro Thr
1               5                   10                  15

Ser Leu Leu Ile Ser Trp Glu Gln Ser Pro Thr Xaa Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Arg Lys Pro
    50                  55                  60

Gly Ala Asp Tyr Thr Ile Thr Val Tyr Ala Val Thr Ile Glu Lys Asp
65                  70                  75                  80

Arg Ile Pro Leu Phe Gly Pro Ile Ser Ile Ser Tyr Arg Thr
                85                  90

<210> SEQ ID NO 121
<211> LENGTH: 94
<212> TYPE: PRT
<213> ORGANISM: Homo sapiens

<400> SEQUENCE: 121

Val Pro Asp Val Pro Arg Asp Leu Glu Val Val Ala Ala Thr Pro Thr
1               5                   10                  15

Ser Leu Leu Ile Ser Trp Asp Thr His Asn Ala Tyr Asn Gly Tyr Tyr
                20                  25                  30

Arg Ile Thr Tyr Gly Glu Thr Gly Gly Ser Ser Pro Ala Gln Glu Phe
            35                  40                  45

Thr Val Pro His Pro Glu Val Thr Ala Thr Ile Ser Gly Leu Lys Pro
    50                  55                  60

Gly Val Asp Asp Thr Ile Thr Val Tyr Ala Val Thr Ile His His Met
65                  70                  75                  80

Pro Leu Arg Ile Phe Gly Pro Ile Ser Ile Asn Tyr Arg Thr
                85                  90

<210> SEQ ID NO 122
<211> LENGTH: 94
<212> TYPE: PRT
<213> ORGANISM: Homo sapiens

<400> SEQUENCE: 122

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Asp Glu Ser Asp
65                  70                  75                  80

Thr Tyr Lys Tyr Asp Asp Pro Val Ser Ile Asn Tyr Arg Thr
                85                  90

<210> SEQ ID NO 123
<211> LENGTH: 94
<212> TYPE: PRT

```
<213> ORGANISM: Homo sapiens

<400> SEQUENCE: 123

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Asp Glu Ser Asp
65                  70                  75                  80

Thr Tyr Lys Tyr Asp Asp Pro Val Ser Thr Asn Tyr Arg Thr
                85                  90

<210> SEQ ID NO 124
<211> LENGTH: 94
<212> TYPE: PRT
<213> ORGANISM: Homo sapiens

<400> SEQUENCE: 124

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Gly Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Pro Asn Val Gly
65                  70                  75                  80

Arg Leu Asp Thr Arg Tyr Pro Ile Ser Ile Asp Cys Arg Thr
                85                  90

<210> SEQ ID NO 125
<211> LENGTH: 94
<212> TYPE: PRT
<213> ORGANISM: Homo sapiens
<220> FEATURE:
<221> NAME/KEY: VARIANT
<222> LOCATION: 86
<223> OTHER INFORMATION: Xaa = Any Amino Acid

<400> SEQUENCE: 125

Val Ser Asp Val Pro Arg Asp Leu Glu Val Val Ala Ala Thr Pro Thr
1               5                   10                  15

Ser Arg Leu Ile Ser Trp Asn Arg Ser Gly Leu Gln Ser Arg Tyr Tyr
            20                  25                  30

Arg Thr Thr Tyr Gly Glu Thr Gly Gly Asn Ser Pro Val Gln Glu Phe
        35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Ser Asn Val Gly
65                  70                  75                  80

Arg Leu Asp Thr Arg Xaa Pro Ile Ser Ile Asn Tyr Arg Thr
                85                  90
```

```
<210> SEQ ID NO 126
<211> LENGTH: 94
<212> TYPE: PRT
<213> ORGANISM: Homo sapiens
<220> FEATURE:
<221> NAME/KEY: VARIANT
<222> LOCATION: 75
<223> OTHER INFORMATION: Xaa = Any Amino Acid

<400> SEQUENCE: 126

Val Ser Asp Val Pro Arg Asp Leu Glu Val Val Ala Ala Thr Pro Thr
 1               5                  10                  15

Ser Arg Leu Ile Ser Trp Arg Thr Met Pro Val Thr Ala Arg Tyr Tyr
            20                  25                  30

Arg Ile Thr Tyr Gly Glu Thr Gly Gly Asp Ser Pro Val Gln Glu Phe
        35                  40                  45

Thr Val Pro Pro Trp Ala Ser Ile Ala Ala Ile Ser Gly Leu Lys Pro
    50                  55                  60

Gly Ala Asp Tyr Thr Ile Thr Val Tyr Ala Xaa Thr Ser Ala Thr Pro
65                  70                  75                  80

Ser Arg Pro Asn Val His Pro Ile Ser Ile Asn Leu Thr Thr
                85                  90

<210> SEQ ID NO 127
<211> LENGTH: 88
<212> TYPE: PRT
<213> ORGANISM: Homo sapiens

<400> SEQUENCE: 127

Val Ser Asp Val Pro Gly Asp Leu Glu Val Val Ala Ala Thr Pro Thr
 1               5                  10                  15

Ser Leu Leu Ile Gly Trp Ser Met Thr Pro Asn Trp Pro Arg Tyr Tyr
            20                  25                  30

Arg Ile Ala Tyr Gly Glu Thr Gly Gly Asp Ser Pro Val Gln Glu Phe
        35                  40                  45

Thr Val Pro Pro Trp Ala Ser Ile Ala Ile Ile Gly Gly Leu Lys Pro
    50                  55                  60

Gly Val Asp Tyr Thr Ile Thr Val Tyr Ala Val Thr His Arg Asp Thr
65                  70                  75                  80

Pro Ile Ser Ile Asn Tyr Arg Thr
                85

<210> SEQ ID NO 128
<211> LENGTH: 90
<212> TYPE: PRT
<213> ORGANISM: Homo sapiens

<400> SEQUENCE: 128

Val Ser Asp Val Pro Arg Asp Leu Glu Val Val Ala Ala Thr Pro Ile
 1               5                  10                  15

Ser Gln Leu Thr Ser Trp Gln Pro Gln Pro Asn Gly Ser Arg Tyr Tyr
            20                  25                  30

Arg Ile Ala Tyr Gly Glu Thr Gly Gly Asn Ser Pro Val Arg Glu Phe
        35                  40                  45

Thr Val Pro Ala Arg Glu Gln Thr Ala Thr Ser Gly Leu Lys Pro Gly
    50                  55                  60

Val Asp Tyr Ala Ile Thr Val Tyr Ala Ala Thr His Gly Lys Pro Pro
65                  70                  75                  80

His Ile His Phe Thr Ile Asn Tyr Arg Thr
```

<210> SEQ ID NO 129
<211> LENGTH: 94
<212> TYPE: PRT
<213> ORGANISM: Homo sapiens
<220> FEATURE:
<221> NAME/KEY: VARIANT
<222> LOCATION: 2, 9, 12, 22
<223> OTHER INFORMATION: Xaa = Any Amino Acid

<400> SEQUENCE: 129

Val Xaa Asp Val Pro Arg Asp Leu Xaa Val Val Xaa Ala Thr Pro Thr
1               5                   10                  15

Ser Leu Leu Ile Ser Xaa Arg Ser Gly Asn Arg Thr Thr Arg Tyr Tyr
            20                  25                  30

Arg Ile Thr Tyr Gly Asp Thr Gly Gly Asn Ser Pro Val Gln Glu Phe
        35                  40                  45

Thr Met Pro Pro Trp Ala Thr Val Ala Ala Ile Ser Gly Leu Lys Pro
    50                  55                  60

Gly Val Asp Tyr Thr Ile Thr Val Tyr Ala Val Thr Thr His Asn Ser
65                  70                  75                  80

Thr Ala Gln Pro Glu Tyr Pro Ile Pro Phe Asn Arg Arg Thr
                85                  90

<210> SEQ ID NO 130
<211> LENGTH: 94
<212> TYPE: PRT
<213> ORGANISM: Homo sapiens

<400> SEQUENCE: 130

Val Ser Asp Val Pro Arg Asp Leu Glu Val Val Ala Ala Thr Pro Thr
1               5                   10                  15

Ser Leu Leu Ile Ser Trp Arg Pro Gly Arg Thr Tyr Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Ala Asn Thr Ala Thr Ile Ser Cys Leu Lys Pro
    50                  55                  60

Gly Val Asp Tyr Thr Ile Thr Val Tyr Ala Val Ala Phe Pro Pro Gly
65                  70                  75                  80

Tyr Pro Leu Thr Glu Met Pro Ile Ser Ile Asn Tyr Arg Thr
                85                  90

<210> SEQ ID NO 131
<211> LENGTH: 94
<212> TYPE: PRT
<213> ORGANISM: Homo sapiens

<400> SEQUENCE: 131

Val Ser Asp Val Pro Arg Asp Leu Glu Val Val Ala Ala Thr Pro Thr
1               5                   10                  15

Ser Arg Leu Ile Ser Trp Arg Pro Gly Arg Ala Tyr Ser Arg Tyr Phe
            20                  25                  30

Arg Ile Thr Tyr Gly Glu Thr Gly Gly Asn Ser Pro Val Gln Glu Phe
        35                  40                  45

Thr Val Pro Pro Trp Ala Asn Thr Ala Thr Ile Ser Gly Leu Lys Pro
    50                  55                  60

Gly Val Asp Tyr Thr Ile Ala Val Tyr Ala Val Thr Phe Pro Pro Arg

```
                65                  70                  75                  80
Tyr Pro Leu Thr Glu Met Pro Ile Ser Ile Asn Tyr Arg Ala
                    85                  90
```

<210> SEQ ID NO 132
<211> LENGTH: 94
<212> TYPE: PRT
<213> ORGANISM: Homo sapiens

<400> SEQUENCE: 132

```
Val Ser Asp Val Pro Arg Asp Leu Glu Val Ala Ala Thr Pro Thr
  1               5                  10                  15

Ser Arg Leu Ile Ser Trp Arg Pro Gly Arg Thr Tyr Ser Arg Tyr Tyr
                20                  25                  30

Arg Ile Thr Tyr Gly Glu Ala Gly Gly Asn Ser Pro Val Gln Glu Phe
                35                  40                  45

Thr Val Pro Pro Trp Ala Ser Ile Ala Thr Ile Ser Gly Leu Lys Pro
            50                  55                  60

Gly Val Asp Tyr Thr Ile Thr Val Tyr Ala Val Thr Asp Lys Ser Gly
 65                  70                  75                  80

Thr Tyr Arg Tyr Asp Asp Pro Ile Ser Ile Asn Tyr Arg Thr
                    85                  90
```

<210> SEQ ID NO 133
<211> LENGTH: 94
<212> TYPE: PRT
<213> ORGANISM: Homo sapiens

<400> SEQUENCE: 133

```
Val Ser Asp Val Pro Arg Asp Leu Arg Val Ala Ala Thr Pro Thr
  1               5                  10                  15

Ser Arg Leu Ile Ser Trp Arg Pro Ala Ser Asn Pro Ala Arg Tyr Tyr
                20                  25                  30

Arg Ile Thr Tyr Gly Glu Thr Gly Gly Asn Ser Pro Val Gln Glu Phe
                35                  40                  45

Thr Val Pro Pro Trp Ala Ser Val Ala Thr Ile Gly Gly Leu Lys Pro
            50                  55                  60

Gly Val Asp Tyr Thr Val Thr Val Tyr Ala Val Thr Ala Gln Thr Gly
 65                  70                  75                  80

His Arg Leu His Asp Lys Pro Ile Ser Ile Asn Tyr Arg Thr
                    85                  90
```

<210> SEQ ID NO 134
<211> LENGTH: 87
<212> TYPE: PRT
<213> ORGANISM: Homo sapiens

<400> SEQUENCE: 134

```
Val Ser Asp Val Pro Arg Asp Leu Glu Val Ala Ala Thr Pro Ser
  1               5                  10                  15

Leu Leu Ile Ser Trp Arg Pro Pro Ala Asp Leu Asn Arg Tyr Tyr Arg
                20                  25                  30

Ile Thr Tyr Gly Glu Thr Gly Gly Asn Ser Pro Val Gln Glu Phe Thr
                35                  40                  45

Val Pro Pro Trp Gly Thr Val Ala Thr Val Asn Gly Leu Lys Pro Gly
            50                  55                  60

Val Gly Tyr Thr Ile Thr Val Tyr Ala Val Thr His Arg Asp Thr Pro
 65                  70                  75                  80
```

```
Ile Ser Ile Asn Tyr Arg Ala
            85

<210> SEQ ID NO 135
<211> LENGTH: 93
<212> TYPE: PRT
<213> ORGANISM: Homo sapiens

<400> SEQUENCE: 135

Val Thr Asp Val Pro Arg Gly Leu Lys Ile Ala Ala Thr Pro Ser
 1               5                  10                  15

Leu Leu Ile Ser Trp Arg Asn Ala Lys Asp Pro Gly Arg Tyr Tyr Arg
            20                  25                  30

Ile Thr Tyr Gly Glu Thr Gly Gly Ser Ser Pro Val Gln Glu Phe Thr
            35                  40                  45

Val Pro Pro Trp Gly Thr Ile Ala Ala Ile Asn Gly Leu Lys Pro Gly
    50                  55                  60

Val Asp Tyr Thr Ile Thr Val Tyr Ala Val Thr Ala Asn Pro Gly
65                  70                  75                  80

Pro Thr Gln His Arg Pro Ile Pro Ile Asn Tyr Arg Thr
                85                  90

<210> SEQ ID NO 136
<211> LENGTH: 94
<212> TYPE: PRT
<213> ORGANISM: Homo sapiens

<400> SEQUENCE: 136

Val Ser Asp Val Pro Arg Asp Leu Glu Val Val Ala Ala Asp Pro His
 1               5                  10                  15

Gln Pro Leu Ile Cys Trp Ala Ser Pro Pro Met Trp Cys Arg Tyr Tyr
            20                  25                  30

Arg Ile Thr Tyr Gly Glu Ser Gly Gly Asn Ser Pro Val Gln Glu Phe
            35                  40                  45

Thr Val Pro Pro Trp Ala Thr Ala Ala Ile Ser Gly Leu Lys Pro
    50                  55                  60

Gly Val Asp Tyr Thr Ile Thr Val His Ala Val Thr Asp Glu Ser Trp
65                  70                  75                  80

Ser Asp Arg Ser Met Asp Pro Ile Ser Ile Asn Cys Arg Thr
                85                  90

<210> SEQ ID NO 137
<211> LENGTH: 94
<212> TYPE: PRT
<213> ORGANISM: Homo sapiens

<400> SEQUENCE: 137

Val Ser Asp Val Pro Arg Asp Leu Lys Val Val Ala Ala Thr Pro Thr
 1               5                  10                  15

Ser Arg Leu Ile Ser Trp Thr His Asp Asn Val Pro Ala Arg Tyr Tyr
            20                  25                  30

Arg Ile Thr Tyr Gly Glu Thr Gly Gly Asn Ser Pro Val Gln Glu Leu
            35                  40                  45

Thr Val Pro Pro Trp Ala Ser Ile Ala Thr Ile Ser Gly Leu Lys Pro
    50                  55                  60

Gly Val Asp Tyr Thr Ile Thr Val Tyr Ala Val Thr Leu Tyr Thr Gly
65                  70                  75                  80
```

Asn His Arg Pro Glu His Pro Ile Ser Ile Asn Tyr Arg Thr
              85                  90

<210> SEQ ID NO 138
<211> LENGTH: 93
<212> TYPE: PRT
<213> ORGANISM: Homo sapiens

<400> SEQUENCE: 138

Val Ser Asp Val Pro Arg Asp Pro Val Val Ala Ala Thr Pro Thr
 1               5                  10                  15

Ser Leu Leu Ile Ser Trp Tyr Arg His Thr Tyr Arg Asp Arg Tyr Tyr
              20                  25                  30

Arg Val Thr Tyr Gly Glu Thr Arg Gly Asn Ser Pro Ile Arg Glu Phe
              35                  40                  45

Thr Val Pro Pro Trp Ala Thr Ile Ala Thr Ile Ser Gly Leu Lys Pro
         50                  55                  60

Gly Val Asp Tyr Thr Ile Ala Val Tyr Ala Val Thr Ala Gly Tyr
 65                  70                  75                  80

Asp Val His Thr Lys Arg Pro Ile Ser Ile Asn Arg Thr
              85                  90

<210> SEQ ID NO 139
<211> LENGTH: 94
<212> TYPE: PRT
<213> ORGANISM: Homo sapiens

<400> SEQUENCE: 139

Val Ser Asp Val Pro Arg Asp Leu Glu Val Val Ala Ala Thr Pro Thr
 1               5                  10                  15

Gly Leu Leu Ile Ser Trp Arg Asn Asn Gln Tyr Thr Pro Arg His Tyr
              20                  25                  30

Gly Ile Thr Tyr Gly Glu Thr Gly Gly Lys Ser Pro Val Gln Glu Phe
              35                  40                  45

Thr Val Pro Glu Leu Asn Pro Thr Ala Thr Ile Ser Arg Leu Lys Pro
         50                  55                  60

Gly Val Asp Tyr Thr Ile Thr Val Tyr Ala Val Thr Gln Asn Gly Thr
 65                  70                  75                  80

Pro Arg Val Ile Tyr Gly Pro Ile Ser Ile Asn Tyr Arg Thr
              85                  90

<210> SEQ ID NO 140
<211> LENGTH: 89
<212> TYPE: PRT
<213> ORGANISM: Homo sapiens

<400> SEQUENCE: 140

Val Ser Asp Val Pro Arg Asp Leu Glu Val Val Ala Ala Thr Pro Thr
 1               5                  10                  15

Ser Leu Leu Asn Val Pro Ile Ile Arg Tyr Tyr Arg Ile Thr Tyr Gly
              20                  25                  30

Glu Thr Gly Gly Asn Ser Pro Val Gln Glu Phe Thr Val Pro Ala Pro
              35                  40                  45

Lys Ala Ile Ala Thr Thr Ser Gly Leu Lys Pro Gly Val Asp Tyr Thr
         50                  55                  60

Ile Thr Val Tyr Gly Val Thr Ser His Arg Asn His Phe His Val Glu
 65                  70                  75                  80

Thr Pro Ile Ser Ile Asn Tyr Gln Ala

-continued

<210> SEQ ID NO 141
<211> LENGTH: 21
<212> TYPE: PRT
<213> ORGANISM: Homo sapiens

<400> SEQUENCE: 141

Asp Ala Pro Ala Val Thr Val Gly Ser Lys Ser Gly Arg Gly Asp Ser
1               5                   10                  15

Pro Ala Ser Ser Lys
            20

<210> SEQ ID NO 142
<211> LENGTH: 21
<212> TYPE: PRT
<213> ORGANISM: Homo sapiens

<400> SEQUENCE: 142

Ala Ser Pro Pro Met Trp Cys Pro Trp Ala Thr Glu Tyr Leu Pro Glu
1               5                   10                  15

Trp Asn Met Thr Gln
            20

<210> SEQ ID NO 143
<211> LENGTH: 21
<212> TYPE: PRT
<213> ORGANISM: Homo sapiens

<400> SEQUENCE: 143

Asn Arg Ser Gly Leu Gln Ser Pro Trp Ala Ser Asp Lys Ser Asp Thr
1               5                   10                  15

Tyr Lys Tyr Asp Asp
            20

<210> SEQ ID NO 144
<211> LENGTH: 21
<212> TYPE: PRT
<213> ORGANISM: Homo sapiens

<400> SEQUENCE: 144

Arg Pro Thr Ser Asn Pro Pro Trp Ala Ser Ala Gln Thr Gly His
1               5                   10                  15

His Leu His Asp Lys
            20

<210> SEQ ID NO 145
<211> LENGTH: 21
<212> TYPE: PRT
<213> ORGANISM: Homo sapiens

<400> SEQUENCE: 145

His Thr Glu Arg Ser Phe Pro Pro Trp Gly Ser Glu His Tyr Arg Asp
1               5                   10                  15

Thr Gly Thr Gly His
            20

<210> SEQ ID NO 146
<211> LENGTH: 21
<212> TYPE: PRT
<213> ORGANISM: Homo sapiens

<400> SEQUENCE: 146

Thr Thr Arg His Ser Pro Val Pro Trp Ala Thr Met Pro Thr Asn Trp
1               5                   10                  15

Arg Phe Pro His Arg
            20

<210> SEQ ID NO 147
<211> LENGTH: 21
<212> TYPE: PRT
<213> ORGANISM: Homo sapiens

<400> SEQUENCE: 147

Arg Pro Asn Pro Arg Leu Ser Gly Leu Phe Ser Pro Lys Glu Thr Ser
1               5                   10                  15

Asn Ile Phe Ile Ala
            20

<210> SEQ ID NO 148
<211> LENGTH: 21
<212> TYPE: PRT
<213> ORGANISM: Homo sapiens

<400> SEQUENCE: 148

Ser Pro Pro Asn Asp Ala His Gly Ser Lys Ser Asp Gln Gln Ser Tyr
1               5                   10                  15

Thr Tyr Tyr Ser Asn
            20

<210> SEQ ID NO 149
<211> LENGTH: 21
<212> TYPE: PRT
<213> ORGANISM: Homo sapiens

<400> SEQUENCE: 149

Arg Thr Pro Ala Ser Pro His Leu Leu Trp Pro Pro Thr His Met Leu
1               5                   10                  15

Lys Pro Gln Ser Met
            20

<210> SEQ ID NO 150
<211> LENGTH: 21
<212> TYPE: PRT
<213> ORGANISM: Homo sapiens

<400> SEQUENCE: 150

Tyr Arg His Thr Tyr Arg Asp Pro Trp Ala Thr Asp Thr Gly Tyr Asp
1               5                   10                  15

Val His Thr Lys Arg
            20

<210> SEQ ID NO 151
<211> LENGTH: 21
<212> TYPE: PRT
<213> ORGANISM: Homo sapiens

<400> SEQUENCE: 151

Asn Arg Ser Gly Leu Gln Ser Pro Trp Ala Ser Ser Asn Val Gly Arg
1               5                   10                  15

Leu Asp Thr Arg Tyr
            20

<210> SEQ ID NO 152

```
<211> LENGTH: 21
<212> TYPE: PRT
<213> ORGANISM: Homo sapiens

<400> SEQUENCE: 152

Asp Thr His Asn Ala Tyr Asn His Pro Glu Val Asn His His Met Pro
  1               5                  10                  15

Leu Arg Ile Phe Gly
            20

<210> SEQ ID NO 153
<211> LENGTH: 21
<212> TYPE: PRT
<213> ORGANISM: Homo sapiens

<400> SEQUENCE: 153

Arg Pro Thr Ser Asn Pro Pro Trp Ala Ser Pro Val Tyr Pro Met
  1               5                  10                  15

His Ser Met Leu Ser
            20

<210> SEQ ID NO 154
<211> LENGTH: 21
<212> TYPE: PRT
<213> ORGANISM: Homo sapiens

<400> SEQUENCE: 154

Arg Asn Ile Tyr Pro Ile Ala Pro Trp Ala Ser Asp Lys Ser Asp Thr
  1               5                  10                  15

Tyr Lys Tyr Asp Asp
            20

<210> SEQ ID NO 155
<211> LENGTH: 21
<212> TYPE: PRT
<213> ORGANISM: Homo sapiens

<400> SEQUENCE: 155

Asn Arg Ser Gly Leu Gln Cys Pro Trp Ala Ser Asp Gln Arg Asp Thr
  1               5                  10                  15

Tyr Lys Tyr Asp Asp
            20

<210> SEQ ID NO 156
<211> LENGTH: 21
<212> TYPE: PRT
<213> ORGANISM: Homo sapiens

<400> SEQUENCE: 156

Arg Pro Gly Arg Thr Tyr Ser Pro Trp Ala Asn Phe Pro Thr Gly Tyr
  1               5                  10                  15

Pro Leu Thr Glu Met
            20

<210> SEQ ID NO 157
<211> LENGTH: 21
<212> TYPE: PRT
<213> ORGANISM: Homo sapiens

<400> SEQUENCE: 157

Arg Pro Gly Arg Thr Tyr Ser Pro Trp Ala Asn Phe Pro Pro Gly Tyr
  1               5                  10                  15
```

Pro Leu Thr Glu Met
            20

<210> SEQ ID NO 158
<211> LENGTH: 21
<212> TYPE: PRT
<213> ORGANISM: Homo sapiens

<400> SEQUENCE: 158

Met Thr Pro His Asn His Val Thr Gly Asn Ala Pro His His Gly His
1               5                   10                  15

Phe Asp Leu Glu Pro
            20

<210> SEQ ID NO 159
<211> LENGTH: 21
<212> TYPE: PRT
<213> ORGANISM: Homo sapiens

<400> SEQUENCE: 159

Thr Arg Thr Asn Ala Ser Thr Asn Phe Trp Trp Ser Pro Asp Glu Thr
1               5                   10                  15

Ser Ala Tyr Ser Glu
            20

<210> SEQ ID NO 160
<211> LENGTH: 21
<212> TYPE: PRT
<213> ORGANISM: Homo sapiens

<400> SEQUENCE: 160

Asn Arg Ser Gly Leu Gln Ser Pro Trp Ala Ser Asp Lys Ser Asp Thr
1               5                   10                  15

Tyr Lys Tyr Asp Asp
            20

<210> SEQ ID NO 161
<211> LENGTH: 21
<212> TYPE: PRT
<213> ORGANISM: Homo sapiens

<400> SEQUENCE: 161

Arg Pro Gly Arg Thr Tyr Ser Pro Trp Ala Asn Tyr Thr His Ser Thr
1               5                   10                  15

Pro Met Gln Asp Glu
            20

<210> SEQ ID NO 162
<211> LENGTH: 21
<212> TYPE: PRT
<213> ORGANISM: Homo sapiens

<400> SEQUENCE: 162

Arg Thr Pro Ala Ser Pro His Leu Leu Trp Pro Pro Thr His Met Leu
1               5                   10                  15

Lys Pro Gln Ser Met
            20

<210> SEQ ID NO 163
<211> LENGTH: 21
<212> TYPE: PRT
<213> ORGANISM: Homo sapiens -continued

<400> SEQUENCE: 163

Thr Arg Thr Asn Ala Asn Thr Asn Asn Pro Pro Pro Asp Gly Ser Arg
1               5                   10                  15

His Met Leu Thr Lys
            20

<210> SEQ ID NO 164
<211> LENGTH: 21
<212> TYPE: PRT
<213> ORGANISM: Homo sapiens

<400> SEQUENCE: 164

Asp Asn Ser Arg Pro Asn Thr Pro Trp Gly Ser Thr Ser Glu Cys His
1               5                   10                  15

Lys Leu Ser Ser Thr
            20

<210> SEQ ID NO 165
<211> LENGTH: 21
<212> TYPE: PRT
<213> ORGANISM: Homo sapiens

<400> SEQUENCE: 165

Asn Pro Asn Arg Ser Phe Ala Pro Trp Ala Ser Ala Gln Thr Gly His
1               5                   10                  15

His Leu His Asp Lys
            20

<210> SEQ ID NO 166
<211> LENGTH: 15
<212> TYPE: PRT
<213> ORGANISM: Homo sapiens

<400> SEQUENCE: 166

Ser Met Thr Pro Asn Trp Pro Pro Trp Ala Ser His Arg Asp Thr
1               5                   10                  15

<210> SEQ ID NO 167
<211> LENGTH: 21
<212> TYPE: PRT
<213> ORGANISM: Homo sapiens

<400> SEQUENCE: 167

Asp Thr His Asn Ala Tyr Asn His Pro Glu Val Ile His His Met Pro
1               5                   10                  15

Leu Arg Ile Phe Gly
            20

<210> SEQ ID NO 168
<211> LENGTH: 20
<212> TYPE: PRT
<213> ORGANISM: Homo sapiens

<400> SEQUENCE: 168

Ala Ser Pro Pro Met Trp Pro Trp Ala Thr Asp Glu Ser Trp Ser Asp
1               5                   10                  15

Arg Ser Met Asp
            20

<210> SEQ ID NO 169
<211> LENGTH: 15
<212> TYPE: PRT

-continued

<213> ORGANISM: Homo sapiens

<400> SEQUENCE: 169

Arg Pro Pro Ala Asp Leu Asn Pro Trp Gly Thr His Arg Asp Thr
1               5                   10                  15

<210> SEQ ID NO 170
<211> LENGTH: 21
<212> TYPE: PRT
<213> ORGANISM: Homo sapiens

<400> SEQUENCE: 170

Glu Gln Ser Pro Thr Tyr Gly Gly Ser Lys Ser Ile Glu Lys Asp Arg
1               5                   10                  15

Ile Pro Leu Phe Gly
            20

<210> SEQ ID NO 171
<211> LENGTH: 21
<212> TYPE: PRT
<213> ORGANISM: Homo sapiens

<400> SEQUENCE: 171

Arg Pro Gly Arg Thr Tyr Ser Pro Trp Ala Asn Phe Pro Pro Gly Tyr
1               5                   10                  15

Pro Leu Thr Glu Met
            20

<210> SEQ ID NO 172
<211> LENGTH: 21
<212> TYPE: PRT
<213> ORGANISM: Homo sapiens

<400> SEQUENCE: 172

Arg Pro Gly Arg Thr Tyr Ser Pro Trp Ala Ser Asp Lys Ser Gly Thr
1               5                   10                  15

Tyr Arg Tyr Asp Asp
            20

<210> SEQ ID NO 173
<211> LENGTH: 21
<212> TYPE: PRT
<213> ORGANISM: Homo sapiens

<400> SEQUENCE: 173

Tyr Arg His Thr Tyr Arg Asp Pro Trp Ala Thr Asp Ala Gly Tyr Asp
1               5                   10                  15

Val His Thr Lys Arg
            20

<210> SEQ ID NO 174
<211> LENGTH: 21
<212> TYPE: PRT
<213> ORGANISM: Homo sapiens

<400> SEQUENCE: 174

Arg Thr Met Pro Val Thr Ala Pro Trp Ala Ser Ser Ala Thr Pro Ser
1               5                   10                  15

Arg Pro Asn Val His
            20

<210> SEQ ID NO 175

```
<211> LENGTH: 21
<212> TYPE: PRT
<213> ORGANISM: Homo sapiens

<400> SEQUENCE: 175

Arg Pro Gly Arg Ala Tyr Ser Pro Trp Ala Asn Phe Pro Pro Arg Tyr
1               5                   10                  15

Pro Leu Thr Glu Met
            20

<210> SEQ ID NO 176
<211> LENGTH: 21
<212> TYPE: PRT
<213> ORGANISM: Homo sapiens

<400> SEQUENCE: 176

Ser Pro Pro Asn Asp Ala His Gly Ser Lys Ser Asp Gln Gln Ser Tyr
1               5                   10                  15

Thr Tyr Tyr Ser Asn
            20

<210> SEQ ID NO 177
<211> LENGTH: 16
<212> TYPE: PRT
<213> ORGANISM: Homo sapiens

<400> SEQUENCE: 177

Ile Ile Ala Pro Lys Ala Ser His Arg Asn His Phe His Val Glu Thr
1               5                   10                  15

<210> SEQ ID NO 178
<211> LENGTH: 21
<212> TYPE: PRT
<213> ORGANISM: Homo sapiens

<400> SEQUENCE: 178

Arg Asn Asn Gln Tyr Thr Pro Glu Leu Asn Pro Gln Asn Gly Thr Pro
1               5                   10                  15

Arg Val Ile Tyr Gly
            20

<210> SEQ ID NO 179
<211> LENGTH: 21
<212> TYPE: PRT
<213> ORGANISM: Homo sapiens

<400> SEQUENCE: 179

Arg Pro Ala Ser Asn Pro Ala Pro Trp Ala Ser Ala Gln Thr Gly His
1               5                   10                  15

Arg Leu His Asp Lys
            20

<210> SEQ ID NO 180
<211> LENGTH: 21
<212> TYPE: PRT
<213> ORGANISM: Homo sapiens

<400> SEQUENCE: 180

Asn Arg Ser Gly Leu Gln Ser Pro Trp Ala Ser Pro Asn Val Gly Arg
1               5                   10                  15

Leu Asp Thr Arg Tyr
            20
```

```
<210> SEQ ID NO 181
<211> LENGTH: 21
<212> TYPE: PRT
<213> ORGANISM: Homo sapiens

<400> SEQUENCE: 181

Asn Arg Ser Gly Leu Gln Ser Pro Trp Ala Ser Asp Glu Ser Asp Thr
 1               5                  10                  15

Tyr Lys Tyr Asp Asp
            20

<210> SEQ ID NO 182
<211> LENGTH: 21
<212> TYPE: PRT
<213> ORGANISM: Homo sapiens

<400> SEQUENCE: 182

Thr His Asp Asn Val Pro Ala Pro Trp Ala Ser Leu Tyr Thr Gly Asn
 1               5                  10                  15

His Arg Pro Glu His
            20

<210> SEQ ID NO 183
<211> LENGTH: 21
<212> TYPE: PRT
<213> ORGANISM: Homo sapiens

<400> SEQUENCE: 183

Arg Ser Gly Asn Arg Thr Thr Pro Trp Ala Thr Thr His Asn Ser Thr
 1               5                  10                  15

Ala Gln Pro Glu Tyr
            20

<210> SEQ ID NO 184
<211> LENGTH: 21
<212> TYPE: PRT
<213> ORGANISM: Homo sapiens

<400> SEQUENCE: 184

Asn Arg Ser Gly Leu Gln Ser Pro Trp Ala Ser Ser Asn Val Gly Arg
 1               5                  10                  15

Leu Asp Thr Arg Tyr
            20

<210> SEQ ID NO 185
<211> LENGTH: 21
<212> TYPE: PRT
<213> ORGANISM: Homo sapiens

<400> SEQUENCE: 185

Arg Asn Ala Lys Asp Pro Gly Pro Trp Gly Thr Ala Thr Asn Pro Gly
 1               5                  10                  15

Pro Thr Gln His Arg
            20

<210> SEQ ID NO 186
<211> LENGTH: 94
<212> TYPE: PRT
<213> ORGANISM: Bovis taurus

<400> SEQUENCE: 186

Val Ser Asp Val Pro Arg Asp Leu Glu Val Ile Ala Ala Thr Pro Thr
```

```
                1               5                  10                 15
Ser Leu Leu Ile Ser Trp Asp Ala Pro Ala Val Thr Val Arg Tyr Tyr
                20                 25                 30

Arg Ile Thr Tyr Gly Glu Thr Gly Ser Ser Pro Val Gln Glu Phe
                35                 40                 45

Thr Val Pro Gly Ser Lys Ser Thr Ala Thr Ile Ser Gly Leu Lys Pro
                50                 55                 60

Gly Val Asp Tyr Thr Ile Thr Val Tyr Ala Val Thr Gly Arg Gly Asp
65                 70                 75                 80

Ser Pro Ala Ser Ser Lys Pro Val Ser Ile Asn Tyr Arg Thr
                85                 90
```

<210> SEQ ID NO 187
<211> LENGTH: 92
<212> TYPE: PRT
<213> ORGANISM: Rattus norvegicus

<400> SEQUENCE: 187

```
Val Ser Asp Val Pro Arg Asp Leu Glu Val Ile Ala Ser Thr Pro Thr
1               5                  10                 15

Ser Leu Leu Ile Ser Trp Glu Pro Ala Val Ser Val Arg Tyr Tyr Arg
                20                 25                 30

Ile Thr Tyr Gly Glu Thr Gly Gly Asn Ser Pro Val Gln Glu Phe Thr
                35                 40                 45

Val Pro Gly Ser Lys Ser Thr Ala Thr Ile Asn Ile Lys Pro Gly Ala
                50                 55                 60

Asp Tyr Thr Ile Thr Leu Tyr Ala Val Thr Gly Arg Gly Asp Ser Pro
65                 70                 75                 80

Ala Ser Ser Lys Pro Val Ser Ile Asn Tyr Gln Thr
                85                 90
```

<210> SEQ ID NO 188
<211> LENGTH: 92
<212> TYPE: PRT
<213> ORGANISM: Mus musculus

<400> SEQUENCE: 188

```
Val Ser Asp Ile Pro Arg Asp Leu Glu Val Ile Ala Ser Thr Pro Thr
1               5                  10                 15

Ser Leu Leu Ile Ser Trp Glu Pro Ala Val Ser Val Arg Tyr Tyr Arg
                20                 25                 30

Ile Thr Tyr Gly Glu Thr Gly Gly Asn Ser Pro Val Gln Glu Phe Thr
                35                 40                 45

Val Pro Gly Ser Lys Ser Thr Ala Thr Ile Asn Ile Lys Pro Gly Ala
                50                 55                 60

Asp Tyr Thr Ile Thr Leu Tyr Ala Val Thr Gly Arg Gly Asp Ser Pro
65                 70                 75                 80

Ala Ser Ser Lys Pro Val Ser Ile Asn Tyr Lys Thr
                85                 90
```

<210> SEQ ID NO 189
<211> LENGTH: 40
<212> TYPE: PRT
<213> ORGANISM: Oryctolagus cuniculuc
<220> FEATURE:
<221> NAME/KEY: VARIANT
<222> LOCATION: 24
<223> OTHER INFORMATION: Xaa = Any Amino Acid -continued

```
<400> SEQUENCE: 189

Val Ser Asp Val Pro Arg Asp Leu Glu Val Ile Ala Ser Thr Pro Thr
 1               5                  10                  15

Ser Leu Leu Ile Ser Trp Glu Xaa Pro Ala Val Thr Val Arg Tyr Tyr
             20                  25                  30

Arg Ile Thr Tyr Gly Glu Thr Asn
         35                  40

<210> SEQ ID NO 190
<211> LENGTH: 92
<212> TYPE: PRT
<213> ORGANISM: Gallus gallus

<400> SEQUENCE: 190

Val Ser Asp Val Pro Arg Asp Leu Glu Val Asn Thr Ser Pro Thr Ser
 1               5                  10                  15

Leu Glu Ile Ser Trp Asp Ala Pro Ala Val Thr Val Arg Tyr Tyr Arg
             20                  25                  30

Ile Thr Tyr Gly Glu Thr Gly Gly Ser Ser Pro Val Gln Glu Phe Thr
         35                  40                  45

Val Pro Gly Thr Met Ser Ala Thr Ile Thr Gly Leu Lys Pro Gly Val
     50                  55                  60

Asp Tyr Thr Ile Thr Val Tyr Ala Val Thr Gly Arg Gly Asp Ser Pro
 65                  70                  75                  80

Ala Ser Ser Lys Pro Val Thr Val Thr Tyr Lys Thr
                 85                  90

<210> SEQ ID NO 191
<211> LENGTH: 93
<212> TYPE: PRT
<213> ORGANISM: Xenupus laevis

<400> SEQUENCE: 191

Val Ser Asp Val Pro Thr Asp Leu Glu Val Thr Ser Ser Pro Asn
 1               5                  10                  15

Thr Leu Thr Ile Ser Trp Glu Ala Pro Ala Val Ser Val Arg Tyr Tyr
             20                  25                  30

Arg Ile Thr Tyr Ser Gln Thr Gly Gly Gly Pro Glu Lys Glu Phe Thr
         35                  40                  45

Val Pro Gly Thr Ser Asn Thr Ala Thr Ile Arg Gly Leu Asn Pro Gly
     50                  55                  60

Val Ser Tyr Thr Ile Thr Val Tyr Ala Val Thr Gly Arg Gly Asp Ser
 65                  70                  75                  80

Pro Ala Ser Ser Lys Pro Leu Thr Ile Ile His Lys Thr
                 85                  90

<210> SEQ ID NO 192
<211> LENGTH: 68
<212> TYPE: PRT
<213> ORGANISM: Canis familiaris

<400> SEQUENCE: 192

Ala Asp Ala Pro Ser Leu Phe Leu Ala Thr Thr Pro Ser Leu Leu Val
 1               5                  10                  15

Ser Trp Gln Pro Ala Ile Thr Gly Tyr Ile Ile Lys Tyr Gly Ser Glu
             20                  25                  30

Val Val Pro Gly Val Thr Ala Thr Ile Thr Gly Leu Pro Gly Thr Glu
         35                  40                  45
```

-continued

Tyr Thr Ile Gln Val Ile Ala Leu Lys Asn Gln Lys Ser Leu Ile Gly
 50                  55                  60

Lys Thr Glu Leu
 65

<210> SEQ ID NO 193
<211> LENGTH: 67
<212> TYPE: PRT
<213> ORGANISM: Equus caballis

<400> SEQUENCE: 193

Ala Asp Ala Pro Ser Leu Phe Leu Ala Thr Thr Pro Ser Leu Leu Ile
 1               5                  10                  15

Ser Trp Gln Pro Ala Ile Thr Gly Tyr Ile Ile Lys Tyr Gly Ser Glu
             20                  25                  30

Val Val Pro Gly Val Thr Ala Thr Ile Thr Gly Leu Pro Gly Thr Glu
         35                  40                  45

Tyr Thr Ile Gln Val Ile Ala Ile Lys Asn Gln Lys Ser Leu Ile Gly
 50                  55                  60

Lys Thr Glu
 65

<210> SEQ ID NO 194
<211> LENGTH: 70
<212> TYPE: PRT
<213> ORGANISM: Homo sapiens

<400> SEQUENCE: 194

Val Ser Pro Pro Lys Asp Leu Val Thr Val Thr Val Asn Leu Ala
 1               5                  10                  15

Trp Asp Met Val Thr Tyr Leu Val Val Tyr Thr Pro Thr His Glu Gly
             20                  25                  30

Gly Glu Met Gln Phe Val Pro Gly Asp Gln Thr Ser Thr Ile Ile Gln
         35                  40                  45

Leu Pro Gly Val Glu Tyr Phe Ile Arg Val Phe Ala Ile Leu Asn Lys
 50                  55                  60

Lys Ser Val Ser Ala Val
 65                  70

<210> SEQ ID NO 195
<211> LENGTH: 69
<212> TYPE: PRT
<213> ORGANISM: Sus scrofa

<400> SEQUENCE: 195

Val Ser Pro Pro Lys Asp Leu Val Thr Val Thr Val Asn Leu Ala
 1               5                  10                  15

Trp Asp Met Val Thr Tyr Leu Ile Val Tyr Thr Pro Thr His Glu Gly
             20                  25                  30

Glu Met Gln Phe Val Pro Gly Asp Gln Thr Ser Thr Thr Ile Arg Leu
         35                  40                  45

Pro Gly Val Glu Tyr Phe Ile Arg Val Phe Ala Ile Leu Asn Lys Lys
 50                  55                  60

Ser Val Ser Ala Val
 65

<210> SEQ ID NO 196
<211> LENGTH: 75

```
<212> TYPE: PRT
<213> ORGANISM: Mus musculus

<400> SEQUENCE: 196

Met Asp Gly Pro Gln Asp Leu Val Val Ala Val Thr Pro Thr Thr Leu
1               5                   10                  15

Asp Leu Ser Trp Pro Gln Ala Val Asp Phe Val Val Ser Tyr Val Ser
            20                  25                  30

Ala Gly Asn Arg Val Leu Val Pro Pro Glu Ala Asp Thr Gln Leu Thr
        35                  40                  45

Leu Met Pro Gly Val Glu Tyr Val Val Thr Val Thr Ala Glu Arg Gly
    50                  55                  60

His Ala Val Ser Ala Ser Ile Ala Asn Thr Gly
65                  70                  75

<210> SEQ ID NO 197
<211> LENGTH: 69
<212> TYPE: PRT
<213> ORGANISM: Homo sapiens

<400> SEQUENCE: 197

Thr Val Pro Ser Leu Ile Tyr Val Gly Pro Thr Thr Met His Val Gln
1               5                   10                  15

Trp Gln Val Gly Gly Ala Thr Gly Tyr Ile Leu Ser Tyr Pro Val Asp
            20                  25                  30

Thr Glu Thr Lys Glu Val Leu Gly Pro Thr Val Asn Met Gln Leu Thr
        35                  40                  45

Leu Val Pro Asn Thr Glu Tyr Ala Val Thr Val Gln Ala Val Leu Leu
    50                  55                  60

Thr Ser Val Thr Val
65

<210> SEQ ID NO 198
<211> LENGTH: 44
<212> TYPE: PRT
<213> ORGANISM: Oryctolagus cuniculus

<400> SEQUENCE: 198

Thr Val Pro Ser Leu Asn Ile Tyr Val Gly Pro Thr Thr Met His Val
1               5                   10                  15

Gln Trp Gln Val Gly Gly Ala Thr Gly Tyr Ile Leu Ser Tyr Pro Val
            20                  25                  30

Asp Thr Glu Thr Lys Gln Val Leu Arg Val Thr His
        35                  40

<210> SEQ ID NO 199
<211> LENGTH: 66
<212> TYPE: PRT
<213> ORGANISM: Gallus gallus

<400> SEQUENCE: 199

Leu Ser Asp Leu Leu Tyr Val Ser Ser Met Arg Ala Lys Trp Gly
1               5                   10                  15

Val Ala Gly Ala Thr Gly Tyr Met Ile Leu Tyr Ala Pro Leu Thr Glu
            20                  25                  30

Gly Leu Ala Ala Glu Lys Glu Ile Ile Gly Glu Ala Ser Thr Leu Glu
        35                  40                  45

Leu Asp Gly Leu Leu Pro Asn Thr Glu Tyr Thr Val Thr Val Tyr Ala
    50                  55                  60
```

Met Phe
65

<210> SEQ ID NO 200
<211> LENGTH: 72
<212> TYPE: PRT
<213> ORGANISM: Homo sapiens

<400> SEQUENCE: 200

Leu Ser Asp Leu Leu Tyr Val Thr Ser Met Arg Val Lys Trp Asp Ala
1               5                   10                  15

Val Gly Ala Ser Gly Tyr Leu Ile Leu Tyr Ala Pro Leu Thr Glu Gly
            20                  25                  30

Leu Ala Gly Glu Lys Glu Met Ile Gly Glu Thr His Thr Ile Glu Leu
        35                  40                  45

Ser Gly Leu Leu Pro Asn Thr Glu Tyr Thr Val Thr Val Tyr Ala Met
    50                  55                  60

Phe Gly Ala Ser Asp Val Thr Gly
65                  70

<210> SEQ ID NO 201
<211> LENGTH: 117
<212> TYPE: PRT
<213> ORGANISM: Lama glama

<400> SEQUENCE: 201

Asp Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Gly Ser Thr Tyr
            20                  25                  30

Asp Met Gly Trp Phe Arg Gln Ala Pro Gly Lys Glu Arg Glu Ser Val
        35                  40                  45

Ala Ala Ile Asn Trp Asp Ser Ala Arg Thr Tyr Tyr Ala Ser Ser Val
    50                  55                  60

Arg Gly Arg Phe Thr Ile Ser Arg Asp Asn Ala Lys Lys Thr Val Tyr
65                  70                  75                  80

Leu Gln Met Asn Ser Leu Lys Pro Glu Asp Thr Ala Val Tyr Thr Cys
            85                  90                  95

Gly Ala Gly Glu Gly Gly Thr Trp Asp Ser Trp Gly Gln Gly Thr Gln
            100                 105                 110

Val Thr Val Ser Ser
        115

<210> SEQ ID NO 202
<211> LENGTH: 94
<212> TYPE: PRT
<213> ORGANISM: Homo sapiens

<400> SEQUENCE: 202

Val Ser Asp Val Pro Arg Asp Leu Glu Val Val Ala Ala Thr Pro Thr
1               5                   10                  15

Ser Leu Leu Phe Ser Trp Asp Ala Pro Ala Val Thr Val Arg Tyr Tyr
            20                  25                  30

Arg Ile Thr Tyr Gly Glu Thr Gly Gly Asn Ser Leu Val Gln Glu Phe
        35                  40                  45

Thr Val Pro Gly Ser Lys Ser Thr Ala Thr Ile Ser Gly Leu Lys Pro
    50                  55                  60

-continued

```
Gly Val Asp Tyr Thr Ile Thr Gly Tyr Ala Val Thr Gly Arg Gly Asp
65                  70                  75                  80

Ser Pro Ala Ser Ser Lys Pro Ile Ser Ile Asn Tyr Arg Thr
                85                  90
```